United States Patent
Bretschneider et al.

(10) Patent No.: US 9,066,518 B2
(45) Date of Patent: Jun. 30, 2015

(54) HETEROCYCLIC COMPOUNDS AS PESTICIDES

(71) Applicant: Bayer CropScience AG, Monheim (DE)

(72) Inventors: Thomas Bretschneider, Lohmar (DE); Martin Füßlein, Düsseldorf (DE); Adeline Köhler, Wuppertal (DE); Friedrich August Mühlthau, Bad Soden am Taunus (DE); Eva-Maria Franken, Leichlingen (DE); Arnd Voerste, Köln (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/172,332

(22) Filed: Feb. 4, 2014

(65) Prior Publication Data

US 2014/0221362 A1 Aug. 7, 2014

Related U.S. Application Data

(62) Division of application No. 12/902,878, filed on Oct. 12, 2010, now Pat. No. 8,685,964.

(60) Provisional application No. 61/251,058, filed on Oct. 13, 2009.

(30) Foreign Application Priority Data

Oct. 12, 2009 (EP) .................................... 09172737

(51) Int. Cl.
| | | |
|---|---|---|
| C07D 403/04 | (2006.01) | |
| C07D 403/14 | (2006.01) | |
| A01N 43/54 | (2006.01) | |
| A01N 43/84 | (2006.01) | |
| A01N 43/56 | (2006.01) | |
| A01N 43/647 | (2006.01) | |
| A01N 43/653 | (2006.01) | |
| A01N 43/707 | (2006.01) | |
| A01N 43/76 | (2006.01) | |
| A01N 43/78 | (2006.01) | |
| A01N 43/82 | (2006.01) | |
| A01N 43/88 | (2006.01) | |
| A01N 55/08 | (2006.01) | |
| C07D 213/84 | (2006.01) | |
| C07D 401/04 | (2006.01) | |
| C07D 405/14 | (2006.01) | |
| C07D 413/14 | (2006.01) | |
| C07D 417/14 | (2006.01) | |
| A01N 43/713 | (2006.01) | |
| C07F 5/04 | (2006.01) | |

(52) U.S. Cl.
CPC ............. *A01N 43/84* (2013.01); *A01N 43/56* (2013.01); *A01N 43/647* (2013.01); *A01N 43/653* (2013.01); *A01N 43/707* (2013.01); *A01N 43/76* (2013.01); *A01N 43/78* (2013.01); *A01N 43/82* (2013.01); *A01N 43/88* (2013.01); *A01N 55/08* (2013.01); *C07D 213/84* (2013.01); *C07D 401/04* (2013.01); *C07D 403/04* (2013.01); *C07D 403/14* (2013.01); *C07D 405/14* (2013.01); *C07D 413/14* (2013.01); *C07D 417/14* (2013.01); *A01N 43/54* (2013.01); *A01N 43/713* (2013.01); *C07F 5/04* (2013.01)

(58) Field of Classification Search
CPC ...... C07D 403/04; C07D 403/14; A01N 43/54
USPC .................................. 544/296, 333; 514/256
See application file for complete search history.

(56) References Cited

U.S. PATENT DOCUMENTS

| | | | |
|---|---|---|---|
| 4,176,183 | A | 11/1979 | Baldwin et al. |
| 5,008,275 | A | 4/1991 | Klausener et al. |
| 8,252,723 | B2 | 8/2012 | Jakobi et al. |
| 8,513,260 | B2 | 8/2013 | Schwarz et al. |
| 8,536,204 | B2 | 9/2013 | Bretschneider et al. |
| 8,686,004 | B2 | 4/2014 | Bretschneider et al. |
| 8,809,547 | B2 | 8/2014 | Bretschneider et al. |
| 2008/0305955 | A1 | 12/2008 | Bretschneider et al. |
| 2009/0036310 | A1 | 2/2009 | Jakobi et al. |
| 2009/0076282 | A1 | 3/2009 | Toriyabe et al. |
| 2009/0247551 | A1 | 10/2009 | Jeschke et al. |
| 2009/0253749 | A1 | 10/2009 | Jeschke et al. |
| 2010/0144672 | A1 | 6/2010 | Frackenpohl et al. |

(Continued)

FOREIGN PATENT DOCUMENTS

| | | |
|---|---|---|
| DE | 875 807 | 5/1953 |
| EP | 0 412 849 A2 | 2/1991 |

(Continued)

OTHER PUBLICATIONS

Beveridge et al., One-pot copper catalyzed synthesis of N-functionalized pyrazoles from boronic acids, Tetrahedron Letters, 51, pp. 5005-5008 (available online Jul. 16, 2010).*

Antilla, J.C., et al., "Copper—Diamine-Catalyzed N-Arylation of Pyrroles, Pyrazoles, Indazoles, Imidazoles, and Triazoles," *The Journal of Organic Chemistry* 69:5578-5587, American Chemical Society, United States (2004).

Arnold, Z., et al., "Convenient Preparation of 1,3-Bis(Dimethylamino)-Trimethinium Perchlorate, Tetrafluoroborate and Hexafluorophosphate," *Collect. Czech. Chem. Comm.* 61:1637-1641, Czechoslovak Academy of Sciences, Czech Republic (1996).

Baur, P., et al., "Polydisperse Ethoxylated Fatty Alcohol Surfactants as Accelerators of Cuticular Penetration. 1. Effects of Ethoxy Chain Length and the Size of the Penetrants," *Pesticide Science* 51:131-152, SCI, England (1997).

(Continued)

*Primary Examiner* — Deepak Rao

(74) *Attorney, Agent, or Firm* — Sterne, Kessler, Goldstein & Fox P.L.L.C.

(57) ABSTRACT

The present application relates to the use of heterocyclic compounds, some of which are known, for controlling animal pests including arthropods and in particular insects, furthermore to novel heterocyclic compounds and to processes for their preparation.

14 Claims, No Drawings

(56) References Cited

U.S. PATENT DOCUMENTS

| | | |
|---|---|---|
| 2010/0240705 A1 | 9/2010 | Jeschke et al. |
| 2011/0021539 A1 | 1/2011 | Schwarz et al. |
| 2011/0098287 A1 | 4/2011 | Bretschneider et al. |
| 2011/0118290 A1 | 5/2011 | Bretschneider et al. |
| 2011/0124660 A1 | 5/2011 | Schwarz et al. |
| 2011/0190365 A1 | 8/2011 | Werner et al. |
| 2011/0212949 A1 | 9/2011 | Bretschneider et al. |
| 2011/0275583 A1 | 11/2011 | Bretschneider et al. |
| 2011/0306499 A1 | 12/2011 | Bretschneider et al. |
| 2011/0319428 A1 | 12/2011 | Füßlein et al. |
| 2012/0094837 A1 | 4/2012 | Mühlthau et al. |
| 2012/0095023 A1 | 4/2012 | Bretschneider et al. |
| 2012/0165345 A1 | 6/2012 | Bretschneider et al. |
| 2014/0148471 A1 | 5/2014 | Bretschneider el al. |

FOREIGN PATENT DOCUMENTS

| | | |
|---|---|---|
| EP | 0 539 588 A1 | 5/1993 |
| EP | 1 424 336 A1 | 6/2004 |
| EP | 1 426 366 A1 | 6/2004 |
| EP | 1 668 984 A1 | 6/2006 |
| EP | 1 938 686 A1 | 7/2008 |
| WO | WO 96/32938 A1 | 10/1996 |
| WO | WO 98/56785 A1 | 12/1998 |
| WO | WO 03/051833 A2 | 6/2003 |
| WO | WO 03/093231 A2 | 11/2003 |
| WO | WO 2004/037808 A1 | 5/2004 |
| WO | WO 2005/041950 A1 | 5/2005 |
| WO | WO 2006/044502 A2 | 4/2006 |
| WO | WO 2006/065209 A1 | 6/2006 |
| WO | WO 2007/095229 A2 | 8/2007 |
| WO | WO 2007/149134 A1 | 12/2007 |
| WO | WO 2008/073942 A2 | 6/2008 |
| WO | WO 2008/077483 A1 | 7/2008 |
| WO | WO 2008/104077 A1 | 9/2008 |
| WO | WO 2009/018185 A2 | 2/2009 |

OTHER PUBLICATIONS

Bjorklund, M.D. and Coburn, M.D., "3,3-Dinitrobutyl-1,2,4-oxadiazoles," *Journal of Heterocyclic Chemistry* 17:819-821, HeteroCorporation, United States (1980).

Cai, D., et al., "A Study of the Lithiation of 2,6-Dibromopyridine with Butyllithium, and its Application to Synthesis of L-739,010," *Tetrahedron Letters* 37(15): 2537-2540, Elsevier Science Ltd., England (1996).

Cativiela, C., et al., "New Efficient Synthesis of 3(5)-Carbomethoxy-4-Aryl Pyrazoles from 3-Aryl-2,3-Dehydroamino Acid Derivatives," *Synthetic Communications* 17(2):165-172, Marcel Dekker, Inc., United States (1987).

Church, R., et al, "New Synthetic Routes to 3-, 5-, and 6-Aryl-2-chloropyridines," *The Journal of Organic Chemistry* 60:3750-3758, American Chemical Society, United States (1995).

Coppola, G.M., et al., "Synthesis and Reactions of 2-Aryl-3-(dimethylamino)acroleins," *Journal of Heterocyclic Chemistry* 11:51-56, HeteroCorporation, United States (1974).

Cromwell, N.H. and Mitsch, R.A., "Indenoquinolines. I. Derivatives of 11$H$-Indeno[1,2-$b$]quinoline," *The Journal of Organic Chemistry* 26:3812-3817, American Chemical Society, United States (1961).

Cristau, H.-J., et al., "Mild Conditions for Copper-Catalysed N-Arylation of Pyrazoles," *European Journal of Organic Chemistry* 2004:695-709,Wiley-VCH Verlag GmbH & Co. KgaA, Germany (2004).

Daniels, R.N., et al., "Microwave-assisted protocols for the expedited synthesis of pyrazolo[1,5-$a$] and [3,4-$d$]pyrimidines," *Tetrahedron Letters* 49:305-310, Elsevier Ltd., England (2008).

Diana, G.D., et al., "Oxadiazoles as Ester Bioisosteric Replacements in Compounds Related to Disoxaril. Antirhinovirus Activity," *Journal of Medicinal Chemistry* 37(15):2421-2436, American Chemical Society, United States (1994).

Gompper, R., et al., "Synthesis of Oligo(diazaphenyls). Tailor-Made Fluorescent Heteroaromatics and Pathways to Nanostructures," *Synthesis* 28:696-708, Thieme Medical Publishers, Germany (1997).

Gupton, J.T., et al., "An Alternative Preparation of the 2-Dimethylaminomethylene-1,3-bis(dimethylimmonio)propane Salt from Phosphonoacetic Acids and Some Applications in Heterocyclic Synthesis," *The Journal of Heterocyclic Chemistry* 28: 1281-1285, HeteroCorporation, United States (1991).

Gupton, J.T., et al., "The Preparation and Some Reactions of 2-(Arylsulfonyl)vinamidinium Salts," *The Journal of Organic Chemistry* 56:976-980, American Chemical Society, United States (1991).

Hargreaves, S.L., "The synthesis of substituted pyridylpyrimidine fungicides using palladium-catalysed cross-coupling reactions," *Tetrahedron Letters* 41:1653-1656, Elsevier Science Ltd., England (2000).

Jameson, D.L. and Goldsby, K.A., "2,6-Bis($N$-pyrazolyl)pyridines: The Convenient Synthesis of a Family of Planar Tridentate $N_3$ Ligands That Are Terpyridine Analogues," *The Journal of Organic Chemistry* 55:4992-4994, American Chemical Society, United States (1990).

Kaneko, K., et al., "Preparation of 2-Aryl-4a,5-Dihydro-4$H$-[1,3,4]oxadiazino[4,5-a]indoles as a [$a$]-Fused Indole Derivatives," *Heterocycles* 37(3):1645-1656, The Japan Institute of Heterocyclic Chemistry, Japan (1994).

Kelly T.R., et al., "A Molecular Brake," *Journal of American Chemical Society* 116:3657-3658, American Chemical Society, United States (1994).

Khan, M.A. and Pinto, A.A.A., "Hetarylpyrazoles. II. Reactions of Pyrazol-1'-ylpyridines," *Journal of Heterocyclic Chemistry* 18:9-14, HeteroCorporation, United States (1981).

Kuo, G.-H., et al., "Synthesis and Discovery of Pyrazine—Pyridine Biheteroaryl as a Novel Series of Potent Vascular Endothelial Growth Factor Receptor-2 Inhibitors," *Journal of Medicinal Chemistry* 48:1886-1900, American Chemical Society, United States (2005).

Li, J.J., et al., "A Practical Buchwald—Hartwig Amination of 2-Bromopyridines with Volatile Amines," *The Journal of Organic Chemistry* 72:3606-3607, American Chemical Society, United States (2007).

Lipshutz, B.H., et al., "Copper-in-Charcoal (Cu/C): Heterogeneous, Copper—Catalyzed Asymmetric Hydrosilylations," *Angewandte Chemie* 118:1281-1286, Wiley-VCH Verlag GmbH & Co. KgaA, Germany (2006).

Moyroud, J., et al., "Synthesis of Pyrozolo[1,5-$b$][1,2]Benzisothiazoles," *Heterocycles* 43(1):221-228, The Japan Institute of Heterocyclic Chemistry, Japan (1996).

Neilson, D.G., et al., "The Chemistry of Amidrazones," *Chemical Reviews* 70:151-170, American Chemical Society, United States (1970).

Ogunrombi, M.O., et al., "Structure—activity relationships in the inhibition of monoamine oxidase B by 1-methyl-3-phenylpyrroles," *Bioorganic & Medicinal Chemistry* 16:2463-2472, Elsevier Ltd., England (2008).

Okamoto, T. and Tani, H., "Reaction Mechanism in Aromatic Heterocyclic Compound. I. The Reactions of N-Alkoxypyridinium Derivatives," *Chem. Pharm. Bull.* 7:925-930, The Pharmaceutical Society of Japan, Japan (1959).

Roppe, J., et al., "Discovery of Novel Heteroarylazoles That are Metabotropic Glutamate Subtype 5 Receptor Antagonists with Anxiolytic Activity," *Journal of Medicinal Chemistry* 47:4645-4648, American Chemical Society, United States (2004).

Sakamoto, T., et al., "Preparation and palladium-catalysed arylation of indolylzinc halides," *Journal of the Chemical Society-Perkin Transactions 1* 16:1927-1934, Royal Society of Chemistry, England (1996).

Sauer, J., et al., "From 1,2,4-Triazines and Tributyl(ethynyl)tin to Stannylated Bi- and Terpyridines: The Cycloaddition Pathway," *European Journal of Organic Chemistry* 1999:313-321, Wiley-VCH Verlag GmbH, Germany (1999).

Trécourt, F., et al., "New Syntheses of Substituted Pyridines via Bromine—Magnesium Exchange," *Tetrahedron* 56:1349-1360, Elsevier Science Ltd., England (2000).

Trécourt, F., et al., "Pyridylmagnesium Chlorides from Bromo and Dibromopyridines by Bromine-Magnesium Exchange: A Convenient Access to Functionalized Pyridines," *Tetrahedron Letters* 40:4339-4342, Elsevier Science Ltd., England (1999).

(56) References Cited

OTHER PUBLICATIONS

De Voghel, G.J., "Phosgene Immonium Salts. XIII. Dichloromalonyl Cyanines and 3,5-Bis(dimethylamino)pyrazoles," *The Journal of Organic Chemistry* 39:1233-1235, American Chemical Society, United States (1974).

Weiberth, F.J. and Hall, S.S., "Copper(I)-Activated Addition of Grignard Reagents to Nitriles. Synthesis of Ketimines, Ketones, and Amines," *The Journal of Organic Chemistry* 52:3901-3904, American Chemical Society, United States (1987).

Wellmar, U., et al., "Syntheses of Various 5-(Bromoaryl)-substituted Uracils," *Journal of Heterocyclic Chemistry* 32:1159-1163, HeteroCorporation, United States (1995).

Xuhong, Q. and Idoux, J.P., "A Synthetic and MO-SCF Study of the Trifluoroethoxylation of Trifluoromethylchloropyridine Derivatives," *Journal of Fluorine Chemistry* 53:143-153, Elsevier Sequoia, Laussane, France (1991).

Yamaguchi, S., et al., "Furopyridines. XXIX [1]. Reactions of Furo[2,3-*b*:4,5-*c*']-, - [3,2-b:-4,5-c']-, -[2,3-c:4,5-c']- and -[3,2-c:3,2-c']dipyridine," *Journal of Heterocyclic Chemistry* 36:81-94, HeteroCorporation, United States (1999).

Yamanaka, H., et al., "Preparation of Novel β-Trifluoromethyl Vinamidinium Salt and Its Synthetic Application to Trifluoromethylated Heterocycles," *Tetrahedron Letters* 37(11):1829-1832, Elsevier Science Ltd., England (1996).

English language Abstract of International Patent Application Publication No. WO 98/56785 A1, European Patent Office—espacenet Worldwide (1998).

Fujisawa, T. and Sato, T., "Reduction of Carboxylic Acids to Aldehydes: 6 Oxodecanal," *Organic Syntheses, Coll.* 66:121, Organic Synthesis, Inc., United States (1988).

Office Action mailed Oct. 27, 2014 in U.S. Appl. No. 14/169,849, inventors Bretschneider, T., et al., filed Jan. 31, 2014.

* cited by examiner

HETEROCYCLIC COMPOUNDS AS PESTICIDES

This application is a divisional of U.S. Pat. No. 8,685,964, filed Oct. 12, 2010, which claims the benefit of U.S. Provisional Application No. 61/251,058, filed Oct. 13, 2009; and European Patent Application No. 09172737.0, filed Oct. 12, 2009, all of which are incorporated by reference herein.

The present application relates to the use of heterocyclic compounds, some of which are known, for controlling animal pests including arthropods and in particular insects, furthermore to novel heterocyclic compounds and to processes for their preparation.

Certain pyrazolyl compounds are already known; however, a use for controlling animal pests has hitherto not been described (cf. WO 2003/051833 A2, WO 2006/044502 A2).

WO 1998/056785 A1 and WO 1996/032938 A1, too, disclose pyrazole compounds, for which pharmaceutical applications are stated.

Modern crop protection agents have to satisfy many demands, for example with respect to efficacy, persistence and spectrum of their action and possible use. Questions of toxicity, the combinability with other active compounds or formulation auxiliaries play a role, as well as the question of the expense that the synthesis of an active compound requires. Furthermore, resistances may occur. For all these reasons, the search for novel crop protection agents cannot be considered as having been concluded, and there is a constant need for novel compounds having properties which, compared to the known compounds, are improved at least in respect of individual aspects.

It was an object of the present invention to provide compounds which widen the spectrum of the pesticides under various aspects.

This object and further objects not explicitly mentioned which can be derived or deduced from the context discussed here are, in part, achieved by novel compounds of the formula (I),

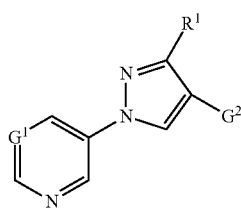

(I)

in which
$G^1$ represents N, CH, C-halogen, C-nitro, C-cyano, C-alkyl, C-haloalkyl, C-cycloalkyl, C-alkoxy, C-haloalkoxy,
$R^1$ represents hydrogen, alkyl, haloalkyl, cycloalkyl, halogen, cyano, alkoxy, haloalkoxy, amino, alkylamino, dialkylamino or alkylthio and
$G^2$ represents optionally substituted heterocyclyl, represents optionally substituted heteroaryl or represents optionally substituted aryl,
and also salts, metal complexes and N-oxides of the compounds of the formula (I), which can be used for controlling pests.

It has been found that the compounds of the formula (I) have pronounced biological properties and are suitable especially for controlling animal pests, in particular insects, arachnids and nematodes, encountered in agriculture, in forests, in the protection of stored products and materials and in the hygiene sector.

The known compounds of the formula (I) can be obtained by the preparation processes described in the publications mentioned above.

The formula (I) provides a general definition of the compounds to be used according to the invention.

Preferred substituents or ranges of the radicals cited in the compounds of the formula (I) mentioned above are illustrated below.

Preference is given to using compounds of the formula (I) in which
$G^1$ represents N, CH, C-halogen C-nitro, C-cyano, C-alkyl, C-haloalkyl, C-cycloalkyl, C-alkoxy, C-haloalkoxy,
$R^1$ represents hydrogen, alkyl, haloalkyl, cycloalkyl, halogen, cyano, alkoxy, haloalkoxy, amino, alkylamino, dialkylamino or alkylthio,
$G^2$ represents $A-R^2_a$, $D-R^3_b$ or $E-R^4_c$ in which
A represents heterocyclyl from the group consisting of 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, oxazolin-2-yl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 5,6-dihydro-[1,3,4]-oxadiazin-2-yl, 5,6-dihydro-[1,3,4]-thiadiazin-2-yl, 5,6-dihydro-[1,4,2]-dioxazin-3-yl, hydroxypyridyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,3-dihydrothien-2-yl, 2,3-dihydrothien-3-yl, 2,4-dihydrothien-2-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl,
$R^2$ represents a radical from the group consisting of halogen, cyano, nitro, alkyl, haloalkyl, optionally substituted cycloalkyl, alkoxy, haloalkoxy, alkylthio, haloalkylthio, alkylsulphinyl, alkylsulphonyl, haloalkylsulphinyl, haloalkylsulphonyl, amino, alkylamino, dialkylamino, alkylcarbonylamino, alkoxycarbonylamino, alkoxyalkyl, haloalkoxyalkyl, alkenyl, alkynyl, optionally substituted cycloalkylalkyl, alkylcarbonyl, alkoxycarbonyl, aminocarbonyl, pyridyl and pyrimidyl (where pyridyl and pyrimidyl for their part may be substituted by halogen, alkyl, haloalkyl, alkoxy and haloalkoxy), a represents a number from the group consisting of 0, 1, 2 and 3, D represents a heteroaryl radical from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyrid-2-yl, pyrid-3-yl, pyrimid-2-yl, pyrimid-4-yl, imidazolyl, pyrazol-1-yl, pyrazol-3-yl pyrazinyl, 1,2,3-triazinyl, 1,2,4-triazinyl, 1,3,5-triazinyl, thiazol-2-yl, thiazol-4-yl 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl and oxazolyl), $R^3$ represents a radical from the group consisting of halogen, nitro, amino, formyl, cyano, alkylamino, haloalkylamino, dialkylamino, alkyl, haloalkyl, optionally substituted cycloalkyl, optionally substituted cycloalkenyl, optionally substituted cycloalkylalkyl, where in the cycloalkyl moiety of the cycloalkylalkyl radical one or two $CH_2$ groups may be replaced by oxygen or sulphur, but two oxygen atoms must not be directly adjacent to one another, alkoxy, haloalkoxy, alkoxyalkyl, halogenated alkoxyalkyl, bis(alkoxy)alkyl, bis(haloalkoxy)alkyl, alkoxy(alkylsulphanyl)alkyl, alkoxy(alkylsulphinyl)alkyl, alkoxy(alkylsulphonyl)alkyl, bis(alkylsulphanyl)alkyl, bis(haloalkylsulphanyl)alkyl, bis(hydroxyalkylsulphanyl)alkyl, alkoxycarbonyl, alkoxycarbonylalkyl, alpha-hydroxyimino-alkoxycarbonylalkyl, alpha-alkoxyimino-alkoxycarbonylalkyl, $C(X)NR^5R^6$ (in which X represents oxygen, sulphur, $NR^{15}$ or NOH, $R^5$ represents hydrogen or alkyl and $R^6$ and $R^{15}$ independently of one another represent a radical from the group consisting of hydrogen, alkyl, haloalkyl, cyanoalkyl, alkynyl, cycloalkyl, cycloalkylalkyl, alkylcarbonyl, alkoxyalkyl, alkoxycarbonyl, alkoxycarbonylalkyl, alkylthioalkyl, aryl, arylalkyl and hetarylalkyl and $R^6$ may also represent OH or $R^5$ and $R^6$ together with the nitrogen atom to which they are attached form a ring which may contain one or more further heteroatoms from the group consisting of NH, $NCH_3$, $NC_2H_5$, oxygen and sulphur, where two oxygen atoms must not be directly adjacent to one another or $R^5$ and $R^{15}$ together with the nitrogen atoms to which they are attached form a ring which may contain one or more further heteroatoms from the group consisting of NH, $NCH_3$, $NC_2H_5$, oxygen and sulphur, where two oxygen atoms must not be directly adjacent to one another), $NR^7R^8$ (in which $R^7$ represents hydrogen or alkyl and $R^8$ represents a radical from the group consisting of hydrogen, alkyl, haloalkyl, cyanoalkyl, alkynyl, cycloalkyl, cycloalkylalkyl, alkoxy, haloalkoxy, alkoxyalkyl, alkoxycarbonyl, alkoxycarbonylalkyl, alkylthioalkyl, aryl, arylalkyl and hetarylalkyl or $R^7$ and $R^8$ together with the nitrogen atom to which they are attached form a ring which may contain one or more further heteroatoms from the group consisting of NH, $NCH_3$, $NC_2H_5$, oxygen and sulphur, where two oxygen atoms must not be directly adjacent to one another), alkylthio, alkylsulphinyl, alkylsulphonyl, the heterocyclyl radicals cycloalkyl and cycloalkenyl in which one or two $CH_2$ groups are replaced by oxygen or sulphur, where two oxygen atoms must not be directly adjacent to one another, in particular dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide (where in these heterocyclyl radicals two hydrogen atoms attached to the same carbon atom may be replaced by =$CH_2$, —$CH_2$—$CH_2$, —$CH_2$—$CH_2$—CH or —$CH_2$—$CH_2$—$CH_2$—$CH_2$—), morpholinyl, triazolinonyl, oxazolinyl, dihydrooxadiazinyl, dihydrodioxazinyl, dihydrooxazolyl, dihydrooxazinyl and pyrazolinonyl (where all heterocyclyl radicals for their part may be substituted by alkyl, haloalkyl, alkoxy and alkoxyalkyl), phenyl (which for its part may be substituted by halogen, cyano, nitro, alkyl and haloalkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl and cycloalkyl) and the heteroarylalkyl radicals triazolylalkyl, pyridylalkyl, pyrimidylalkyl and oxadiazolylalkyl (which for their part may be substituted by halogen and alkyl), b represents a number from the group consisting of 0, 1, 2 and 3, E represents aryl, in particular phenyl, $R^4$ represents a radical from the group consisting of halogen, nitro, amino, formyl, cyano, alkylamino, haloalkylamino, dialkylamino, alkyl, haloalkyl, optionally substituted cycloalkyl, optionally substituted cycloalkenyl, optionally substituted cycloalkylalkyl, where in the cycloalkyl moiety of the cycloalkylalkyl radical one or two $CH_2$ groups may be replaced by oxygen or sulphur, but two oxygen atoms must not be directly adjacent to one another, alkoxy, haloalkoxy, alkoxyalkyl, halogenated alkoxyalkyl, bis(alkoxy)alkyl, bis(haloalkoxy)alkyl, alkoxy(alkylsulphanyl)alkyl, alkoxy(alkylsulphinyl)alkyl, alkoxy(alkylsulphonyl)alkyl, bis(alkylsulphanyl)alkyl, bis(haloalkylsulphanyl)alkyl, bis(hydroxyalkylsulphanyl)alkyl, alkoxycarbonyl, alkoxycarbonylalkyl, alpha-hydroxyimino-alkoxycarbonylalkyl, alpha-alkoxyimino-alkoxycarbonylalkyl, $C(X)NR^5R^6$ (in which X represents oxygen, sulphur, $N^{15}$ or NOH, $R^5$ represents hydrogen or alkyl and $R^6$ and $R^{15}$ independently of one another represent a radical from the group consisting of hydrogen, alkyl, haloalkyl, cyanoalkyl, alkynyl, cycloalkyl, cycloalkylalkyl, alkylcarbonyl, alkoxyalkyl, alkoxycarbonyl, alkoxycarbonylalkyl, alkylthioalkyl, aryl, arylalkyl and hetarylalkyl and $R^6$ may also represent OH or $R^5$ and $R^6$ together with the nitrogen atom to which they are attached form a ring which may contain one or more further heteroatoms from the group consisting of NH, $NCH_3$, $NC_2H_5$, oxygen and sulphur, where two oxygen atoms must not be directly adjacent to one another or $R^5$ and $R^{15}$ together with the nitrogen atoms to which they are attached form a ring which may contain one or more further heteroatoms from the group consisting of NH, $NCH_3$, $NC_2H_5$, oxygen and sulphur, where two oxygen atoms must not be directly adjacent to one another), $NR^7R^8$ (in which $R^7$ represents hydrogen or alkyl and $R^8$ represents a radical from the group consisting of hydrogen, alkyl, haloalkyl, cyanoalkyl, alkynyl, cycloalkyl, cycloalkylalkyl, alkoxy, haloalkoxy, alkoxyalkyl, alkoxycarbonyl, alkoxycarbonylalkyl, alkylthioalkyl, aryl, arylalkyl and hetarylalkyl or $R^7$ and $R^8$ together with the nitrogen atom to which they are attached form a ring which may contain one or more further heteroatoms from the group consisting of NH, $NCH_3$, $NC_2H_5$, oxygen and sulphur), alkylthio, alkylsulphinyl, alkylsulphonyl, the heterocyclyl radicals cycloalkyl and cycloalkenyl in which one or two $CH_2$ groups are replaced by oxygen or sulphur, where two oxygen atoms must not be directly adjacent to one another, in particular dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide (where in these heterocyclyl radicals two hydrogen atoms attached to the same carbon atom may be replaced by $=CH_2$, $-CH_2CH_2-$, $-CH_2CH-CH_2-$ or $-CH_2-CH_2-CH-CH_2-$), morpholinyl, triazolinonyl, oxazolinyl, dihydrooxadiazinyl, dihydrodioxazinyl, dihydrooxazolyl, dihydrooxazinyl and pyrazolinonyl (where all heterocyclyl radicals for their part may be substituted by alkyl, haloalkyl, alkoxy and alkoxyalkyl), phenyl (which for its part may be substituted by halogen, cyano, nitro, alkyl and haloalkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl and cycloalkyl) and the heteroarylalkyl radicals triazolylalkyl, pyridylalkyl, pyrimidylalkyl and oxadiazolylalkyl (which for their part may be substituted by halogen and alkyl), and c represents a number from the group consisting of 0, 1, 2 and 3, and also salts, metal complexes and N-oxides of the compounds of the formula (I).

Particular preference is given to using compounds of the formula (I) in which $G^1$ represents N, CH, C-halogen, C-nitro, C-cyano, C—($C_1$-$C_6$)-alkyl, C—($C_1$-$C_6$)-haloalkyl, C—($C_3$-$C_6$)-cycloalkyl, C—($C_1$-$C_6$)-alkoxy, C—($C_1$-$C_6$)-haloalkoxy, in particular N, CH, C-halogen, C-cyano, C-trifluoromethyl, $R^1$ represents hydrogen, $C_1$-$C_6$-alkyl, $C_1$-$C_6$-haloalkyl, $C_3$-$C_6$-cycloalkyl, halogen, cyano, $C_1$-$C_6$-alkoxy, $C_1$-$C_6$-haloalkoxy, amino, $C_1$-$C_6$-alkylamino, di-($C_1$-$C_6$)-alkylamino or $C_1$-$C_6$-alkylthio, in particular hydrogen and methyl and $G^2$ represents $A-R^2{}_a$, $D-R^3{}_b$ or $E-R^4{}_c$ in which A represents heterocyclyl from the group consisting of oxazolin-2-yl, 5,6-dihydro-[1,3,4]-oxadiazin-2-yl, 5,6-dihydro-[1,3,4]-thiadiazin-2-yl, 5,6-dihydro-[1,4,2]-dioxazin-3-yl and hydroxypyridyl, $R^2$ represents a radical from the group consisting of halogen, cyano, nitro, $C_1$-$C_6$-alkyl, $C_1$-$C_6$-haloalkyl, optionally halogen-, cyano-, $C_1$-$C_6$-alkyl-, $C_1$-$C_6$-haloalkyl- and $C_1$-$C_6$-alkoxy-substituted $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-haloalkylsulphinyl, $C_1$-$C_6$-haloalkylsulphonyl, amino, $C_1$-$C_6$-alkylamino, di-($C_1$-$C_6$-alkyl)amino, $C_1$-$C_6$-alkylcarbonylamino, $C_1$-$C_6$-alkoxycarbonylamino, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-alkynyl, optionally halogen-, cyano-, $C_1$-$C_6$-alkyl-, $C_1$-$C_6$-haloalkyl- and $C_1$-$C_6$-alkoxy-substituted $C_3$-$C_6$-cycloalkyl-$C_1$-$C_6$-alkyl, $C_1$-$C_6$-alkylcarbonyl, $C_1$-$C_6$-alkoxycarbonyl, aminocarbonyl, pyridyl and pyrimidyl (where pyridyl and pyrimidyl for their part may be substituted by halogen, $C_1$-$C_6$-alkyl, $C_1$-$C_6$-haloalkyl, $C_1$-$C_6$-alkoxy and $C_1$-$C_6$-haloalkoxy), a represents a number from the group consisting of 0, 1, 2 and 3, D represents a heteroaryl radical from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyrid-2-yl, pyrid-3-yl, pyrimid-2-yl, pyrimid-4-yl, imidazolyl, pyrazol-1-yl, pyrazol-3-yl pyrazinyl, 1,2,3-triazinyl, 1,2,4-triazinyl, 1,3,5-triazinyl, thiazol-2-yl, thiazol-4-yl 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl and oxazolyl).

$R^3$ represents a radical from the group consisting of halogen, nitro, amino, formyl, cyano, $C_1$-$C_6$-alkylamino, $C_1$-$C_6$-haloalkylamino, di-($C_1$-$C_6$-alkyl)amino, $C_1$-$C_6$-alkyl, $C_1$-$C_6$-haloalkyl, optionally halogen-, cyano-, $C_1$-$C_6$-alkyl-, $C_1$-$C_6$-haloalkyl- and $C_1$-$C_6$-alkoxy-substituted $C_3$-$C_6$-cycloalkyl, optionally halogen-, cyano-, $C_1$-$C_6$-alkyl-, $C_1$-$C_6$-haloalkyl- and $C_1$-$C_6$-alkoxy-substituted $C_3$-$C_6$-cycloalkenyl, optionally halogen-, cyano-, $C_1$-$C_6$-alkyl-, $C_1$-$C_6$-haloalkyl- and $C_1$-$C_6$-alkoxy-substituted $C_3$-$C_6$-cycloalkyl-$C_1$-$C_6$-alkyl where in the cycloalkyl moiety, if 5- or 6-membered, of the cycloalkylalkyl radical one or two $CH_2$ groups may be replaced by oxygen or sulphur, but two oxygen atoms must not be directly adjacent to one another, $C_1$-$C_6$-alkoxy, $C_1$-$C_6$-haloalkoxy, $C_1$-$C_6$-alkoxy-$C_1$-$C_6$-alkyl, halogenated $C_1$-$C_6$-alkoxy-$C_1$-$C_6$-alkyl, bis($C_1$-$C_6$-alkoxy)-$C_1$-$C_6$-alkyl, bis($C_1$-$C_6$-haloalkoxy)-$C_1$-$C_6$-alkyl, $C_1$-$C_6$-alkoxy($C_1$-$C_6$-alkylsulphanyl)-$C_1$-$C_6$-alkyl, $C_1$-$C_6$-alkoxy($C_1$-$C_6$-alkylsulphinyl)-$C_1$-$C_6$-alkyl, $C_1$-$C_6$-alkoxy($C_1$-$C_6$-alkylsulphonyl)-$C_1$-$C_6$-alkyl, bis($C_1$-$C_6$-alkylsulphanyl)-$C_1$-$C_6$-alkyl, bis($C_1$-$C_6$-haloalkylsulphanyl)-$C_1$-$C_6$-alkyl, bis($C_1$-$C_6$-hydroxyalkylsulphanyl)-$C_1$-$C_6$-alkyl, $C_1$-$C_6$-alkoxycarbonyl, $C_1$-$C_6$-alkoxycarbonyl-$C_1$-$C_6$-alkyl, alpha-hydroxyimino-$C_1$-$C_6$-alkoxycarbonylmethyl, alpha-$C_1$-$C_6$-alkoxyimino-$C_1$-$C_6$-alkoxycarbonylmethyl, $C(X)NR^5R^6$, (in which X represents oxygen, sulphur, $NR^{15}$ or NOH, $R^5$ represents hydrogen or $C_1$-$C_6$-alkyl and $R^6$ and $R^{15}$ independently of one another represent a radical from the group consisting of hydrogen, $C_1$-$C_6$-alkyl, $C_1$-$C_6$-haloalkyl, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkylcarbonyl, $C_1$-$C_6$-alkoxy-$C_1$-$C_6$-alkyl, $C_1$-$C_6$-alkoxycarbonyl, $C_1$-$C_6$-alkoxycarbonyl-$C_1$-$C_6$-alkyl, $C_1$-$C_6$-alkylthio-$C_1$-$C_6$-alkyl, phenyl, phenyl-$C_1$-$C_6$-alkyl or hetaryl-$C_1$-$C_6$-alkyl in which hetaryl represents pyrimidyl and $R^6$ may also represent OH or $R^5$ and $R^6$ together with the nitrogen atom to which they are attached form a 5- to 7-membered ring which may contain one further heteroatom from the group consisting of NH, $NCH_3$, $NC_2H_5$, oxygen and sulphur or $R^5$ and $R^{15}$ together with the nitrogen atoms to which they are attached form a 5- to 7-membered ring which may contain one or more, in particular one or two, further heteroatoms from the group consisting of NH, NCH$_3$, NC$_2$H$_5$, oxygen and sulphur, where two oxygen atoms must not be directly adjacent to one another), NR$^7$R$^8$ (in which R$^7$ represents hydrogen or C$_1$-C$_6$-alkyl and R$^8$ represents a radical from the group consisting of hydrogen, C$_1$-C$_6$-alkyl, C$_1$-C$_6$-haloalkyl, cyano-C$_1$-C$_6$-alkyl, C$_2$-C$_6$-alkynyl, C$_3$-C$_6$-cycloalkyl, C$_3$-C$_6$-cycloalkyl-C$_1$-C$_6$-alkyl, C$_1$-C$_6$-alkoxy, C$_1$-C$_6$-haloalkoxy, C$_1$-C$_6$-alkoxy-C$_1$-C$_6$-alkyl, C$_1$-C$_6$-alkoxycarbonyl, C$_1$-C$_6$-alkoxycarbonyl-C$_1$-C$_6$-alkyl, C$_1$-C$_6$-alkylthio-C$_1$-C$_6$-alkyl, phenyl, phenyl-C$_1$-C$_6$-alkyl and hetaryl-C$_1$-C$_6$-alkyl in which hetaryl represents pyrimidyl or R$^7$ and R$^8$ together with the nitrogen atom to which they are attached form a 5- to 7-membered ring which may contain one further heteroatom from the group consisting of NH, NCH$_3$, NC$_2$H$_5$, oxygen and sulphur), C$_1$-C$_6$-alkylthio, C$_1$-C$_6$-alkylsulphinyl, C$_1$-C$_6$-alkylsulphonyl, the heterocyclyl radicals C$_3$-C$_8$-cycloalkyl and C$_4$-C$_8$-cycloalkenyl in which one or two CH$_2$ groups are replaced by oxygen or sulphur, where two oxygen atoms must not be directly adjacent to one another, in particular dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide (where in these heterocyclyl radicals two hydrogen atoms attached to the same carbon atom may be replaced by =CH$_2$, —CH$_2$—CH$_2$—, —CH$_2$—CH$_2$—CH$_2$— or —CH$_2$—CH$_2$—CH$_2$—CH$_2$—), morpholinyl, triazolinonyl, oxazolinyl, dihydrooxadiazinyl, dihydrodioxazinyl, dihydrooxazolyl, dihydrooxazinyl and pyrazolinonyl (in particular 1,3-dioxolan-2-yl, 1,3-dioxan-2-yl, 1,3-dioxepan-2-yl, 1,3-dioxocan-2-yl, 1,3-oxathian-2-yl, 1,3-oxathiolan-2-yl, 1,3-oxathiepan-2-yl, 1,3-oxathiocan-2-yl, 1,3-dithian-2-yl, 1,3-dithiolan-2-yl, 1,3-dithiepan-2-yl, 1,3-dithiocan-2-yl, 4,5-dihydro-1,3-oxazol-2-yl, 5,6-dihydro-4H-1,3-oxazin-2-yl, 1,3-oxathianyl 3-oxide, 1,3-oxathiolanyl 3-oxide, 1,3-oxathiepanyl 3-oxide, 1,3-oxathiocanyl 3-oxide, 1,3-oxathianyl 3,3-dioxide, 1,3-oxathiolanyl 3,3-dioxide, 1,3-oxathiepanyl 3,3-dioxide, 1,3-oxathiocanyl 3,3-dioxide (where in these heterocyclyl radicals two hydrogen atoms attached to the same carbon atom may be replaced by =CH$_2$, —CH$_2$—CH$_2$—, —CH$_2$—CH$_2$—CH$_2$— or —CH$_2$—CH$_2$—CH$_2$—CH$_2$—) and 1,2,4-triazolin-3-on-2-yl) (where all heterocyclyl radicals for their part may be substituted by C$_1$-C$_6$-alkyl, C$_1$-C$_6$-haloalkyl, C$_1$-C$_6$-alkoxy and C$_1$-C$_6$-alkoxy-C$_1$-C$_6$-alkyl), phenyl (which for its part may be substituted by halogen, cyano, nitro, C$_1$-C$_6$-alkyl and C$_1$-C$_6$-haloalkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (in particular pyrid-2-yl, pyrimid-2-yl, pyrimid-4-yl, pyrazol-1-yl, pyrazol-3-yl, pyrazol-5-yl, 1,2,4-oxadiazol-3-yl, 1,2,4-triazol-3-yl, 1,2,3-triazol-1-yl, 1,2,3-triazol-2-yl, 1,2,4-thiadiazol-3-yl and 1,2,4-triazin-3-yl) (which for their part may be substituted by halogen, nitro, C$_1$-C$_6$-alkyl, C$_1$-C$_6$-haloalkyl, C$_1$-C$_6$-alkoxy, C$_1$-C$_6$-haloalkoxy, C$_1$-C$_6$-alkoxy-C$_1$-C$_6$-alkyl, C$_1$-C$_6$-alkylthio, C$_1$-C$_6$-alkylthio-C$_1$-C$_6$-alkyl and C$_3$-C$_6$-cycloalkyl) and the heteroarylalkyl radicals triazolyl-C$_1$-C$_6$-alkyl, pyridyl-C$_1$-C$_6$-alkyl, pyrimidyl-C$_1$-C$_6$-alkyl and oxadiazolyl-C$_1$-C$_6$-alkyl (which for their part may be substituted by halogen and C$_1$-C$_6$-alkyl), b represents a number from the group consisting of 0, 1, 2 and 3, E represents phenyl, R$^4$ represents a radical from the group consisting of halogen, nitro, amino, formyl, cyano, C$_1$-C$_6$-alkylamino, C$_1$-C$_6$-haloalkylamino, di-(C$_1$-C$_6$-alkyl)amino, C$_1$-C$_6$-alkyl, C$_1$-C$_6$-haloalkyl, optionally halogen-, cyano-, C$_1$-C$_6$-alkyl-, C$_1$-C$_6$-haloalkyl- and C$_1$-C$_6$-alkoxy-substituted C$_3$-C$_6$-cycloalkyl, optionally halogen-, cyano-, C$_1$-C$_6$-alkyl-, C$_1$-C$_6$-haloalkyl- and C$_1$-C$_6$-alkoxy-substituted C$_3$-C$_6$-cycloalkenyl, optionally halogen-, cyano-, C$_1$-C$_6$-alkyl-, C$_1$-C$_6$-haloalkyl- and C$_1$-C$_6$-alkoxy-substituted C$_3$-C$_6$-cycloalkyl-C$_1$-C$_6$-alkyl where in the cycloalkyl moiety, if 5- or 6-membered, of the cycloalkylalkyl radical one or two CH$_2$ groups may be replaced by oxygen or sulphur, but two oxygen atoms must not be directly adjacent to one another. C$_1$-C$_6$-alkoxy, C$_1$-C$_6$-haloalkoxy, C$_1$-C$_6$-alkoxy-C$_1$-C$_6$-alkyl, halogenated C$_1$-C$_6$-alkoxy-C$_1$-C$_6$-alkyl, bis(C$_1$-C$_6$-alkoxy)-C$_1$-C$_6$-alkyl, bis(C$_1$-C$_6$-haloalkoxy)-C$_1$-C$_6$-alkyl, C$_1$-C$_6$-alkoxy(C$_1$-C$_6$-alkylsulphanyl)-C$_1$-C$_6$-alkyl, C$_1$-C$_6$-alkoxy(C$_1$-C$_6$-alkylsulphinyl)-C$_1$-C$_6$-alkyl, C$_1$-C$_6$-alkoxy(C$_1$-C$_6$-alkylsulphonyl)-C$_1$-C$_6$-alkyl, bis(C$_1$-C$_6$-alkylsulphanyl)-C$_1$-C$_6$-alkyl, bis(C$_1$-C$_6$-haloalkylsulphanyl)-C$_1$-C$_6$-alkyl, bis(C$_1$-C$_6$-hydroxyalkylsulphanyl)-C$_1$-C$_6$-alkyl, C$_1$-C$_6$-alkoxycarbonyl, C$_1$-C$_6$-alkoxycarbonyl-C$_1$-C$_6$-alkyl, alpha-hydroxyimino-C$_1$-C$_6$-alkoxycarbonylmethyl, alpha-C$_1$-C$_6$-alkoxyimino-C$_1$-C$_6$-alkoxycarbonylmethyl, C(X)N$^5$R$^6$, (in which X represents oxygen, sulphur, N$^{15}$ or NOH, R$^5$ represents hydrogen or C$_1$-C$_6$-alkyl and R$^6$ and R$^{15}$ independently of one another represent a radical from the group consisting of hydrogen, C$_1$-C$_6$-alkyl, C$_1$-C$_6$-haloalkyl, cyano-C$_1$-C$_6$-alkyl, C$_2$-C$_6$-alkynyl, C$_3$-C$_6$-cycloalkyl, C$_3$-C$_6$-cycloalkyl-C$_1$-C$_6$-alkyl, C$_1$-C$_6$-alkylcarbonyl, C$_1$-C$_6$-alkoxy-C$_1$-C$_6$-alkyl, C$_1$-C$_6$-alkoxycarbonyl, C$_1$-C$_6$-alkoxycarbonyl-C$_1$-C$_6$-alkyl, C$_1$-C$_6$-alkylthio-C$_1$-C$_6$-alkyl, phenyl, phenyl-C$_1$-C$_6$-alkyl and hetaryl-C$_1$-C$_6$-alkyl in which hetaryl represents pyrimidyl and R$^6$ may also represent OH or R$^5$ and R$^6$ together with the nitrogen atom to which they are attached form a 5- to 7-membered ring which may contain one further heteroatom from the group consisting of NH, NCH$_3$, NC$_2$H$_5$, oxygen and sulphur or R$^5$ and R$^{15}$ together with the nitrogen atoms to which they are attached form a 5- to 7-membered ring which may contain one or more, in particular one or two, further heteroatoms from the group consisting of NH, NCH$_3$, NC$_2$H$_5$, oxygen and sulphur, where two oxygen atoms must not be directly adjacent to one another), NR$^7$R$^8$ (in which R$^7$ represents hydrogen or C$_1$-C$_6$-alkyl and R$^8$ represents a radical from the group consisting of hydrogen, C$_1$-C$_6$-alkyl, C$_1$-C$_6$-haloalkyl, cyano-C$_1$-C$_6$-alkyl, C$_2$-C$_6$-alkynyl, C$_3$-C$_6$-cycloalkyl, C$_3$-C$_6$-cycloalkyl-C$_1$-C$_6$-alkyl, C$_1$-C$_6$-alkoxy, C$_1$-C$_6$-haloalkoxy, C$_1$-C$_6$-alkoxy-C$_1$-C$_6$-alkyl, C$_1$-C$_6$-alkoxycarbonyl, C$_1$-C$_6$-alkoxycarbonyl-C$_1$-C$_6$-alkyl, C$_1$-C$_6$-alkylthio-C$_1$-C$_6$-alkyl, phenyl, phenyl-C$_1$-C$_6$-alkyl and hetaryl-C$_1$-C$_6$-alkyl in which hetaryl represents pyrimidyl or R$^7$ and R$^8$ together with the nitrogen atom to which they are attached form a 5- to 7-membered ring which may contain one further heteroatom from the group consisting of NH, NCH$_3$, NC$_2$H$_5$, oxygen and sulphur), C$_1$-C$_6$-alkylthio, C$_1$-C$_6$-alkylsulphinyl, C$_1$-C$_6$-alkylsulphonyl, the heterocyclyl radicals C$_3$-C$_8$-cycloalkyl and C$_4$-C$_8$-cycloalkenyl in which one or two CH$_2$ groups are replaced by oxygen or sulphur, where two oxygen atoms must not be directly adjacent to one another, in particular dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide (where in these heterocyclyl radicals two hydrogen atoms attached to the same carbon atom may be replaced by $=CH_2$, $-CH_2-CH_2-$, $-CH_2-CH_2-CH_2-$ or $-CH_2-CH_2-CH_2-CH_2-$), morpholinyl, triazolinonyl, oxazolinyl, dihydrooxadiazinyl, dihydrodioxazinyl, dihydrooxazolyl, dihydrooxazinyl and pyrazolinonyl (in particular 1,3-dioxolan-2-yl, 1,3-dioxan-2-yl, 1,3-dioxepan-2-yl, 1,3-dioxocan-2-yl, 1,3-oxathian-2-yl, 1,3-oxathiolan-2-yl, 1,3-oxathiepan-2-yl, 1,3-oxathiocan-2-yl, 1,3-dithian-2-yl, 1,3-dithiolan-2-yl, 1,3-dithiepan-2-yl, 1,3-dithiocan-2-yl, 4,5-dihydro-1,3-oxazol-2-yl, 5,6-dihydro-4H-1,3-oxazin-2-yl, 1,3-oxathianyl 3-oxide, 1,3-oxathiolanyl 3-oxide, 1,3-oxathiepanyl 3-oxide, 1,3-oxathiocanyl 3-oxide, 1,3-oxathianyl 3,3-dioxide, 1,3-oxathiolanyl 3,3-dioxide, 1,3-oxathiepanyl 3,3-dioxide, 1,3-oxathiocanyl 3,3-dioxide (where in these heterocyclyl radicals two hydrogen atoms attached to the same carbon atom may be replaced by $=CH_2$, $-CH_2-CH_2-$, $-CH_2-CH_2-CH_2-$ or $-CH_2CH_2-CH_2-CH_2-$) and 1,2,4-triazolin-3-on-2-yl) (where all heterocyclyl radicals for their part may be substituted by $C_1$-$C_6$-alkyl, $C_1$-$C_6$-haloalkyl, $C_1$-$C_6$-alkoxy and $C_1$-$C_6$-alkoxy-$C_1$-$C_6$-alkyl), phenyl (which for its part may be substituted by halogen, cyano, nitro, $C_1$-$C_6$-alkyl and $C_1$-$C_6$-haloalkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (in particular pyrid-2-yl, pyrimid-2-yl, pyrimid-4-yl, pyrazol-1-yl, pyrazol-3-yl, pyrazol-5-yl, 1,2,4-oxadiazol-3-yl, 1,2,4-triazol-3-yl, 1,2,3-triazol-1-yl, 1,2,3-triazol-2-yl, 1,2,4-thiadiazol-3-yl and 1,2,4-triazin-3-yl) (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl and $C_3$-$C_6$-cycloalkyl) and the heteroarylalkyl radicals triazolyl-$C_1$-$C_6$-alkyl, pyridyl-$C_1$-$C_6$-alkyl, pyrimidyl-$C_1$-$C_6$-alkyl and oxadiazolyl-$C_1$-$C_6$-alkyl (which for their part may be substituted by halogen and $C_1$-$C_6$-alkyl) and c represents a number from the group consisting of 0, 1, 2 and 3.

Very particular preference is given to using compounds of the formula (I) in which $G^1$ represents N, CH, C-halogen, C-nitro, C-cyano, C—($C_1$-$C_4$)-alkyl, C—($C_1$-$C_4$)-haloalkyl, C—($C_3$-$C_6$)-cycloalkyl, C—($C_1$-$C_4$)-alkoxy, C—($C_1$-$C_4$)-haloalkoxy, in particular N, CH, C-halogen, C-cyano or C-trifluoromethyl, $R^1$ represents hydrogen, $C_1$-$C_4$-alkyl, $C_1$-$C_4$-haloalkyl, $C_3$-$C_6$-cycloalkyl, halogen, cyano, $C_1$-$C_4$-alkoxy, $C_1$-$C_4$-haloalkoxy, amino, $C_1$-$C_4$-alkylamino, di-($C_1$-$C_4$)-alkylamino or $C_1$-$C_4$-alkylthio, in particular hydrogen and methyl, and $G^2$ represents $A-R^2_a$, $D-R^3_b$ or $E-R^4_c$, in which A represents heterocyclyl from the group consisting of oxazolin-2-yl, 5,6-dihydro-[1,3,4]-oxadiazin-2-yl, 5,6-dihydro-[1,3,4]-thiadiazin-2-yl and 5,6-dihydro-[1,4,2]-dioxazin-3-yl, $R^2$ represents a radical from the group consisting of halogen, cyano, nitro, $C_1$-$C_4$-alkyl, $C_1$-$C_4$-haloalkyl, optionally fluorine-, chlorine-, cyano-, methyl-, methoxy- and trifluoromethyl-substituted $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-alkylsulphonyl, $C_1$-$C_4$-haloalkylsulphinyl, $C_1$-$C_4$-haloalkylsulphonyl, amino, $C_1$-$C_4$-alkylamino, di-($C_1$-$C_4$-alkyl)amino, $C_1$-$C_4$-alkylcarbonylamino, $C_1$-$C_4$-alkoxycarbonylamino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-alkynyl, optionally fluorine-, chlorine-, cyano-, methyl-, methoxy- and trifluoromethyl-substituted $C_3$-$C_6$-cycloalkyl-$C_1$-$C_4$-alkyl, $C_1$-$C_4$-alkylcarbonyl, $C_1$-$C_4$-alkoxycarbonyl, aminocarbonyl, pyridyl and pyrimidyl (where pyridyl and pyrimidyl for their part may be substituted by halogen, $C_1$-$C_4$-alkyl, $C_1$-$C_4$-haloalkyl, $C_1$-$C_4$-alkoxy and $C_1$-$C_4$-haloalkoxy), a represents a number from the group consisting of 0, 1, 2 and 3, D represents a heteroaryl radical from the group consisting of pyrid-2-yl, pyrid-3-yl, pyrimid-2-yl, pyrimid-4-yl, imidazolyl, pyrazol-1-yl, pyrazol-3-yl pyrazinyl, 1,2,3-triazinyl, 1,2,4-triazinyl, 1,3,5-triazinyl, thiazol-2-yl, thiazol-4-yl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl and oxazolyl (in particular pyrazol-1-yl, pyrazol-3-yl, pyrid-2-yl, pyrid-3-yl, pyrimid-2-yl, pyrimid-4-yl, thiazol-2-yl and thiazol-4-yl), $R^3$ represents a radical from the group consisting of halogen, nitro, amino, formyl, cyano, $C_1$-$C_4$-alkylamino, $C_1$-$C_4$-haloalkylamino, di-($C_1$-$C_4$-alkyl)amino, $C_1$-$C_4$-alkyl, $C_1$-$C_4$-haloalkyl, optionally fluorine-, chlorine-, cyano-, methyl-, methoxy- and trifluoromethyl-substituted $C_3$-$C_6$-cycloalkyl, optionally fluorine-, chlorine-, cyano-, methyl-, methoxy- and trifluoromethyl-substituted $C_3$-$C_6$-cycloalkenyl, optionally fluorine-, chlorine-, cyano-, methyl-, methoxy- and trifluoromethyl-substituted $C_3$-$C_6$-cycloalkyl-$C_1$-$C_4$-alkyl where in the cycloalkyl moiety, if 5- or 6-membered, of the cycloalkylalkyl radical one or two $CH_2$ groups may be replaced by oxygen or sulphur, but two oxygen atoms must not be directly adjacent to one another, $C_1$-$C_4$-alkoxy, $C_1$-$C_4$-haloalkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, bis($C_1$-$C_4$-haloalkoxy)-$C_1$-$C_4$-alkyl, $C_1$-$C_4$-alkoxy($C_1$-$C_4$-alkylsulphanyl)-$C_1$-$C_4$-alkyl, $C_1$-$C_4$-alkoxy($C_1$-$C_4$-alkylsulphinyl)-$C_1$-$C_4$-alkyl, $C_1$-$C_4$-alkoxy($C_1$-$C_4$-alkylsulphonyl)-$C_1$-$C_4$-alkyl, bis($C_1$-$C_4$-alkylsulphanyl)-$C_1$-$C_4$-alkyl, bis($C_1$-$C_4$-haloalkylsulphanyl)-$C_1$-$C_4$-alkyl, bis($C_1$-$C_4$-hydroxyalkylsulphanyl)-$C_1$-$C_4$-alkyl, $C_1$-$C_4$-alkoxycarbonyl, $C_1$-$C_4$-alkoxycarbonyl-$C_1$-$C_4$-alkyl, alpha-hydroxyimino-$C_1$-$C_4$-alkoxycarbonylmethyl, alpha-$C_1$-$C_4$-alkoxyimino-$C_1$-$C_4$-alkoxycarbonylmethyl, $C(X)NR^5R^6$, (in which X represents oxygen, $NR^{15}$ or sulphur, $R^5$ represents hydrogen or $C_1$-$C_4$-alkyl and $R^6$ and $R^{15}$ independently of one another represent a radical from the group consisting of hydrogen, $C_1$-$C_5$-alkyl, $C_1$-$C_4$-haloalkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkylthio-$C_1$-$C_4$-alkyl and phenyl-$C_1$-$C_4$-alkyl and $R^6$ may also represent OH or $R^5$ and $R^6$ together with the nitrogen atom to which they are attached form a 5- or 6-membered ring which may contain one further heteroatom from the group consisting of oxygen, sulphur, NH, $NCH_3$ and $NC_2H_5$ or $R^5$ and $R^{15}$ together with the nitrogen atoms to which they are attached form a 5- or 6-membered ring which may contain one or two further heteroatoms from the group consisting of NH, $NCH_3$, $NC_2H_5$, oxygen and sulphur, where two oxygen atoms must not be directly adjacent to one another), $NR^7R^8$ (in which $R^7$ represents hydrogen or $C_1$-$C_4$-alkyl and $R^8$ represents a radical from the group consisting of hydrogen, $C_1$-$C_5$-alkyl, $C_1$-$C_4$-haloalkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy, $C_1$-$C_4$-haloalkoxy, $C_1$-$C_4$-alkoxycarbonyl, $C_1$-$C_4$-alkoxycarbonyl-$C_1$-$C_4$-alkyl, $C_1$-$C_4$-alkoxy-$C_1$-$C_4$-alkyl, $C_1$-$C_4$-alkylthio-$C_1$-$C_4$-alkyl and phenyl-$C_1$-$C_4$-alkyl or $R^7$ and $R^8$ together with the nitrogen atom to which they are attached form a 5- or 6-membered ring which may contain one further heteroatom from the group consisting of oxygen, sulphur, NH, $NCH_3$ and $NC_2H_5$), $C_1$-$C_4$-alkylthio, $C_1$-$C_4$-alkylsulphinyl, $C_1$-$C_4$-alkylsulphonyl, the heterocyclyl radicals dioxanyl, dioxolanyl, dioxepanyl, oxathianyl, oxathiolanyl, oxathiepanyl, dithianyl, dithiolanyl, dithiepanyl, oxathianyl oxide, oxathiolanyl oxide, oxathiepanyl oxide, oxathianyl dioxide, oxathiolanyl dioxide, oxathiepanyl dioxide, (where in these heterocyclyl radicals two hydrogen atoms attached to the same carbon atom may be replaced by $=CH_2$, $-CH_2-CH_2-$, $-CH_2-CH_2-CH_2-$ or $-CH_2-CH_2-CH_2-CH_2-$) morpholinyl, triazolinonyl, oxazolinyl, dihydrooxadiazinyl, dihydrodioxazinyl, dihydrooxazolyl, dihydrooxazinyl and pyrazolinonyl (in particular 1,3-dioxolan-2-yl, 1,3-dioxan-2-yl, 1,3-dioxepan-2-yl, 1,3-oxathian-2-yl, 1,3-oxathiolan-2-yl, 1,3-oxathiepan-2-yl, 1,3-dithian-2-yl, 1,3-dithiolan-2-yl, 1,3-dithiepan-2-yl, 4,5-dihydro-1,3-oxazol-2-yl, 5,6-dihydro-4H-1,3-oxazin-2-yl, 1,3-oxathianyl 3-oxide, 1,3-oxathiolanyl 3-oxide, 1,3-oxathiepanyl 3-oxide, 1,3-oxathianyl 3,3-dioxide, 1,3-oxathiolanyl 3,3-dioxide, 1,3-oxathiepanyl 3,3-dioxide (where in these heterocyclyl radicals two hydrogen atoms attached to the same carbon atom may be replaced by $=CH_2$, $-CH_2-CH_2-$, $-CH_2-CH_2-CH_2-$ or $-CH_2-CH_2-CH_2-CH_2-$)) and 1,2,4-triazolin-3-on-2-yl) (where all heterocyclyl radicals for their part may be substituted by $C_1$-$C_4$-alkyl, $C_1$-$C_4$-haloalkyl and $C_1$-$C_4$-alkoxy-$C_1$-$C_4$-alkyl), phenyl (which for its part may be substituted by halogen, cyano, nitro, $C_1$-$C_4$-alkyl and $C_1$-$C_4$-haloalkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (in particular pyrid-2-yl, pyrimid-2-yl, pyrimid-4-yl, pyrazol-1-yl, pyrazol-3-yl, pyrazol-5-yl, 1,2,4-oxadiazol-3-yl, 1,2,4-triazol-3-yl, 1,2,3-triazol-1-yl, 1,2,3-triazol-2-yl, 1,2,4-thiadiazol-3-yl, tetrazolyl and 1,2,4-triazin-3-yl) (which for their part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cycloalkyl) and the heteroarylalkyl radicals triazolyl-$C_1$-$C_4$-alkyl, pyridyl-$C_1$-$C_4$-alkyl, pyrimidyl-$C_1$-$C_4$-alkyl or oxadiazolyl-$C_1$-$C_4$-alkyl (which for their part may be substituted by halogen and $C_1$-$C_4$-alkyl), b represents a number from the group consisting of 0, 1, and 2, E represents phenyl and $R^4$ represents a radical from the group consisting of halogen, cyano, $C_1$-$C_4$-alkyl, $C_1$-$C_4$-haloalkyl, $C_1$-$C_4$-alkoxy and $C_1$-$C_4$-haloalkoxy and c represents a number from the group consisting of 0, 1 and 2.

Very particular emphasis is given to using compounds of the formula (I) in which $G^1$ represents N, CH, C-halogen, C-cyano, C—$CH_3$, C—$CF_3$, C-cyclopropyl, C—$OCH_3$, C—$OCF_3$, in particular N, CH, C-halogen, $R^1$ represents hydrogen, methyl, trifluoromethyl, cyclopropyl, halogen, cyano, methoxy, trifluoromethoxy, amino, methylamino, dimethylamino, in particular hydrogen, $G^2$ represents A-$R^2_a$ or D-$R^3_b$ in which A represents heterocyclyl from the group consisting of oxazolin-2-yl, 5,6-dihydro-[1,3,4]-oxadiazin-2-yl and 5,6-dihydro-[1,3,4]-thiadiazin-2-yl, $R^2$ represents a radical from the group consisting of pyridyl and pyrimidin-2-yl which may be substituted by halogen, $C_1$-$C_4$-alkyl, $C_1$-$C_4$-haloalkyl, $C_1$-$C_4$-alkoxy and $C_1$-$C_4$-haloalkoxy, a represents 0, 1 or 2 and in particular represents 1, D represents a heteroaryl radical from the group consisting of pyrazol-1-yl, pyrazol-3-yl, pyrid-2-yl, pyrid-3-yl, pyrimid-2-yl, pyrimid-4-yl, thiazol-2-yl and thiazol-4-yl, $R^3$ represents a radical from the group consisting of halogen (in particular chlorine, bromine), nitro, amino, formyl, cyano, $C_1$-$C_4$-haloalkyl (in particular $CF_3$, $CF_3CH_2$, $CH_3CF_2$, $CF_3CF_2$, $CF_2C$, $CF_3CF_2CF_2$, $CH_3CHF$), optionally fluorine-, chlorine-, cyano-, methyl-, methoxy- and trifluoromethyl-substituted $C_3$-$C_6$-cycloalkyl, optionally fluorine-, chlorine-, cyano-, methyl-, methoxy- and trifluoromethyl-substituted $C_5$-$C_6$-cycloalkenyl, optionally fluorine-, chlorine-, cyano-, methyl-, methoxy- and trifluoromethyl-substituted $C_3$-$C_6$-cycloalkyl-$C_1$-$C_2$-alkyl (in particular cyclopropylmethyl) where in the cycloalkyl moiety, if 5- or 6-membered, of the cycloalkylalkyl radical one or two $CH_2$ groups may be replaced by oxygen or sulphur, but two oxygen atoms must not be directly adjacent to one another, $C_1$-$C_4$-alkoxy (in particular methoxy), $C_1$-$C_4$-haloalkoxy (in particular $CF_3CH_2O$), $C_1$-$C_4$-alkoxy-$C_1$-$C_4$-alkyl (in particular methoxymethyl), halogenated $C_1$-$C_4$-alkoxy-$C_1$-$C_4$-alkyl (in particular $CF_2CH_2OCH_3$), bis($C_1$-$C_4$-alkoxy)-$C_1$-$C_4$-alkyl (in particular $(CH_3O)_2CH$), $C_1$-$C_4$-alkoxy($C_1$-$C_4$-alkylsulphanyl)-$C_1$-$C_4$-alkyl (in particular $CH_3OC(H)SCH_3$), bis($C_1$-$C_4$-alkylsulphanyl)-$C_1$-$C_4$-alkyl (in particular $(CH_3S)_2CH$), $C_1$-$C_4$-alkoxycarbonyl (in particular methoxycarbonyl), alpha-hydroxyimino-$C_1$-$C_4$-alkoxycarbonylmethyl, $C(X)NR^5R^6$, (in which X represents oxygen or sulphur, $R^5$ represents hydrogen or $C_1$-$C_4$-alkyl (in particular methyl) and $R^6$ represents a radical from the group consisting of $C_1$-$C_5$-alkyl (in particular methyl, ethyl, n-propyl, isopropyl, isobutyl, tert-butyl), $C_1$-$C_4$-haloalkyl (in particular $CF_3CH_2$), cyano-$C_1$-$C_4$-alkyl (in particular $NCCH_2CH(C_2H_5)$), $C_3$-$C_6$-cycloalkyl (in particular cyclopropyl, cyclopentyl, cyclohexyl), $C_3$-$C_6$-cycloalkyl-$C_1$-$C_4$-alkyl (in particular cyclopropylmethyl), $C_1$-$C_4$-alkoxy-$C_1$-$C_4$-alkyl (in particular $CH_3OCH_2CH(CH_3)$, $CH_3CH_2CH_2OCH_2CH(CH_3)$, $CH_3CH_2OCH_2CH_2$, $CH_3OCH_2CH_2CH_2$, $CH_3OCH_2CHC_2H_5$, $CH_3CH_2OCH_2CH(CH_3)$, $CH_3CH_2OCH_2CH_2H_2$, $CH_3OC(CH_3)_2$), $C_1$-$C_4$-alkylthio-$C_1$-$C_4$-alkyl (in particular $CH_3SCH_2CH_2$) and phenyl-$C_1$-$C_4$-alkyl (in particular $C_6H_5CH(CH_3)$ or $R^5$ and $R^6$ together with the nitrogen atom to which they are attached form a 5- or 6-membered ring which may contain one further heteroatom from the group consisting of oxygen, sulphur, NH, $NCH_3$, and $NC_2H_5$ (in particular, $R^5$ and $R^6$ together represent $(CH_2)_4$, $(CH_2)_5$ or $(CH_2)_2O(CH_2)_2$), $NR^7R^8$ (in which $R^7$ represents hydrogen or methyl and $R^8$ represents a radical from the group consisting of hydrogen, $C_1$-$C_4$-alkyl (in particular methyl and ethyl), $C_1$-$C_4$-haloalkyl (in particular $CH_2CF_3$ and $CH_2CF_2H$), $C_1$-$C_4$-alkoxy (in particular $OCH_3$), $C_1$-$C_4$-alkylcarbonyl (in particular $COCH_3$), $C_1$-$C_4$-alkoxycarbonyl (in particular $CO_2CH_3$, $CO_2CH_2CH_3$ and $CO_2C(CH_3)_3$) and $C_1$-$C_4$-alkoxycarbonyl-$C_1$-$C_4$-alkyl (in particular $CH_2CO_2CH_3$) or $R^7$ and $R^8$ together with the nitrogen atom to which they are attached form a 5- or 6-membered ring which may contain an oxygen atom (in particular, $R^7$ and $R^8$ together represent $(CH_2)_4$, $(CH_2)_5$ or $(CH_2)_2O(CH_2)_2$), $C_1$-$C_4$-alkylthio (in particular methylthio), $C_1$-$C_4$-alkylsulphonyl (in particular $CH_3SO_2$), the heterocyclyl radicals dioxanyl, dioxolanyl, oxathianyl, oxathiolanyl, dithianyl, dithiolanyl, oxathianyl oxide, oxathiolanyl oxide, oxathianyl dioxide, oxathiolanyl dioxide (where in these heterocyclyl radicals two hydrogen atoms attached to the same carbon atom may be replaced by =$CH_2$, —$CH_2$—$CH_2$—, —$CH_2$—$CH_2$—$CH_2$— or —$CH_2$—$CH_2$—$CH_2$—$CH_2$—), morpholinyl, triazolinonyl, oxazolinyl, dihydrooxadiazinyl, dihydrodioxazinyl, dihydrooxazolyl, dihydrooxazinyl and pyrazolinonyl (in particular 1,3-dioxolan-2-yl, 1,3-dioxan-2-yl, 1,3-oxathian-2-yl, 1,3-oxathiolan-2-yl, 1,3-dithian-2-yl, 1,3-dithiolan-2-yl, 4,5-dihydro-1,3-oxazol-2-yl, 5,6-dihydro-4H-1,3-oxazin-2-yl, 1,3-oxathianyl 3-oxide, 1,3-oxathiolanyl 3-oxide, 1,3-oxathianyl 3,3-dioxide, 1,3-oxathiolanyl 3,3-dioxide (where in these heterocyclyl radicals two hydrogen atoms attached to the same carbon atom may be replaced by =$CH_2$, —$CH_2$—$CH_2$—, —$CH_2$—$CH_2$—$CH_2$— or —$CH_2$—$CH_2$—$CH_2CH_2$—), and 1,2,4-triazolin-3-on-2-yl) (where all heterocyclyl radicals for their part may be substituted by $C_1$-$C_4$-alkyl (in particular methyl), $C_1$-$C_4$-haloalkyl (in particular $CF_3$) and $C_1$-$C_4$-alkoxy-$C_1$-$C_4$-alkyl (in particular methoxymethyl)), phenyl (which for its part may be substituted by halogen (in particular fluorine, chlorine), the heteroaryl radicals pyridyl, pyridyl N-oxide, pyrimidinyl, pyrazolyl, thiazolyl, furanyl, thienyl, triazolyl, tetrazolyl, oxadiazolyl, thiadiazolyl, pyrazinyl, triazinyl, and isoquinolinyl (in particular pyrid-2-yl, pyrimid-2-yl, pyrimid-4-yl, pyrazol-1-yl, pyrazol-3-yl, pyrazol-5-yl, 1,2,4-oxadiazol-3-yl, 1,2,4-triazol-3-yl, 1,2,3-triazol-1-yl, 1,2,3-triazol-2-yl, 1,2,4-thiadiazol-3-yl, tetrazolyl and 1,2,4-triazin-3-yl) (which for their part may be substituted by halogen (in particular fluorine and chlorine), nitro, $C_1$-$C_4$-alkyl (in particular methyl, ethyl, n-propyl, isopropyl and tert-butyl), $C_1$-$C_4$-haloalkyl (in particular $CF_3$, $CHF_2$ and $CF_2Cl$), $C_1$-$C_4$-alkoxy (in particular methoxy, ethoxy) and $C_3$-$C_6$-cycloalkyl (in particular cyclopropyl, cyclobutyl, cyclopentyl)), the heteroarylalkyl radicals triazolyl-$C_1$-$C_4$-alkyl (in particular triazolylmethyl), pyridyl-$C_1$-$C_4$-alkyl (in particular pyridylmethyl), pyrimidinyl-$C_1$-$C_4$-alkyl (in particular pyrimidinylmethyl) or oxadiazolyl-$C_1$-$C_4$-alkyl (in particular oxadiazolylmethyl (which for their part may be substituted by $C_1$-$C_4$-alkyl (in particular methyl)) and b represents 0, 1 or 2 and in particular represents 1.

The invention also relates to the use of compounds of the formula (I) for controlling animal pests in which $G^1$ represents N, CH or C-halogen, $R^1$ represents hydrogen or alkyl and $G^2$ represents optionally substituted heterocyclyl, represents optionally substituted heteroaryl or represents optionally substituted aryl, and also salts, metal complexes and N-oxides of the compounds of the formula (I).

Preference is also given to using compounds of the formula (I) in which $G^1$ represents N, CH or C-halogen, $R^1$ represents hydrogen or alkyl, $G^2$ represents A-$R^2{}_a$, D-$R^3{}_b$ or E-$R^4{}_c$ in which A represents heterocyclyl from the group consisting of 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, oxazolin-2-yl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 5,6-dihydro-[1,3,4]-oxadiazin-2-yl, 5,6-dihydro-[1,3,4]-thiadiazin-2-yl, 5,6-dihydro-[1,4,2]-dioxazin-3-yl, hydroxypyridyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,3-dihydrothien-2-yl, 2,3-dihydrothien-3-yl, 2,4-dihydrothien-2-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, $R^2$ represents a radical from the group consisting of halogen, cyano, nitro, alkyl, haloalkyl, cycloalkyl, alkoxy, haloalkoxy, alkylthio, haloalkylthio, alkylsulphinyl, alkylsulphonyl, haloalkylsulphinyl, haloalkylsulphonyl, amino, alkylamino, dialkylamino, alkylcarbonylamino, alkoxycarbonylamino, alkoxyalkyl, haloalkoxyalkyl, alkenyl, alkynyl, cycloalkylalkyl, alkylcarbonyl, alkoxycarbonyl, aminocarbonyl, pyridyl and pyrimidyl (where pyridyl and pyrimidyl for their part may be substituted by halogen, alkyl, haloalkyl, alkoxy and haloalkoxy), a represents a number from the group consisting of 0, 1, 2 and 3, D represents a heteroaryl radical from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyrid-2-yl, pyrid-3-yl, pyrimid-2-yl, pyrimid-4-yl, imidazolyl, pyrazol-1-yl, pyrazol-3-yl pyrazolyl, 1,2,3-triazinyl, 1,2,4-triazinyl, 1,3,5-triazinyl, thiazol-2-yl, thiazol-4-yl 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl and oxazolyl), $R^3$ represents a radical from the group consisting of halogen, nitro, amino, cyano, alkylamino, haloalkylamino, dialkylamino, alkyl, haloalkyl, cycloalkylalkyl, alkoxy, haloalkoxy, alkoxyalkyl, halogenated alkoxyalkyl, bis(alkoxy)alkyl, alkoxycarbonyl, alkoxycarbonylalkyl, alpha-hydroxyimino-alkoxycarbonylalkyl, alpha-alkoxyimino-alkokycarbonylalkyl, $C(X)NR^5R^6$ (in which X represents oxygen, sulphur or NOH, $R^5$ represents hydrogen or alkyl and $R^6$ represents a radical from the group consisting of hydrogen, alkyl, haloalkyl, cyanoalkyl, alkynyl, cycloalkyl, cycloalkylalkyl, alkoxyalkyl, alkoxycarbonyl, alkoxycarbonylalkyl, alkylthioalkyl, aryl, arylalkyl and hetarylalkyl or $R^5$ and $R^6$ together with the nitrogen atom to which they are attached form a ring which may contain one or more further heteroatoms from the group consisting of nitrogen, oxygen and sulphur), $NR^7R^8$ (in which $R^7$ represents hydrogen or alkyl and $R^8$ represents a radical from the group consisting of hydrogen, alkyl, haloalkyl, cyanoalkyl, alkynyl, cycloalkyl, cycloalkylalkyl, alkoxy, haloalkoxy, alkoxyalkyl, alkoxycarbonyl, alkoxycarbonylalkyl, alkylthioalkyl, aryl, arylalkyl or hetarylalkyl or $R^7$ and $R^8$ together with the nitrogen atom to which they are attached form a ring which may contain one or more further heteroatoms from the group consisting of nitrogen, oxygen and sulphur), alkylthio, alkylsulphinyl, alkylsulphonyl, the heterocyclyl radicals dioxanyl, dioxolanyl, morpholinyl, triazolinonyl, oxazolinyl, dihydrooxadiazinyl, dihydrodioxazinyl and pyrazolinonyl (which for their part may be substituted by alkyl, haloalkyl, alkoxy and alkoxyalkyl), phenyl (which for its part may be substituted by halogen, cyano, nitro, alkyl and haloalkyl), the heteroaryl radicals pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl and cycloalkyl) and the heteroarylalkyl radicals triazolylalkyl, pyridylalkyl, pyrimidylalkyl and oxadiazolylalkyl (which for their part may be substituted by halogen and alkyl), b represents a number from the group consisting of 0, 1, 2 and 3, E represents aryl, in particular phenyl, $R^4$ represents a radical from the group consisting of halogen, cyano, alkyl, haloalkyl, alkoxy, haloalkoxy, dioxolanyl or dihydrodioxazinyl and c represents a number from the group consisting of 0, 1, 2 and 3.

Particular preference is also given to using compounds of the formula (I) in which $G^1$ represents N, CH or C-halogen, $R^1$ represents hydrogen or $C_1$-$C_6$-alkyl and $G^2$ represents $A$-$R^2_a$, $D$-$R^3_b$ or $E$-$R^4_c$ in which A represents heterocyclyl from the group consisting of oxazolin-2-yl, 5,6-dihydro-[1,3,4]-oxadiazin-2-yl, 5,6-dihydro-[1,3,4]-thiadiazin-2-yl, 5,6-dihydro-[1,4,2]-dioxazin-3-yl and hydroxypyridyl, $R^2$ represents a radical from the group consisting of halogen, cyano, nitro, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-haloalkylsulphinyl, $C_1$-$C_6$-haloalkylsulphonyl, amino, $C_1$-$C_6$-alkylamino, di-($C_1$-$C_6$-alkyl)amino, $C_1$-$C_6$-alkylcarbonylamino, $C_1$-$C_6$-alkoxycarbonylamino, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-alkynyl, $C_3$-$C_6$-cycloalkyl-$C_1$-$C_6$-alkyl, $C_1$-$C_6$-alkylcarbonyl, $C_1$-$C_6$-alkoxycarbonyl, aminocarbonyl, pyridyl and pyrimidyl (where pyridyl and pyrimidyl for their part may be substituted by halogen, $C_1$-$C_6$-alkyl, $C_1$-$C_6$-haloalkyl, $C_1$-$C_6$-alkoxy and $C_1$-$C_6$-haloalkoxy), a represents a number from the group consisting of 0, 1, 2 and 3, D represents a heteroaryl radical from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyrid-2-yl, pyrid-3-yl, pyrimid-2-yl, pyrimid-4-yl, imidazolyl, pyrazol-1-yl, pyrazol-3-yl pyrazinyl, 1,2,3-triazinyl, 1,2,4-triazinyl, 1,3,5-triazinyl, thiazol-2-yl, thiazol-4-yl 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl and oxazolyl), $R^3$ represents a radical from the group consisting of halogen, nitro, amino, cyano, $C_1$-$C_6$-alkylamino, $C_1$-$C_6$-haloalkylamino, di-($C_1$-$C_6$-alkyl)amino, $C_1$-$C_6$-alkyl, $C_1$-$C_6$-haloalkyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, halogenated $C_1$-$C_6$-alkoxy-$C_1$-$C_6$-alkyl, bis($C_1$-$C_6$-alkoxy)-$C_1$-$C_6$-alkyl, $C_1$-$C_6$-alkoxycarbonyl, alpha-hydroxyimino-$C_1$-$C_6$-alkoxycarbonylmethyl, alpha-$C_1$-$C_6$-alkoxyimino-$C_1$-$C_6$-alkoxycarbonylmethyl, $C(X)NR^5R^6$ (in which X represents oxygen, sulphur or NOH, $R^5$ represents hydrogen or $C_1$-$C_6$-alkyl and $R^6$ represents a radical from the group consisting of hydrogen, $C_1$-$C_6$-alkyl, $C_1$-$C_6$-haloalkyl, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy-$C_1$-$C_6$-alkyl, $C_1$-$C_6$-alkoxycarbonyl, $C_1$-$C_6$-alkoxycarbonyl-$C_1$-$C_6$-alkyl, $C_1$-$C_6$-alkylthio-$C_1$-$C_6$-alkyl, phenyl, phenyl-$C_1$-$C_6$-alkyl and hetaryl-$C_1$-$C_6$-alkyl in which hetaryl represents pyrimidyl or $R^5$ and $R^6$ together with the nitrogen atom to which they are attached form a 5- to 7-membered ring which may contain one further heteroatom from the group consisting of nitrogen, oxygen and sulphur), $NR^7R^8$ (in which $R^7$ represents hydrogen or $C_1$-$C_6$-alkyl and $R^8$ represents a radical from the group consisting of hydrogen, $C_1$-$C_6$-alkyl, $C_1$-$C_6$-haloalkyl, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxycarbonyl, $C_1$-$C_6$-alkoxycarbonyl-$C_1$-$C_6$-alkyl, $C_1$-$C_6$-alkylthio-$C_1$-$C_6$-alkyl, phenyl, phenyl-$C_1$-$C_6$-alkyl and hetaryl-$C_1$-$C_6$-alkyl in which hetaryl represents pyrimidyl or $R^7$ and $R^8$ together with the nitrogen atom to which they are attached form a 5- to 7-membered ring which may contain one further heteroatom from the group consisting of nitrogen, oxygen and sulphur), $C_1$-$C_6$-alkylthio, $C_1$-$C_6$-alkylsulphinyl, $C_1$-$C_6$-alkylsulphonyl, the heterocyclyl radicals dioxanyl, dioxolanyl, morpholinyl, triazolinonyl, oxazolinyl, dihydrooxadiazinyl, dihydrodioxazinyl and pyrazolinonyl (in particular 1,3-dioxolan-2-yl, 1,3-dioxan-2-yl and 1,2,4-triazolin-3-on-2-yl) (which for their part may be substituted by $C_1$-$C_6$-alkyl, $C_1$-$C_6$-haloalkyl, $C_1$-$C_6$-alkoxy and $C_1$-$C_6$-alkoxy-$C_1$-$C_6$-alkyl), phenyl (which for its part may be substituted by halogen, cyano, nitro, $C_1$-$C_6$-alkyl and $C_1$-$C_6$-haloalkyl), the heteroaryl radicals pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (in particular pyrid-2-yl, pyrimid-2-yl, pyrimid-4-yl, pyrazol-1-yl, pyrazol-2-yl, 1,2,4-oxadiazol-3-yl, 1,2,4-triazol-3-yl and 1,2,4-triazin-3-yl) (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl and $C_3$-$C_6$-cycloalkyl) and the heteroarylalkyl radicals triazolyl-$C_1$-$C_6$-alkyl, pyridyl-$C_1$-$C_6$-alkyl, pyrimidyl-$C_1$-$C_6$-alkyl and oxadiazolyl-$C_1$-$C_6$-alkyl (which for their part may be substituted by halogen and $C_1$-$C_6$-alkyl), b represents a number from the group consisting of 1, 2 and 3, E represents phenyl, $R^4$ represents a radical from the group consisting of halogen, cyano, $C_1$-$C_6$-alkyl, $C_1$-$C_6$-haloalkyl, $C_1$-$C_6$-alkoxy, $C_1$-$C_6$-haloalkoxy, dioxolanyl and dihydrodioxazinyl and c represents a number from the group consisting of 0, 1, 2 and 3.

Very particular preference is also given to using compounds of the formula (I) in which $G^1$ represents N, CH or C-halogen, $R^1$ represents hydrogen or methyl (in particular hydrogen) and $G^2$ represents A-$R^2_a$, D-$R^3_b$ or E-$R^4_c$ in which A represents heterocyclyl from the group consisting of oxazolin-2-yl, 5,6-dihydro-[1,3,4]-oxadiazin-2-yl, 5,6-dihydro-[1,3,4]-thiadiazin-2-yl and 5,6-dihydro-[1,4,2]-dioxazin-3-yl, $R^2$ represents a radical from the group consisting of halogen, cyano, nitro, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-alkylsulphonyl, $C_1$-$C_4$-haloalkylsulphinyl, $C_1$-$C_4$-haloalkylsulphonyl, amino, $C_1$-$C_4$-alkylamino, di-($C_1$-$C_4$-alkyl)amino, $C_1$-$C_4$-alkylcarbonylamino, $C_1$-$C_4$-alkoxycarbonylamino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-alkynyl, $C_3$-$C_6$-cycloalkyl $C_1$-$C_4$-alkyl, $C_1$-$C_4$-alkylcarbonyl, $C_1$-$C_4$-alkoxycarbonyl, aminocarbonyl, pyridyl and pyrimidyl (where pyridyl and pyrimidyl for their part may be substituted by halogen, $C_1$-$C_4$-alkyl, $C_1$-$C_4$-haloalkyl, $C_1$-$C_4$-alkoxy and $C_1$-$C_4$-haloalkoxy), a represents a number from the group consisting of 0, 1, 2 and 3, D represents a heteroaryl radical from the group consisting of pyrid-2-yl, pyrid-3-yl, pyrimid-2-yl, pyrimid-4-yl, imidazolyl, pyrazol-1-yl, pyrazol-3-yl pyrazinyl, 1,2,3-triazinyl, 1,2,4-triazinyl, 1,3,5-triazinyl, thiazol-2-yl, thiazol-4-yl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl and oxazolyl (in particular pyrazol-1-yl, pyrazol-3-yl, pyrid-2-yl, pyrid-3-yl, pyrimid-2-yl, pyrimid-4-yl, thiazol-2-yl and thiazol-4-yl), $R^3$ represents a radical from the group consisting of halogen, nitro, amino, cyano, $C_1$-$C_4$-alkylamino, $C_1$-$C_4$-haloalkylamino, di-($C_1$-$C_4$-alkyl)amino, $C_1$-$C_4$-alkyl, $C_1$-$C_4$-haloalkyl, $C_3$-$C_6$-cycloalkyl-$C_1$-$C_4$-alkyl, $C_1$-$C_4$-alkoxy, $C_1$-$C_4$-haloalkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, $C_1$-$C_4$-alkoxycarbonyl, alpha-hydroxyimino-$C_1$-$C_4$-alkoxycarbonylmethyl, alpha-$C_1$-$C_4$-alkoxyimino-$C_1$-$C_4$-alkoxycarbonylmethyl, C(X)N$R^5R^6$, (in which X represents oxygen or sulphur, $R^5$ represents hydrogen or $C_1$-$C_4$-alkyl and $R^6$ represents a radical from the group consisting of hydrogen, $C_1$-$C_5$-alkyl, $C_1$-$C_4$-haloalkyl, cyano-$C_1$-$C_4$-alkyl, $C_2$-$C_4$-alkynyl, $C_3$-$C_6$-cycloalkyl, $C_1$-$C_6$-cycloalkyl-$C_1$-$C_4$-alkyl, $C_1$-$C_4$-alkoxy-$C_1$-$C_4$-alkyl, $C_1$-$C_4$-alkylthio-$C_1$-$C_4$-alkyl and phenyl-$C_1$-$C_4$-alkyl or $R^5$ and $R^6$ together with the nitrogen atom to which they are attached form a 5- or 6-membered ring which may contain one further heteroatom from the group consisting of oxygen, sulphur and nitrogen), N$R^7R^8$ (in which $R^7$ represents hydrogen or $C_1$-$C_4$-alkyl and $R^8$ represents a radical from the group consisting of hydrogen, $C_1$-$C_5$-alkyl, $C_1$-$C_4$-haloalkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy, $C_1$-$C_4$-haloalkoxy, $C_1$-$C_4$-alkoxycarbonyl, $C_1$-$C_4$-alkoxycarbonyl-$C_1$-$C_4$-alkyl, $C_1$-$C_4$-alkoxy-$C_1$-$C_4$-alkyl, $C_1$-$C_4$-alkylthio-$C_1$-$C_4$-alkyl or phenyl-$C_1$-$C_4$-alkyl or $R^7$ and $R^8$ together with the nitrogen atom to which they are attached form a 5- or 6-membered ring which may contain one further heteroatom from the group consisting of oxygen, sulphur and nitrogen), $C_1$-$C_4$-alkylthio, $C_1$-$C_4$-alkylsulphinyl, $C_1$-$C_4$-alkylsulphonyl, the heterocyclyl radicals dioxanyl, dioxolanyl, morpholinyl, triazolinonyl, oxazolinyl, dihydrooxadiazinyl, dihydrodioxazinyl and pyrazolinonyl (in particular 1,3-dioxolan-2-yl, 1,3-dioxan-2-yl and 1,2,4-triazolin-3-on-2-yl) (which for their part may be substituted by $C_1$-$C_4$-alkyl, $C_1$-$C_4$-haloalkyl and $C_1$-$C_4$-alkoxy-$C_1$-$C_4$-alkyl), phenyl (which for its part may be substituted by halogen, cyano, nitro, $C_1$-$C_4$-alkyl and $C_1$-$C_4$-haloalkyl), the heteroaryl radicals pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (in particular pyrid-2-yl, pyrimid-2-yl, pyrimid-4-yl, pyrazol-1-yl, pyrazol-2-yl, 1,2,4-oxadiazol-3-yl, 1,2,4-triazol-3-yl and 1,2,4-triazin-3-yl) (which for their part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cycloalkyl) and the heteroarylalkyl radicals triazolyl-$C_1$-$C_4$-alkyl, pyridyl-$C_1$-$C_4$-alkyl, pyrimidyl-$C_1$-$C_4$-alkyl or oxadiazolyl-$C_1$-$C_4$-alkyl (which for their part may be substituted by halogen and $C_1$-$C_4$-alkyl), b represents a number from the group consisting of 1, and 2, E represents phenyl and $R^4$ represents a radical from the group consisting of halogen, cyano, $C_1$-$C_4$-alkyl, $C_1$-$C_4$-haloalkyl, $C_1$-$C_4$-alkoxy and $C_1$-$C_4$-haloalkoxy and c represents a number from the group consisting of 0, 1, and 2.

Very particular emphasis is also given to using compounds of the formula (I) in which $G^1$ represents N, CH or C-halogen (in the case of C-halogen in particular C—F), $R^1$ represents hydrogen or methyl (in particular hydrogen), $G^2$ represents A-$R^2_a$ or D-$R^3_b$ in which A represents heterocyclyl from the group consisting of oxazolin-2-yl, 5,6-dihydro-[1,3,4]-oxadiazin-2-yl and 5,6-dihydro-[1,3,4]-thiadiazin-2-yl, $R^2$ represents a radical from the group consisting of pyridyl and pyrimidin-2-yl which may be substituted by halogen, $C_1$-$C_4$-alkyl, $C_1$-$C_4$-haloalkyl, $C_1$-$C_4$-alkoxy and $C_1$-$C_4$-haloalkoxy, a represents 0, 1 or 2 and in particular represents 1, D represents a heteroaryl radical from the group consisting of pyrazol-1-yl, pyrazol-3-yl, pyrid-2-yl, pyrid-3-yl, pyrimid-2-yl, pyrimid-4-yl, thiazol-2-yl and thiazol-4-yl, $R^3$ represents a radical from the group consisting of halogen (in particular chlorine, bromine), nitro, amino, cyano, $C_1$-$C_4$-haloalkyl (in particular $CF_3$, $CF_3CH_2$, $CH_3CF_2$, $CF_3CF_2$, $CF_2Cl$, $CF_3CF_2CF_2$, $CH_3CHF$), $C_3$-$C_6$-cycloalkyl-$C_1$-$C_4$-alkyl (in particular cyclopropylmethyl), $C_1$-$C_4$-alkoxy (in particular methoxy), $C_1$-$C_4$-haloalkoxy (in particular $CF_3CH_2O$), $C_1$-$C_4$-alkoxy-$C_1$-$C_4$-alkyl (in particular methoxymethyl), halogenated $C_1$-$C_4$-alkoxy-$C_1$-$C_4$-alkyl (in particular $CF_2CH_2OCH_3$), bis($C_1$-$C_4$-alkoxy)-$C_1$-$C_4$-alkyl (in particular $(CH_3O)_2CH$), $C_1$-$C_4$-alkoxycarbonyl (in particular methoxycarbonyl), alpha-hydroxyimino-$C_1$-$C_4$-alkoxycarbonylmethyl, $C(X)NR^5R^6$, (in which X represents oxygen or sulphur, $R^5$ represents hydrogen or $C_1$-$C_4$-alkyl (in particular methyl) and $R^6$ represents a radical from the group consisting of $C_1$-$C_5$-alkyl (in particular methyl, ethyl, n-propyl, isopropyl, isobutyl, tert-butyl), $C_1$-$C_4$-haloalkyl (in particular $CF_3CH_2$), cyano-$C_1$-$C_4$-alkyl (in particular $NCCH_2CH(C_2H_5)$), $C_3$-$C_6$-cycloalkyl (in particular cyclopropyl, cyclopentyl, cyclohexyl), $C_3$-$C_6$-cycloalkyl-$C_1$-$C_4$-alkyl (in particular cyclopropylmethyl), $C_1$-$C_4$-alkoxy-$C_1$-$C_4$-alkyl (in particular $CH_3OCH_2CH(CH_3)$, $CH_3CH_2CH_2OCH_2CH(CH_3)$, $CH_3CH_2OCH_2CH_2$, $CH_3OCH_2CH_2$, $CH_3OCH_2CHC_2H_5$, $CH_3CH_2OCH_2CH(CH_3)$, $CH_3CH_2OCH_2CH_2CH_2$, $CH_3OC(CH_3)_2$), $C_1$-$C_4$-alkylthio-$C_1$-$C_4$-alkyl (in particular $CH_3SCH_2CH_2$) and phenyl-$C_1$-$C_4$-alkyl (in particular $C_6H_5CH(CH_3)$ or $R^5$ and $R^6$ together with the nitrogen atom to which they are attached form a 5- or 6-membered ring which may contain one further heteroatom from the group consisting of oxygen, sulphur and nitrogen (in particular, $R^5$ and $R^6$ together represent $(CH_2)_4$, $CH_2)_5$ or $(CH_2)_2(CH_2)_2$), $NR^7R^8$ (in which $R^7$ represents hydrogen or methyl and $R^8$ represents a radical from the group consisting of hydrogen, $C_1$-$C_4$-alkyl (in particular methyl and ethyl), $C_1$-$C_4$-haloalkyl (in particular $CH_2CF_3$ and $CH_2CF_2H$), $C_1$-$C_4$-alkoxy (in particular $OCH_3$), $C_1$-$C_4$-alkylcarbonyl (in particular $COCH_3$), $C_1$-$C_4$-alkoxycarbonyl (in particular $CO_2CH_3$, $CO_2CH_2CH_3$ and $CO_2C(CH_3)_3$,) and $C_1$-$C_4$-alkoxycarbonyl-$C_1$-$C_4$-alkyl (in particular $CH_2CO_2CH_3$) or $R^7$ and $R^8$ together with the nitrogen atom to which they are attached form a 5- or 6-membered ring which may contain an oxygen atom, in particular, $R^7$ and $R^8$ together represents $(CH_2)_4$, $(CH_2)_5$ or $(CH_2)_2O(CH_2)_2$), $C_1$-$C_4$-alkylthio (in particular methylthio), $C_1$-$C_4$-alkylsulphonyl (in particular $CH_3SO_2$), the heterocyclyl radicals dioxanyl, dioxolanyl, morpholinyl, triazolinonyl, oxazolinyl, 5,6-dihydro-[1,3,4]-oxadiazin-2-yl, 5,6-dihydro-[1,4,2]-dioxazin-3-yl and pyrazolinonyl (in particular 1,3-dioxolan-2-yl, 1,3-dioxan-2-yl and 1,2,4-triazolin-3-on-2-yl) (which for their part may be substituted by $C_1$-$C_4$-alkyl (in particular methyl), $C_1$-$C_4$-haloalkyl (in particular $CF_3$) and $C_1$-$C_4$-alkoxy-$C_1$-$C_4$-alkyl (in particular methoxymethyl)), phenyl (which for its part may be substituted by halogen (in particular fluorine, chlorine), the heteroaryl radicals pyridyl, pyridyl N-oxide, pyrimidinyl, pyrazolyl, thiazolyl, furanyl, thienyl, triazolyl, oxadiazolyl, thiadiazolyl, pyrazinyl, triazinyl, and isoquinolinyl (in particular pyrid-2-yl, pyrimid-2-yl, pyrimid-4-yl, pyrazol-1-yl, pyrazol-2-yl, 1,2,4-oxadiazol-3-yl, 1,2,4-triazol-3-yl and 1,2,4-triazin-3-yl) (which for their part may be substituted by halogen (in particular fluorine and chlorine), nitro, $C_1$-$C_4$-alkyl (in particular methyl, ethyl, n-propyl, isopropyl and tert-butyl), $C_1$-$C_4$-haloalkyl (in particular $CF_3$, $CHF_2$ and $CFClH$), $C_1$-$C_4$-alkoxy (in particular methoxy, ethoxy) and $C_3$-$C_6$-cycloalkyl (in particular cyclopropyl, cyclobutyl, cyclopentyl)), the heteroarylalkyl radicals triazolyl-$C_1$-$C_4$-alkyl (in particular triazolylmethyl), pyridyl-$C_1$-$C_4$-alkyl (in particular pyridylmethyl), pyrimidinyl-$C_1$-$C_4$-alkyl (in particular pyrimidinylmethyl) or oxadiazolyl-$C_1$-$C_4$-alkyl (in particular oxadiazolylmethyl (which for their part may be substituted by $C_1$-$C_4$-alkyl (in particular methyl)) and b represents 1 or 2 and in particular represents 1.

Radicals substituted by halogen (also abbreviated as "halo"), for example haloalkyl, are mono- or polysubstituted up to the maximum possible number of substituents. In terms such as "haloalkoxyalkyl", the halogen atoms can be located both in the alkoxy and in the alkyl moiety of the radical, if not expressly stated otherwise. In the case of polyhalogenation, the halogen atoms can be identical or different. Here, halogen represents fluorine, chlorine, bromine and iodine, in particular fluorine, chlorine and bromine, with emphasis given to fluorine and chlorine.

The radical "pyrimidyl" is also referred to as "pyrimidinyl".

Preference, particular preference or very particular preference is given to using compounds carrying the substituents listed in each case as being preferred, particularly preferred or very particularly preferred.

Saturated or unsaturated hydrocarbon radicals, such as alkyl or alkenyl, can in each case be straight-chain or branched as far as is possible, including in combination with heteroatoms, such as, for example, in alkoxy.

Optionally substituted radicals can be mono- or polysubstituted, where in the case of polysubstitution the substituents can be identical or different.

The general or preferred radical definitions or illustrations listed above apply to the end products, and, correspondingly, to the starting materials and intermediates. These radical definitions can be combined with one another as desired, i.e. including combinations between the respective preferred ranges.

Preference according to the invention is given to using compounds of the formula (I) which contain a combination of the meanings listed above as being preferred.

Particular preference according to the invention is given to using compounds of the formula (I) which contain a combination of the meanings listed above as being particularly preferred.

Very particular preference according to the invention is given to using compounds of the formula (I) which contain a combination of the meanings listed above as being very particularly preferred.

Very particular emphasis according to the invention is given to using compounds of the formula (I) which contain a combination of the meanings listed above as being very particularly emphasized.

In an emphasized group of compounds of the formula (I) to be used according to the invention, $G^1$ represents CH.

In a further emphasized group of compounds of the formula (I) to be used according to the invention, $G^1$ represents N.

In a further emphasized group of compounds of the formula (I) to be used according to the invention, $G^1$ represents C-halogen.

In a further emphasized group of compounds of the formula (I) to be used according to the invention, $G^1$ represents CH and $R^1$ represents hydrogen.

In a further emphasized group of compounds of the formula (I) to be used according to the invention, G¹ represents N and R¹ represents hydrogen.

In a further emphasized group of compounds of the formula (I) to be used according to the invention, G¹ represents C-halogen and R¹ represents hydrogen.

In a further emphasized group of compounds of the formula (I) to be used according to the invention, G¹ represents CH and R¹ represents methyl.

In a further emphasized group of compounds of the formula (I) to be used according to the invention, G¹ represents N and R¹ represents methyl.

In a further emphasized group of compounds of the formula (I) to be used according to the invention, G¹ represents C-halogen and R¹ represents methyl.

In a further emphasized group of compounds of the formula (I) to be used according to the invention, G² represents D-R³$_b$.

In a further emphasized group of compounds of the formula (I) to be used according to the invention, G² represents D-R³$_b$ and b represents 1.

The present invention furthermore relates to novel compounds of the formula (I)

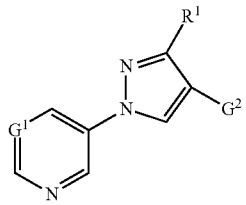

in which
G¹ represents N, CH, C-halogen C-nitro, C-cyano, C-alkyl, C-haloalkyl, C-cycloalkyl, C-alkoxy, C-haloalkoxy,
R¹ represents hydrogen, alkyl haloalkyl, cycloalkyl, halogen, cyano, alkoxy, haloalkoxy, amino, alkylamino, dialkylamino or alkylthio,
G² represents A-R²$_a$, D-R³$_b$ or E-R⁴$_c$ in which
A represents heterocyclyl from the group consisting of 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, oxazolin-2-yl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 5,6-dihydro-[1,3,4]-oxadiazin-2-yl, 5,6-dihydro-[1,3,4]-thiadiazin-2-yl, 5,6-dihydro-[1,4,2]-dioxazin-3-yl, hydroxypyridyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,3-dihydrothien-2-yl, 2,3-dihydrothien-3-yl, 2,4-dihydrothien-2-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl,
R² represents a radical from the group consisting of halogen, cyano, nitro, alkyl, haloalkyl, optionally substituted cycloalkyl, alkoxy, haloalkoxy, alkylthio, haloalkylthio, alkylsulphinyl, alkylsulphonyl, haloalkylsulphinyl, haloalkylsulphonyl, amino, alkylamino, dialkylamino, alkylcarbonylamino, alkoxycarbonylamino, alkoxyalkyl, haloalkoxyalkyl, alkenyl, alkynyl, optionally substituted cycloalkylalkyl, alkylcarbonyl, alkoxycarbonyl, aminocarbonyl, pyridyl and pyrimidyl (where pyridyl and pyrimidyl for their part may be substituted by halogen, alkyl, haloalkyl, alkoxy and haloalkoxy),
a represents a number from the group consisting of 0, 1, 2 and 3,
D represents a heteroaryl radical from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyrid-2-yl, pyrid-3-yl, pyrimid-2-yl, pyrimid-4-yl, imidazolyl, pyrazol-1-yl, pyrazol-3-yl pyrazinyl, 1,2,3-triazinyl, 1,2,4-triazinyl, 1,3,5-triazinyl, thiazol-2-yl, thiazol-4-yl 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl and oxazolyl),
R³ represents a radical from the group consisting of optionally substituted cycloalkyl, optionally substituted cycloalkenyl, optionally substituted cycloalkylalkyl, where in the cycloalkyl moiety of the cycloalkylalkyl radical one or two CH₂ groups may be replaced by oxygen or sulphur, but two oxygen atoms must not be directly adjacent to one another, bis(alkoxy)alkyl, bis(haloalkoxy) alkyl, alkoxy(alkylsulphanyl)alkyl, alkoxy(alkylsulphinyl)alkyl, alkoxy(alkylsulphonyl)alkyl, bis(alkylsulphanyl) alkyl, bis(haloalkylsulphanyl)alkyl, bis (hydroxyalkylsulphanyl)alkyl, alkoxycarbonylalkyl, alpha-hydroxyimino-alkoxycarbonylalkyl, alpha-alkoxyimino-alkoxycarbonylalkyl, C(X)NR⁵R⁶, (in which X represents sulphur, or NOH, R⁵ represents hydrogen or alkyl and R⁶ represents a radical from the group consisting of hydrogen, alkyl, haloalkyl, cyanoalkyl, alkynyl, cycloalkyl, cycloalkylalkyl, alkylcarbonyl, alkoxyalkyl, alkoxycarbonyl, alkoxycarbonylalkyl, alkylthioalkyl, aryl (in particular phenyl), arylalkyl (in particular benzyl) and hetarylalkyl (in particular 2-pyrimidylmethyl) or X represents sulphur, NOH, $NR^{15}$ or oxygen and $R^5$ and $R^6$ together with the nitrogen atom to which they are attached form a ring which optionally contains one or more further heteroatoms from the group consisting of NH, $NCH_3$, $NC_2H_5$, oxygen and sulphur, where two oxygen atoms must not be directly adjacent to one another or $R^5$ and $R^{15}$ together with the nitrogen atoms to which they are attached form a ring which may contain one or more further heteroatoms from the group consisting of NH, $NCH_3$, $NC_2H_5$, oxygen and sulphur, where two oxygen atoms must not be directly adjacent to one another), $NR^7R^8$ (in which $R^7$ represents hydrogen or alkyl and $R^8$ represents alkynyl, cycloalkylalkyl, alkoxy, haloalkoxy, alkoxycarbonylalkyl, alkylthioalkyl, arylalkyl or hetarylalkyl or $R^7$ and $R^8$ together with the nitrogen atom to which they are attached form a ring which optionally contains one or more further heteroatoms from the group consisting of NH, $NCH_3$, $NC_2H_5$, oxygen and sulphur, where two oxygen atoms must not be directly adjacent to one another), the heterocyclyl radicals cycloalkyl and cycloalkenyl in which one or two $CH_2$ groups are replaced by oxygen or sulphur, where two oxygen atoms must not be directly adjacent to one another, in particular dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide (where in these heterocyclyl radicals two hydrogen atoms attached to the same carbon atom may be replaced by =$CH_2$, —$CH_2$—$CH_2$—, —$CH_2$—$CH_2$—$CH_2$— or —$CH_2$—$CH_2$—$CH_2$—$CH_2$—), morpholinyl, triazolinonyl, oxazolinyl, dihydrooxadiazinyl, dihydrodioxazinyl, dihydrooxazolyl, dihydrooxazinyl and pyrazolinonyl (where all heterocyclyl radicals for their part may be substituted by alkyl, haloalkyl, alkoxy and alkoxyalkyl), phenyl (which for its part may be substituted by halogen, cyano, nitro, alkyl and haloalkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl and cycloalkyl) and the heteroarylalkyl radicals triazolylalkyl, pyridylalkyl, pyrimidylalkyl and oxadiazolylalkyl (which for their part may be substituted by alkyl), b represents a number from the group consisting of 1, 2 and 3, E represents aryl, in particular phenyl, $R^4$ represents a radical from the group consisting of halogen, nitro, amino, formyl, cyano, alkylamino, haloalkylamino, dialkylamino, alkyl, haloalkyl, optionally substituted cycloalkyl, optionally substituted cycloalkenyl, optionally substituted cycloalkylalkyl, where in the cycloalkyl moiety of the cycloalkylalkyl radical one or two $CH_2$ groups may be replaced by oxygen or sulphur, but two oxygen atoms must not be directly adjacent to one another, alkoxy, haloalkoxy, alkoxyalkyl, halogenated alkoxyalkyl, bis(alkoxy)alkyl, bis(haloalkoxy)alkyl, alkoxy(alkylsulphanyl)alkyl, alkoxy(alkylsulphinyl)alkyl, alkoxy(alkylsulphonyl)alkyl, bis(alkylsulphanyl)alkyl, bis(haloalkylsulphanyl)alkyl, bis(hydroxyalkylsulphanyl)alkyl, alkoxycarbonyl, alkoxycarbonylalkyl, alpha-hydroxyimino-alkoxycarbonylalkyl, alpha-alkoxyimino-alkoxycarbonylalkyl, $C(X)NR^5R^6$ (in which X represents oxygen, sulphur, $NR^{15}$ or NOH, $R^5$ represents hydrogen or alkyl and $R^6$ and $R^{15}$ independently of one another represent a radical from the group consisting of hydrogen, alkyl, haloalkyl, cyanoalkyl, alkynyl, cycloalkyl, cycloalkylalkyl, alkylcarbonyl, alkoxyalkyl, alkoxycarbonyl, alkoxycarbonylalkyl, alkylthioalkyl, aryl, arylalkyl and hetarylalkyl and $R^6$ may also represent OH or $R^5$ and $R^6$ together with the nitrogen atom to which they are attached form a ring which may contain one or more further heteroatoms from the group consisting of NH, $NCH_3$, $NC_2H_5$, oxygen and sulphur, where two oxygen atoms must not be directly adjacent to one another or $R^5$ and $R^{15}$ together with the nitrogen atoms to which they are attached form a ring which may contain one or more further heteroatoms from the group consisting of NH, $NCH_3$, $NC_2H_5$, oxygen and sulphur, where two oxygen atoms must not be directly adjacent to one another), $NR^7R^8$ (in which $R^7$ represents hydrogen or alkyl and $R^8$ represents a radical from the group consisting of hydrogen, alkyl, haloalkyl, cyanoalkyl, alkynyl, cycloalkyl, cycloalkylalkyl, alkoxy, haloalkoxy, alkoxyalkyl, alkoxycarbonyl, alkoxycarbonylalkyl, alkylthioalkyl, aryl, arylalkyl and hetarylalkyl or $R^7$ and $R^8$ together with the nitrogen atom to which they are attached form a ring which may contain one or more further heteroatoms from the group consisting of NH, $NCH_3$, $NC_2H_5$, oxygen and sulphur), alkylthio, alkylsulphinyl, alkylsulphonyl, the heterocyclyl radicals cycloalkyl and cycloalkenyl in which one or two $CH_2$ groups are replaced by oxygen or sulphur, where two oxygen atoms must not be directly adjacent to one another, in particular dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide (where in these heterocyclyl radicals two hydrogen atoms attached to the same carbon atom may be replaced by =$CH_2$, —$CH_2$—$CH_2$—, —$CH_2$—$CH_2$—$CH_2$— or —$CH_2$—$CH_2$—$CH_2$—$CH_2$—), morpholinyl, triazolinonyl, oxazolinyl, dihydrooxadiazinyl, dihydrodioxazinyl, dihydrooxazolyl, dihydrooxazinyl and pyrazolinonyl (where all heterocyclyl radicals for their part may be substituted by alkyl, haloalkyl, alkoxy and alkoxyalkyl), phenyl (which for its part may be substituted by halogen, cyano, nitro, alkyl and haloalkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl and cycloalkyl) and the heteroarylalkyl radicals triazolylalkyl, pyridylalkyl, pyrimidylalkyl and oxadiazolylalkyl (which for their part may be substituted by halogen and alkyl), and c represents a number from the group consisting of 0, 1, 2 and 3, and also salts, metal complexes and N-oxides thereof.

Preference is given to novel compounds of the formula (I) in which $G^1$ represents N, CH, C-halogen, C-nitro, C-cyano, C—($C_1$-$C_6$)-alkyl, C—($C_1$-$C_6$)-haloalkyl, C—($C_3$-$C_6$)-cycloalkyl, C—($C_1$-$C_6$)-alkoxy, C—($C_1$-$C_6$)-haloalkoxy, in particular N, CH, C-halogen, C-cyano or C-trifluoromethyl, $R^1$ represents hydrogen, $C_1$-$C_6$-alkyl, $C_1$-$C_6$-haloalkyl, $C_3$-$C_6$-cycloalkyl, halogen, cyano, $C_1$-$C_6$-alkoxy, $C_1$-$C_6$-haloalkoxy, amino, $C_1$-$C_6$-alkylamino, di-($C_1$-$C_6$)-alkylamino or $C_1$-$C_6$-alkylthio, in particular hydrogen and methyl and $G^2$ represents $A-R^2_a$, $D-R^3_b$ or $E-R^4_c$ in which A represents heterocyclyl from the group consisting of oxazolin-2-yl, 5,6-dihydro-[1,3,4]-oxadiazin-2-yl, 5,6-dihydro-[1,3,4]-thiadiazin-2-yl, 5,6-dihydro-[1,4,2]-dioxazin-3-yl and hydroxypyridyl, $R^2$ represents a radical from the group consisting of halogen, cyano, nitro, $C_1$-$C_6$-alkyl, $C_1$-$C_6$-haloalkyl, optionally halogen-, cyano-, $C_1$-$C_6$-alkyl-, $C_1$-$C_6$-haloalkyl- and $C_1$-$C_6$-alkoxy-substituted $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-haloalkylsulphinyl, $C_1$-$C_6$-haloalkylsulphonyl, amino, $C_1$-$C_6$-alkylamino, di-($C_1$-$C_6$-alkyl)amino, $C_1$-$C_6$-alkylcarbonylamino, $C_1$-$C_6$-alkoxycarbonylamino, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-alkynyl, optionally halogen-, cyano-, $C_1$-$C_6$-alkyl-, $C_1$-$C_6$-haloalkyl- and $C_1$-$C_6$-alkoxy-substituted $C_3$-$C_6$-cycloalkyl-$C_1$-$C_6$-alkyl, $C_1$-$C_6$-alkylcarbonyl, $C_1$-$C_6$-alkoxycarbonyl, aminocarbonyl, pyridyl and pyrimidyl (where pyridyl and pyrimidyl for their part may be substituted by halogen, $C_1$-$C_6$-alkyl, $C_1$-$C_6$-haloalkyl, $C_1$-$C_6$-alkoxy and $C_1$-$C_6$-haloalkoxy), a represents a number from the group consisting of 0, 1, 2 and 3, D represents a heteroaryl radical from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyrid-2-yl, pyrid-3-yl, pyrimid-2-yl, pyrimid-4-yl, imidazolyl, pyrazol-1-yl, pyrazol-3-yl pyrazinyl, 1,2,3-triazinyl, 1,2,4-triazinyl, 1,3,5-triazinyl, thiazol-2-yl, thiazol-4-yl 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl and oxazolyl), $R^3$ represents a radical from the group consisting of optionally halogen-, cyano-, $C_1$-$C_6$-alkyl-, $C_1$-$C_6$-haloalkyl- and $C_1$-$C_6$-alkoxy-substituted $C_3$-$C_6$-cycloalkyl, optionally halogen-, cyano-, $C_1$-$C_6$-alkyl-, $C_1$-$C_6$-haloalkyl- and $C_1$-$C_6$-alkoxy-substituted $C_3$-$C_6$-cycloalkenyl, optionally halogen-, cyano-, $C_1$-$C_6$-alkyl-, $C_1$-$C_6$-haloalkyl- and $C_1$-$C_6$-alkoxy-substituted $C_3$-$C_6$-cycloalkyl-$C_1$-$C_6$-alkyl where in the cycloalkyl moiety, if 5- or 6-membered, of the cycloalkylalkyl radical one or two $CH_2$ groups may be replaced by oxygen or sulphur, but two oxygen atoms must not be directly adjacent to one another, bis($C_1$-$C_6$-haloalkoxy)-$C_1$-$C_6$-alkyl, $C_1$-$C_6$-alkoxy($C_1$-$C_6$-alkylsulphanyl)-$C_1$-$C_6$-alkyl, $C_1$-$C_6$-alkoxy($C_1$-$C_6$-alkylsulphinyl)-$C_1$-$C_6$-alkyl, $C_1$-$C_6$-alkoxy($C_1$-$C_6$-alkylsulphonyl)-$C_1$-$C_6$-alkyl, bis($C_1$-$C_6$-alkylsulphanyl)-$C_1$-$C_6$-alkyl, bis($C_1$-$C_6$-haloalkylsulphanyl)-$C_1$-$C_6$-alkyl, bis(hydroxyalkylsulphanyl)-$C_1$-$C_6$-alkyl, $C_1$-$C_6$-alkoxycarbonyl-$C_1$-$C_6$-alkyl, alpha-hydroxyimino-$C_1$-$C_6$-alkoxycarbonylmethyl, alpha-$C_1$-$C_6$-alkoxyimino-$C_1$-$C_6$-alkoxycarbonylmethyl, $C(X)NR^5R^6$ (in which X represents sulphur or NOH, $R^5$ represents hydrogen or $C_1$-$C_6$-alkyl and $R^6$ represents a radical from the group consisting of hydrogen, $C_1$-$C_6$-alkyl, $C_1$-$C_6$-haloalkyl, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxycarbonyl, $C_1$-$C_6$-alkoxy-$C_1$-$C_6$-alkyl, $C_1$-$C_6$-alkoxycarbonyl-$C_1$-$C_6$-alkyl, $C_1$-$C_6$-alkylthio-$C_1$-$C_6$-alkyl, phenyl-$C_1$-$C_6$-alkyl and hetaryl-$C_1$-$C_6$-alkyl in which hetaryl represents pyrimidyl or X represents sulphur, $NR^{15}$, NOH or oxygen and $R^5$ and $R^6$ together with the nitrogen atom to which they are attached form a 5- to 7-membered ring which may contain one or more further heteroatoms from the group consisting of NH, $NCH_3$, $NC_2H_5$, oxygen and sulphur, where two oxygen atoms must not be directly adjacent to one another or $R^5$ and $R^{15}$ together with the nitrogen atoms to which they are attached form a ring which may contain one or more further heteroatoms from the group consisting of NH, $NCH_3$, $NC_2H_5$, oxygen and sulphur, where two oxygen atoms must not be directly adjacent to one another), $NR^7R^8$ (in which $R^7$ represents hydrogen or $C_1$-$C_6$-alkyl and $R^8$ represents a radical from the group consisting of $C_2$-$C_6$-alkynyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkoxycarbonyl-$C_1$-$C_6$-alkyl, $C_1$-$C_6$-alkylthio-$C_1$-$C_6$-alkyl, phenyl-$C_1$-$C_6$-alkyl and hetaryl-$C_1$-$C_6$-alkyl in which hetaryl represents pyrimidyl or $R^7$ and $R^8$ together with the nitrogen atom to which they are attached form a 5- to 7-membered ring which may contain one further heteroatom from the group consisting of NH, $NCH_3$, $NC_2H_5$, oxygen and sulphur), the heterocyclyl radicals $C_3$-$C_8$-cycloalkyl and $C_4$-$C_8$-cycloalkenyl in which one or two $CH_2$ groups are replaced by oxygen or sulphur, where two oxygen atoms must not be directly adjacent to one another, in particular dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide (where in these heterocyclyl radicals two hydrogen atoms attached to the same carbon atom may be replaced by $=CH_2$, $-CH_2-CH_2-$, $-CH_2-CH_2-CH_2-$ or $-CH_2-CH_2-CH_2-CH_2-$), morpholinyl, triazolinonyl, oxazolinyl, dihydrooxadiazinyl, dihydrodioxazinyl, dihydrooxazolyl, dihydrooxazinyl and pyrazolinonyl (in particular 1,3-dioxolan-2-yl, 1,3-dioxan-2-yl, 1,3-dioxepan-2-yl, 1,3-dioxocan-2-yl, 1,3-oxathian-2-yl, 1,3-oxathiolan-2-yl, 1,3-oxathiepan-2-yl, 1,3-oxathiocan-2-yl, 1,3-dithian-2-yl, 1,3-dithiolan-2-yl, 1,3-dithiepan-2-yl, 1,3-dithiocan-2-yl, 4,5-dihydro-1,3-oxazol-2-yl, 5,6-dihydro-4H-1,3-oxazin-2-yl, 1,3-oxathianyl 3-oxide, 1,3-oxathiolanyl 3-oxide, 1,3-oxathiepanyl 3-oxide, 1,3-oxathiocanyl 3-oxide, 1,3-oxathianyl 3,3-dioxide, 1,3-oxathiolanyl 3,3-dioxide, 1,3-oxathiepanyl 3,3-dioxide, 1,3-oxathiocanyl 3,3-dioxide (where in these heterocyclyl radicals two hydrogen atoms attached to the same carbon atom may be replaced by $=CH_2$, $-CH_2-CH_2-$, $-CH_2-CH_2-CH_2-$ or $-CH_2-CH_2-CH_2-CH_2-$) and 1,2,4-triazolin-3-on-2-yl) (where all heterocyclyl radicals for their part may be substituted by $C_1$-$C_6$-alkyl, $C_1$-$C_6$-haloalkyl, $C_1$-$C_6$-alkoxy and $C_1$-$C_6$-alkoxy-$C_1$-$C_6$-alkyl), phenyl (which for its part may be substituted by halogen, cyano, nitro, $C_1$-$C_6$-alkyl and $C_1$-$C_6$-haloalkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (in particular pyrid-2-yl, pyrimid-2-yl, pyrimid-4-yl, pyrazol-1-yl, pyrazol-3-yl, pyrazol-5-yl, 1,2,4-oxadiazol-3-yl, 1,2,4-triazol-3-yl, 1,2,3-triazol-1-yl, 1,2,3-triazol-2-yl, 1,2,4-thiadiazol-3-yl and 1,2,4-triazin-3-yl) (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl and $C_3$-$C_6$-cycloalkyl) and the heteroarylalkyl radicals triazolyl-$C_1$-$C_6$-alkyl, pyridyl-$C_1$-$C_6$-alkyl, pyrimidyl-$C_1$-$C_6$-alkyl and oxadiazolyl-$C_1$-$C_6$-alkyl (which for their part may be substituted by $C_1$-$C_6$-alkyl), b represents a number from the group consisting of 1, 2 and 3, E represents phenyl, $R^4$ represents a radical from the group consisting of halogen, nitro, amino, formyl, cyano, $C_1$-$C_6$-alkylamino, $C_1$-$C_6$-haloalkylamino, di-($C_1$-$C_6$-alkyl)amino, $C_1$-$C_6$-alkyl, $C_1$-$C_6$-haloalkyl, optionally halogen-, cyano-, $C_1$-$C_6$-alkyl-, $C_1$-$C_6$-haloalkyl- and $C_1$-$C_6$-alkoxy-substituted $C_3$-$C_6$-cycloalkyl, optionally halogen-, cyano-, $C_1$-$C_6$-alkyl-, $C_1$-$C_6$-haloalkyl- and $C_1$-$C_6$-alkoxy-substituted $C_3$-$C_6$-cycloalkenyl, optionally halogen-, cyano-, $C_1$-$C_6$-alkyl-, $C_1$-$C_6$-haloalkyl- and $C_1$-$C_6$-alkoxy-substituted $C_3$-$C_6$-cycloalkyl-$C_1$-$C_6$-alkyl where in the cycloalkyl moiety, if 5- or 6-membered, of the cycloalkylalkyl radical one or two $CH_2$ groups may be replaced by oxygen or sulphur, but two oxygen atoms must not be directly adjacent to one another, $C_1$-$C_6$-alkoxy, $C_1$-$C_6$-haloalkoxy, $C_1$-$C_6$-alkoxy-$C_1$-$C_6$-alkyl, halogenated $C_1$-$C_6$-alkoxy-$C_1$-$C_6$-alkyl, bis($C_1$-$C_6$-alkoxy)-$C_1$-$C_6$-alkyl, bis($C_1$-$C_6$-haloalkoxy)-$C_1$-$C_6$-alkyl, $C_1$-$C_6$-alkoxy($C_1$-$C_6$-alkylsulphanyl)-$C_1$-$C_6$-alkyl, $C_1$-$C_6$-alkoxy($C_1$-$C_6$-alkylsulphinyl)-$C_1$-$C_6$-alkyl, $C_1$-$C_6$-alkoxy($C_1$-$C_6$-alkylsulphonyl)-$C_1$-$C_6$-alkyl, bis($C_1$-$C_6$-alkylsulphanyl)-$C_1$-$C_6$-alkyl, bis($C_1$-$C_6$-haloalkylsulphanyl)-$C_1$-$C_6$-alkyl, bis($C_1$-$C_6$-hydroxyalkylsulphanyl)-$C_1$-$C_6$-alkyl, $C_1$-$C_6$-alkoxycarbonyl, $C_1$-$C_6$-alkoxycarbonyl-$C_1$-$C_6$-alkyl, alpha-hydroxyimino-$C_1$-$C_6$-alkoxycarbonylmethyl, alpha-$C_1$-$C_6$-alkoxyimino-$C_1$-$C_6$-alkoxycarbonylmethyl, $C(X)N^5R^6$, (in which X represents oxygen, sulphur, $NR^{15}$ or NOH, $R^5$ represents hydrogen or $C_1$-$C_6$-alkyl and $R^6$ and $R^{15}$ independently of one another represent a radical from the group consisting of hydrogen, $C_1$-$C_6$-alkyl, $C_1$-$C_6$-haloalkyl, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkylcarbonyl, $C_1$-$C_6$-alkoxy-$C_1$-$C_6$-alkyl, $C_1$-$C_6$-alkoxycarbonyl, $C_1$-$C_6$-alkoxycarbonyl-$C_1$-$C_6$-alkyl, $C_1$-$C_6$-alkylthio-$C_1$-$C_6$-alkyl, phenyl, phenyl-$C_1$-$C_6$-alkyl and hetaryl-$C_1$-$C_6$-alkyl in which hetaryl represents pyrimidyl and $R^6$ may also represent OH or $R^5$ and $R^6$ together with the nitrogen atom to which they are attached form a 5- to 7-membered ring which may contain one further heteroatom from the group consisting of NH, $NCH_3$, $NC_2H_5$, oxygen and sulphur or $R^5$ and $R^{15}$ together with the nitrogen atoms to which they are attached form a 5- to 7-membered ring which may contain one or more, in particular one or two, further heteroatoms from the group consisting of NH, $NCH_3$, $NC_2H_5$, oxygen and sulphur, where two oxygen atoms must not be directly adjacent to one another), $NR^7R^8$ (in which $R^7$ represents hydrogen or $C_1$-$C_6$-alkyl and $R^8$ represents a radical from the group consisting of hydrogen, $C_1$-$C_6$-alkyl, $C_1$-$C_6$-haloalkyl, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkoxycarbonyl, $C_1$-$C_6$-alkoxycarbonyl-$C_1$-$C_6$-alkyl, $C_1$-$C_6$-alkylthio-$C_1$-$C_6$-alkyl, phenyl, phenyl-$C_1$-$C_6$-alkyl and hetaryl-$C_1$-$C_6$-alkyl in which hetaryl represents pyrimidyl or $R^7$ and $R^8$ together with the nitrogen atom to which they are attached form a 5- to 7-membered ring which may contain one further heteroatom from the group consisting of NH, $NCH_3$, $NC_2H_5$, oxygen and sulphur), $C_1$-$C_6$-alkylthio, $C_1$-$C_6$-alkylsulphinyl, $C_1$-$C_6$-alkylsulphonyl, the heterocyclyl radicals $C_3$-$C_8$-cycloalkyl and $C_4$-$C_8$-cycloalkenyl in which one or two $CH_2$ groups are replaced by oxygen or sulphur, where two oxygen atoms must not be directly adjacent to one another, in particular dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide (where in these heterocyclyl radicals two hydrogen atoms attached to the same carbon atom may be replaced by $=CH_2$, $-CH_2-CH_2-$, $-CH_2-CH_2-CH_2-$ or $-CH_2-CH_2-CH_2-CH_2-$), morpholinyl, triazolinonyl, oxazolinyl, dihydrooxadiazinyl, dihydrodioxazinyl, dihydrooxazolyl, dihydrooxazinyl and pyrazolinonyl (in particular 1,3-dioxolan-2-yl, 1,3-dioxan-2-yl, 1,3-dioxepan-2-yl, 1,3-dioxocan-2-yl, 1,3-oxathian-2-yl, 1,3-oxathiolan-2-yl, 1,3-oxathiepan-2-yl, 1,3-oxathiocan-2-yl, 1,3-dithian-2-yl, 1,3-dithiolan-2-yl, 1,3-dithiepan-2-yl, 1,3-dithiocan-2-yl, 4,5-dihydro-1,3-oxazol-2-yl, 5,6-dihydro-4H-1,3-oxazin-2-yl, 1,3-oxathianyl 3-oxide, 1,3-oxathiolanyl 3-oxide, 1,3-oxathiepanyl 3-oxide, 1,3-oxathiocanyl 3-oxide, 1,3-oxathianyl 3,3-dioxide, 1,3-oxathiolanyl 3,3-dioxide, 1,3-oxathiepanyl 3,3-dioxide, 1,3-oxathiocanyl 3,3-dioxide (where in these heterocyclyl radicals two hydrogen atoms attached to the same carbon atom may be replaced by $=CH_2$, $-CH_2-CH_2-$, $-CH_2-CH_2-CH_2-$ or $-CH_2-CH_2-CH_2CH_2-$) and 1,2,4-triazolin-3-on-2-yl) (where all heterocyclyl radicals for their part may be substituted by $C_1$-$C_6$-alkyl, $C_1$-$C_6$-haloalkyl, $C_1$-$C_6$-alkoxy and $C_1$-$C_6$-alkoxy-$C_1$-$C_6$-alkyl), phenyl (which for its part may be substituted by halogen, cyano, nitro, $C_1$-$C_6$-alkyl and $C_1$-$C_6$-haloalkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (in particular pyrid-2-yl, pyrimid-2-yl, pyrimid-4-yl, pyrazol-1-yl, pyrazol-3-yl, pyrazol-5-yl, 1,2,4-oxadiazol-3-yl, 1,2,4-triazol-3-yl, 1,2,3-triazol-1-yl, 1,2,3-triazol-2-yl, 1,2,4-thiadiazol-3-yl and 1,2,4-triazin-3-yl) (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl and $C_3$-$C_6$-cycloalkyl) and the heteroarylalkyl radicals triazolyl-$C_1$-$C_6$-alkyl, pyridyl-$C_1$-$C_6$-alkyl, pyrimidyl-$C_1$-$C_6$-alkyl and oxadiazolyl-$C_1$-$C_6$-alkyl (which for their part may be substituted by halogen and $C_1$-$C_6$-alkyl) and c represents a number from the group consisting of 0, 1, 2 and 3, and also salts, metal complexes and N-oxides of the compounds of the formula (I).

Particular preference is given to novel compounds of the formula (I) in which $G^1$ represents N, CH, C-halogen, C-nitro, C-cyano, C—($C_1$-$C_4$)-alkyl, C—($C_1$-$C_4$)-haloalkyl, C—($C_3$-$C_6$)-cycloalkyl, C—($C_1$-$C_4$)-alkoxy, C—($C_1$-$C_4$)-haloalkoxy, in particular N, CH, C-halogen, C-cyano or C-trifluoromethyl, $R^1$ represents hydrogen, $C_1$-$C_4$-alkyl, $C_1$-$C_4$-haloalkyl, $C_3$-$C_6$-cycloalkyl, halogen, cyano, $C_1$-$C_4$-alkoxy, $C_1$-$C_4$-haloalkoxy, amino, $C_1$-$C_4$-alkylamino, di-($C_1$-$C_4$)-alkylamino or $C_1$-$C_4$-alkylthio, in particular hydrogen and methyl, $G^2$ represents $A-R^2{}_a$, $D-R^3{}_b$ or $E-R^4{}_c$ in which A represents heterocyclyl from the group consisting of oxazolin-2-yl, 5,6-dihydro-[1,3,4]-oxadiazin-2-yl, 5,6-dihydro-[1,3,4]-thiadiazin-2-yl and 5,6-dihydro-[1,4,2]-dioxazin-3-yl, $R^2$ represents a radical from the group consisting of halogen, cyano, nitro, $C_1$-$C_4$-alkyl, $C_1$-$C_4$-haloalkyl, optionally fluorine-, chlorine-, cyano-, methyl-, methoxy- and trifluoromethyl-substituted $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-alkylsulphonyl, $C_1$-$C_4$-haloalkylsulphinyl, $C_1$-$C_4$-haloalkylsulphonyl, amino, $C_1$-$C_4$-alkylamino, di-($C_1$-$C_4$-alkyl)amino, $C_1$-$C_4$-alkylcarbonylamino, $C_1$-$C_4$-alkoxycarbonylamino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-alkynyl, optionally fluorine-, chlorine-, cyano-, methyl-, methoxy- and trifluoromethyl-substituted $C_3$-$C_6$-cycloalkyl-$C_1$-$C_4$-alkyl, $C_1$-$C_4$-alkylcarbonyl, $C_1$-$C_4$-alkoxycarbonyl, aminocarbonyl, pyridyl and pyrimidyl (where pyridyl and pyrimidyl for their part may be substituted by halogen, $C_1$-$C_4$-alkyl, $C_1$-$C_4$-haloalkyl, $C_1$-$C_4$-alkoxy and $C_1$-$C_4$-haloalkoxy), a represents a number from the group consisting of 0, 1, 2 and 3, D represents a heteroaryl radical from the group consisting of pyrid-2-yl, pyrid-3-yl, pyrimid-2-yl, pyrimid-4-yl, imidazolyl, pyrazol-1-yl, pyrazol-3-yl pyrazinyl, 1,2,3-triazinyl, 1,2,4-triazinyl, 1,3,5-triazinyl, thiazol-2-yl, thiazol-4-yl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl and oxazolyl (in particular pyrazol-1-yl, pyrazol-3-yl, pyrid-2-yl, pyrid-3-yl, pyrimid-2-yl, pyrimid-4-yl, thiazol-2-yl and thiazol-4-yl), $R^3$ represents a radical from the group consisting of optionally fluorine-, chlorine-, cyano-, methyl-, methoxy- and trifluoromethyl-substituted $C_3$-$C_6$-cycloalkyl, optionally fluorine-, chlorine-, cyano-, methyl-, methoxy- and trifluoromethyl-substituted $C_3$-$C_6$-cycloalkenyl, optionally fluorine-, chlorine-, cyano-, methyl-, methoxy- and trifluoromethyl-substituted $C_3$-$C_6$-cycloalkyl-$C_1$-$C_4$-alkyl where in the cycloalkyl moiety, if 5- or 6-membered, of the cycloalkylalkyl radical one or two $CH_2$ groups may be replaced by oxygen or sulphur, but two oxygen atoms must not be directly adjacent to one another, bis($C_1$-$C_4$-haloalkoxy)-$C_1$-$C_4$-alkyl, $C_1$-$C_4$-alkoxy($C_1$-$C_4$-alkylsulphanyl)-$C_1$-$C_4$-alkyl, $C_1$-$C_4$-alkoxy($C_1$-$C_4$-alkylsulphinyl)-$C_1$-$C_4$-alkyl, $C_1$-$C_4$-alkoxy($C_1$-$C_4$-alkylsulphonyl)-$C_1$-$C_4$-alkyl, bis($C_1$-$C_4$-alkylsulphanyl)-$C_1$-$C_4$-alkyl, bis($C_1$-$C_4$-haloalkylsulphanyl)-$C_1$-$C_4$-alkyl, bis(hydroxyalkylsulphanyl)-$C_1$-$C_4$-alkyl, $C_1$-$C_4$-alkoxycarbonyl-$C_1$-$C_4$-alkyl, alpha-hydroxyimino-$C_1$-$C_4$-alkoxycarbonylmethyl, alpha-$C_1$-$C_4$-alkoxyimino-$C_1$-$C_4$-alkoxycarbonylmethyl, $C(X)NR^5R^6$ (in which X represents sulphur, $R^5$ represents hydrogen or $C_1$-$C_4$-alkyl and $R^6$ represents a radical from the group consisting of hydrogen, $C_1$-$C_5$-alkyl, $C_1$-$C_4$-haloalkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkylthio-$C_1$-$C_4$-alkyl and phenyl-$C_1$-$C_4$-alkyl or X represents sulphur or oxygen and $R^5$ and $R^6$ together with the nitrogen atom to which they are attached form a 5- to 7-membered ring which may contain one further heteroatom from the group consisting of NH, $NCH_3$, $NC_2H_5$, oxygen and sulphur), $NR^7R^8$ (in which $R^7$ represents hydrogen or $C_1$-$C_4$-alkyl and $R^8$ represents a radical from the group consisting of $C_2$-$C_4$-alkynyl, $C_3$-$C_6$-cycloalkyl-$C_1$-$C_4$-alkyl, $C_1$-$C_4$-alkoxy, $C_1$-$C_4$-haloalkoxy, $C_1$-$C_4$-alkoxycarbonyl-$C_1$-$C_4$-alkyl, $C_1$-$C_4$-alkylthio-$C_1$-$C_4$-alkyl or phenyl-$C_1$-$C_4$-alkyl or $R^7$ and $R^8$ together with the nitrogen atom to which they are attached form a 5- or 6-membered ring which may contain one further heteroatom from the group consisting of oxygen, sulphur, NH, $NCH_3$ and $NC_2H_5$), the heterocyclyl radicals dioxanyl, dioxolanyl, dioxepanyl, oxathianyl, oxathiolanyl, oxathiepanyl, dithianyl, dithiolanyl, dithiepanyl, oxathianyl oxide, oxathiolanyl oxide, oxathiepanyl oxide, oxathianyl dioxide, oxathiolanyl dioxide, oxathiepanyl dioxide (where in these heterocyclyl radicals two hydrogen atoms attached to the same carbon atom may be replaced by $=CH_2$, $—CH_2—CH_2—$, $—CH_2—CH_2—CH_2—$ or $—CH—CH_2—CH_2—CH_2—$), morpholinyl, triazolinonyl, oxazolinyl, dihydrooxadiazinyl, dihydrodioxazinyl, dihydrooxazolyl, dihydrooxazinyl and pyrazolinonyl (in particular 1,3-dioxolan-2-yl, 1,3-dioxan-2-yl, 1,3-dioxepan-2-yl, 1,3-oxathian-2-yl, 1,3-oxathiolan-2-yl, 1,3-oxathiepan-2-yl, 1,3-dithian-2-yl, 1,3-dithiolan-2-yl, 1,3-dithiepan-2-yl, 4,5-dihydro-1,3-oxazol-2-yl, 5,6-dihydro-4H-1,3-oxazin-2-yl, 1,3-oxathianyl 3-oxide, 1,3-oxathiolanyl 3-oxide, 1,3-oxathiepanyl 3-oxide, 1,3-oxathianyl 3,3-dioxide, 1,3-oxathiolanyl 3,3-dioxide, 1,3-oxathiepanyl 3,3-dioxide (where in these heterocyclyl radicals two hydrogen atoms attached to the same carbon atom may be replaced by $=CH_2$, $—CH_2—CH_2—$, $—CH_2—CH_2—CH_2—$ or $—CH_2—CH_2—CH_2—CH_2—$) and 1,2,4-triazolin-3-on-2-yl) (where all heterocyclyl radicals for their part may be substituted by $C_1$-$C_4$-alkyl, $C_1$-$C_4$-haloalkyl and $C_1$-$C_4$-alkoxy-$C_1$-$C_4$-alkyl), phenyl (which for its part may be substituted by halogen, cyano, nitro, $C_1$-$C_4$-alkyl and $C_1$-$C_4$-haloalkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (in particular pyrid-2-yl, pyrimid-2-yl, pyrimid-4-yl, pyrazol-1-yl, pyrazol-3-yl, pyrazol-5-yl, 1,2,4-oxadiazol-3-yl, 1,2,4-triazol-3-yl, 1,2,3-triazol-1-yl, 1,2,3-triazol-2-yl, 1,2,4-thiadiazol-3-yl, tetrazolyl and 1,2,4-triazin-3-yl) (which for their part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cycloalkyl) and the heteroarylalkyl radicals triazolyl-$C_1$-$C_4$-alkyl, pyridyl-$C_1$-$C_4$-alkyl, pyrimidyl-$C_1$-$C_4$-alkyl or oxadiazolyl-$C_1$-$C_4$-alkyl (which for their part may be substituted by halogen and $C_1$-$C_4$-alkyl), b represents a number from the group consisting of 1 and 2, E represents phenyl, $R^4$ represents a radical from the group consisting of halogen, cyano, $C_1$-$C_4$-alkyl, $C_1$-$C_4$-haloalkyl, $C_1$-$C_4$-alkoxy and $C_1$-$C_4$-haloalkoxy and c represents a number from the group consisting of 0, 1 and 2.

Very particular preference is given to novel compounds of the formula (I) in which $G^1$ represents N, CH, C-halogen, C-cyano, C—$CH_3$, C—$CF_3$, C-cyclopropyl, C—$OCH_3$, C—$OCF_3$, in particular N, CH, C-halogen, $R^1$ represents hydrogen, methyl, trifluoromethyl, cyclopropyl, halogen, cyano, methoxy, trifluoromethoxy, amino, methylamino, dimethylamino, in particular hydrogen, $G^2$ represents $A-R^2{}_a$ or $D-R^3{}_b$ in which A represents heterocyclyl from the group consisting of oxazolin-2-yl, 5,6-dihydro-[1,3,4]-thiadiazin-2-yl and 5,6-dihydro-[1,3,4]-oxadiazin-2-yl, R² represents a radical from the group consisting of pyridyl and pyrimidin-2-yl which may be substituted by halogen, $C_1$-$C_4$-alkyl, $C_1$-$C_4$-haloalkyl, $C_1$-$C_4$-alkoxy and $C_1$-$C_4$-haloalkoxy, a represents 0, 1 or 2 and in particular represents 1, D represents a heteroaryl radical from the group consisting of pyrazol-1-yl, pyrazol-3-yl, pyrid-2-yl, pyrid-3-yl, pyrimid-2-yl, pyrimid-4-yl, thiazol-2-yl and thiazol-4-yl, R³ represents a radical from the group consisting of optionally fluorine-, chlorine-, cyano-, methyl-, methoxy- and trifluoromethyl-substituted $C_3$-$C_6$-cycloalkyl (in particular cyclopropylmethyl), optionally fluorine-, chlorine-, cyano-, methyl-, methoxy- and trifluoromethyl-substituted $C_3$-$C_6$-cycloalkenyl, optionally fluorine-, chlorine-, cyano-, methyl-, methoxy- and trifluoromethyl-substituted $C_3$-$C_6$-cycloalkyl-$C_1$-$C_4$-alkyl where in the cycloalkyl moiety, if 5- or 6-membered, of the cycloalkylalkyl radical one or two $CH_2$ groups may be replaced by oxygen or sulphur, but two oxygen atoms must not be directly adjacent to one another, alpha-hydroxyimino-$C_1$-$C_4$-alkoxy-carbonylmethyl, $C(X)NR^5R^6$ (in which X represents sulphur, R⁵ represents hydrogen and R⁶ represents a radical from the group consisting of hydrogen, $C_1$-$C_5$-alkyl (in particular methyl, ethyl, n-propyl, isopropyl, isobutyl, tert-butyl, $C_1$-$C_4$-haloalkyl (in particular $CF_3CH_2$), cyano-$C_1$-$C_4$-alkyl (in particular $NCCH_2CH(C_2H_5)$), $C_3$-$C_6$-cycloalkyl (in particular cyclopropyl, cyclopentyl, cyclohexyl), $C_3$-$C_6$-cycloalkyl-$C_1$-$C_4$-alkyl (in particular cyclopropylmethyl), $C_1$-$C_4$-alkoxy-$C_1$-$C_4$-alkyl (in particular $CH_3OCH_2CH(CH_3)$, $CH_3CH_2CH_2OCH_2CH(CH_3)$, $CH_3CH_2OCH_2CH_2$, $CH_3OCH_2CH_2CH_2$, $CH_3OCH_2CHC_2H_5$, $CH_3CH_2OCH_2CH(CH_3)$, $CH_3CH_2OCH_2CH_2CH_2$, $CH_3OC(CH_3)_2$, $C_1$-$C_4$-alkylthio-$C_1$-$C_4$-alkyl (in particular $CH_3SCH_2CH_2$) and phenyl-$C_1$-$C_4$-alkyl (in particular $C_6H_5CH(CH_3)$) or X represents sulphur or oxygen and R⁵ and R⁶ together with the nitrogen atom to which they are attached form a 5- to 7-membered ring which optionally contains a further heteroatom from the group consisting of NH, $NCH_3$, $NC_2H_5$, oxygen and sulphur (in particular, R⁵ and R⁶ together represent $(CH_2)_4$, $(CH_2)_5$ or $(CH_2)_2O(CH_2)_2)$), $NR^7R^8$ (in which R⁷ represents hydrogen or methyl and R⁸ represents $C_1$-$C_4$-alkoxycarbonyl-$C_1$-$C_4$-alkyl (in particular $CH_2CO_2CH_3$) or R⁷ and R⁸ together with the nitrogen atom to which they are attached form a 5- or 6-membered ring which may contain an oxygen atom, for example, R⁷ and R⁸ together represent $(CH_2)_4$, $(CH_2)_5$ or $(CH_2)_2O(CH_2)_2)$, the heterocyclyl radicals dioxanyl, dioxolanyl, oxathianyl, oxathiolanyl, dithianyl, dithiolanyl, oxathianyl oxide, oxathiolanyl oxide, oxathianyl dioxide, oxathiolanyl dioxide (where in these heterocyclyl radicals two hydrogen atoms attached to the same carbon atom may be replaced by =$CH_2$, —$CH_2$—$CH_2$—, —$CH_2$—$CH$=$CH_2$— or —$CH_2$—$CH_2$—$CH_2$—$CH_2$—), morpholinyl, triazolinonyl, oxazolinyl, dihydrooxadiazinyl, dihydrodioxazinyl, dihydrooxazolyl, dihydrooxazinyl and pyrazolinonyl (in particular 1,3-dioxolan-2-yl, 1,3-dioxan-2-yl, 1,3-oxathian-2-yl, 1,3-oxathiolan-2-yl, 1,3-dithian-2-yl, 1,3-dithiolan-2-yl, 4,5-dihydro-1,3-oxazol-2-yl, 5,6-dihydro-4H-1,3-oxazin-2-yl, 1,3-oxathianyl 3-oxide, 1,3-oxathiolanyl 3-oxide, 1,3-oxathianyl 3,3-dioxide, 1,3-oxathiolanyl 3,3-dioxide (where in these heterocyclyl radicals two hydrogen atoms attached to the same carbon atom may be replaced by =$CH_2$, —$CH_2$—$CH_2$—, —$CH_2$—$CH_2$—$CH_2$— or —$CH_2$—$CH_2$—$CH_2$—$CH_2$—) and 1,2,4-triazolin-3-on-2-yl) (where all heterocyclyl radicals for their part may be substituted by $C_1$-$C_4$-alkyl (in particular methyl), $C_1$-$C_4$-haloalkyl (in particular $CF_3$) and $C_1$-$C_4$-alkoxy-$C_1$-$C_4$-alkyl (in particular methoxymethyl)), phenyl (which for its part may be substituted by halogen (in particular fluorine, chlorine), the heteroaryl radicals pyridyl, pyridyl N-oxide, pyrimidinyl, pyrazolyl, thiazolyl, furanyl, thienyl, triazolyl, tetrazolyl, oxadiazolyl, thiadiazolyl, pyrazinyl, triazinyl, and isoquinolinyl (in particular pyrid-2-yl, pyrimid-2-yl, pyrimid-4-yl, pyrazol-1-yl, pyrazol-3-yl, pyrazol-5-yl, 1,2,4-oxadiazol-3-yl, 1,2,4-triazol-3-yl, 1,2,3-triazol-1-yl, 1,2,3-triazol-2-yl, 1,2,4-thiadiazol-3-yl, tetrazolyl and 1,2,4-triazin-3-yl) (which for their part may be substituted by halogen (in particular fluorine and chlorine), nitro, $C_1$-$C_4$-alkyl (in particular methyl, ethyl, n-propyl, isopropyl and tert-butyl), $C_1$-$C_4$-haloalkyl (in particular $CF_3$, $CHF_2$ and $CF_2Cl$), $C_1$-$C_4$-alkoxy (in particular methoxy, ethoxy) and $C_3$-$C_6$-cycloalkyl (in particular cyclopropyl, cyclobutyl, cyclopentyl)), the heteroarylalkyl radicals triazolyl-$C_1$-$C_4$-alkyl (in particular triazolylmethyl), pyridyl-$C_1$-$C_4$-alkyl (in particular pyridylmethyl), pyrimidinyl-$C_1$-$C_4$-alkyl (in particular pyrimidinylmethyl) or oxadiazolyl-$C_1$-$C_4$-alkyl (in particular oxadiazolylmethyl (which for their part may be substituted by $C_1$-$C_4$-alkyl (in particular methyl)) and b represents 1 or 2 and in particular represents 1.

The invention also relates to novel compounds of the formula (I) in which

G¹ represents N, CH or C-halogen,

R¹ represents hydrogen or alkyl,

G² represents A-R²$_a$, D-R³$_b$ or E-R⁴$_c$ in which

A represents heterocyclyl from the group consisting of 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, oxazolin-2-yl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 5,6-dihydro-[1,3,4]-oxadiazin-2-yl, 5,6-dihydro-[1,3,4]-thiadiazin-2-yl, 5,6-dihydro-[1,4,2]-dioxazin-3-yl, hydroxypyridyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,3-dihydrothien-2-yl, 2,3-dihydrothien-3-yl, 2,4-dihydrothien-2-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, $R^2$ represents a radical from the group consisting of halogen, cyano, nitro, alkyl, haloalkyl, cycloalkyl, alkoxy, haloalkoxy, alkylthio, haloalkylthio, alkylsulphinyl, alkylsulphonyl, haloalkylsulphinyl, haloalkylsulphonyl, amino, alkylamino, dialkylamino, alkylcarbonylamino, alkoxycarbonylamino, alkoxyalkyl, haloalkoxyalkyl, alkenyl, alkynyl, cycloalkylalkyl, alkylcarbonyl, alkoxycarbonyl, aminocarbonyl, pyridyl and pyrimidyl (where pyridyl and pyrimidyl for their part may be substituted by halogen, alkyl, haloalkyl, alkoxy and haloalkoxy), a represents a number from the group consisting of 0, 1, 2 and 3, D represents a heteroaryl radical from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyrid-2-yl, pyrid-3-yl, pyrimid-2-yl, pyrimid-4-yl, imidazolyl, pyrazol-1-yl, pyrazol-3-yl pyrazinyl, 1,2,3-triazinyl, 1,2,4-triazinyl, 1,3,5-triazinyl, thiazol-2-yl, thiazol-4-yl 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl and oxazolyl), $R^3$ represents a radical from the group consisting of cycloalkylalkyl, alkoxycarbonylalkyl, alpha-hydroxyimino-alkoxycarbonylalkyl, alpha-alkoxyimino-alkoxycarbonylalkyl, $C(X)NR^5R^6$, (in which X represents sulphur or NOH, $R^5$ represents hydrogen or alkyl and $R^6$ represents a radical from the group consisting of hydrogen, alkyl, haloalkyl, cyanoalkyl, alkynyl, cycloalkyl, cycloalkylalkyl, alkoxyalkyl, alkoxycarbonyl, alkoxycarbonylalkyl, alkylthioalkyl, aryl (in particular phenyl), arylalkyl (in particular benzyl) and hetarylalkyl (in particular 2-pyrimidylmethyl) or X represents sulphur, NOH or oxygen and $R^5$ and $R^6$ together with the nitrogen atom to which they are attached form a ring which optionally contains one or more further heteroatoms from the group consisting of nitrogen, oxygen and sulphur), $NR^7R^8$ (in which $R^7$ represents hydrogen or alkyl and $R^8$ represents alkynyl, cycloalkylalkyl, alkoxy, haloalkoxy, alkoxycarbonylalkyl, alkylthioalkyl, arylalkyl or hetarylalkyl or $R^7$ and $R^8$ together with the nitrogen atom to which they are attached form a ring which optionally contains one or more further heteroatoms from the group consisting of nitrogen, oxygen and sulphur), the heterocyclyl radicals dioxanyl, dioxolanyl, morpholinyl, triazolinonyl, oxazolinyl, dihydrooxadiazinyl, dihydrodioxazinyl and pyrazolinonyl (which for their part may be substituted by alkyl, haloalkyl, alkoxy and alkoxyalkyl), phenyl (which for its part may be substituted by halogen, cyano, nitro, alkyl and haloalkyl), the heteroaryl radicals pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, alkyl, haloalkyl, alkoxy, haloalkoxy, alkoxyalkyl, alkylthio, alkylthioalkyl and cycloalkyl) and the heteroarylalkyl radicals triazolylalkyl, pyridylalkyl, pyrimidylalkyl and oxadiazolylalkyl (which for their part may be substituted by alkyl), b represents a number from the group consisting of 1, 2 and 3, E represents aryl, in particular phenyl, $R^4$ represents a radical from the group consisting of halogen, cyano, alkyl, haloalkyl, alkoxy, haloalkoxy, dioxolanyl or dihydrodioxazinyl and c represents a number from the group consisting of 0, 1, 2 and 3, and also salts, metal complexes and N-oxides thereof.

Preference is also given to novel compounds of the formula (I) in which $G^1$ represents N, CH or C-halogen, $R^1$ represents hydrogen or $C_1$-$C_6$-alkyl and $G^2$ represents A-$R^2_a$, D-$R^3_b$ or E-$R^4_c$ in which A represents heterocyclyl from the group consisting of oxazolin-2-yl, 5,6-dihydro-[1,3,4]-oxadiazin-2-yl, 5,6-dihydro-[1,3,4]-thiadiazin-2-yl, 5,6-dihydro-[1,4,2]-dioxazin-3-yl and hydroxypyridyl, $R^2$ represents a radical from the group consisting of halogen, cyano, nitro, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-haloalkylsulphinyl, $C_1$-$C_6$-haloalkylsulphonyl, amino, $C_1$-$C_6$-alkylamino, di-($C_1$-$C_6$-alkyl)amino, $C_1$-$C_6$-alkylcarbonylamino, $C_1$-$C_6$-alkoxycarbonylamino, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-alkynyl, $C_3$-$C_6$-cycloalkyl-$C_1$-$C_6$-alkyl, $C_1$-$C_6$-alkylcarbonyl, $C_1$-$C_6$-alkoxycarbonyl, aminocarbonyl, pyridyl and pyrimidyl (where pyridyl and pyrimidyl for their part may be substituted by halogen, $C_1$-$C_6$-alkyl, $C_1$-$C_6$-haloalkyl, $C_1$-$C_6$-alkoxy and $C_1$-$C_6$-haloalkoxy), a represents a number from the group consisting of 0, 1, 2 and 3, D represents a heteroaryl radical from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl (in particular pyrid-2-yl, pyrid-3-yl, pyrimid-2-yl, pyrimid-4-yl, imidazolyl, pyrazol-1-yl, pyrazol-3-yl pyrazinyl, 1,2,3-triazinyl, 1,2,4-triazinyl, 1,3,5-triazinyl, thiazol-2-yl, thiazol-4-yl 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl and oxazolyl), R³ represents a radical from the group consisting of $C_3$-$C_6$-cycloalkyl-$C_1$-$C_6$-alkyl, $C_1$-$C_6$-alkoxycarbonyl-$C_1$-$C_6$-alkyl, alpha-hydroxyimino-$C_1$-$C_6$-alkoxycarbonylmethyl, alpha-$C_1$-$C_6$-alkoxyimino-$C_1$-$C_6$-alkoxycarbonylmethyl, C(X)NR⁵R⁶, (in which X represents sulphur or NOH, R⁵ represents hydrogen or $C_1$-$C_6$-alkyl and R⁶ represents a radical from the group consisting of hydrogen, $C_1$-$C_6$-alkyl, $C_1$-$C_6$-haloalkyl, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy-$C_1$-$C_6$-alkyl, $C_1$-$C_6$-alkoxycarbonyl-$C_1$-$C_6$-alkyl, $C_1$-$C_6$-alkylthio-$C_1$-$C_6$-alkyl, phenyl-$C_1$-$C_6$-alkyl and hetaryl-$C_1$-$C_6$-alkyl in which hetaryl represents pyrimidyl or X represents sulphur, NOH or oxygen and R⁵ and R⁶ together with the nitrogen atom to which they are attached form a 5- to 7-membered ring which may contain one or more further heteroatoms from the group consisting of nitrogen, oxygen and sulphur), NR⁷R⁸ (in which R⁷ represents hydrogen or $C_1$-$C_6$-alkyl and R⁸ represents a radical from the group consisting of $C_2$-$C_6$-alkynyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkoxycarbonyl-$C_1$-$C_6$-alkyl, $C_1$-$C_6$-alkylthio-$C_1$-$C_6$-alkyl, phenyl-$C_1$-$C_6$-alkyl and hetaryl-$C_1$-$C_6$-alkyl in which hetaryl represents pyrimidyl or R⁷ and R⁸ together with the nitrogen atom to which they are attached form a 5- to 7-membered ring which may contain one further heteroatom from the group consisting of nitrogen, oxygen and sulphur), the heterocyclyl radicals dioxanyl, dioxolanyl, morpholinyl, triazolinonyl, oxazolinyl, dihydrooxadiazinyl, dihydrodioxazinyl and pyrazolinonyl (which for their part may be substituted by $C_1$-$C_6$-alkyl, $C_1$-$C_6$-haloalkyl, $C_1$-$C_6$-alkoxy and $C_1$-$C_6$-alkoxy-$C_1$-$C_6$-alkyl), phenyl (which for its part may be substituted by halogen, cyano, nitro, $C_1$-$C_6$-alkyl and $C_1$-$C_6$-haloalkyl), the heteroaryl radicals pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl and $C_3$-$C_6$-cycloalkyl) and the heteroarylalkyl radicals triazolyl-$C_1$-$C_6$-alkyl, pyridyl-$C_1$-$C_6$-alkyl, pyrimidyl-$C_1$-$C_6$-alkyl and oxadiazolyl-$C_1$-$C_6$-alkyl (which for their part may be substituted by $C_1$-$C_6$-alkyl), b represents a number from the group consisting of 1, 2 and 3,
E represents phenyl,
R⁴ represents a radical from the group consisting of halogen, cyano, $C_1$-$C_6$-alkyl, $C_1$-$C_6$-haloalkyl, $C_1$-$C_6$-alkoxy, $C_1$-$C_6$-haloalkoxy, dioxolanyl and dihydrodioxazinyl and
c represents a number from the group consisting of 0, 1, 2 and 3.

Particular preference is also given to novel compounds of the formula (I) in which
G¹ represents N, CH or C-halogen,
R¹ represents hydrogen and
G² represents A-R²$_a$, D-R³$_b$ or E-R⁴$_c$ in which
A represents heterocyclyl from the group consisting of oxazolin-2-yl, 5,6-dihydro-[1,3,4]-oxadiazin-2-yl 5,6-dihydro-[1,3,4]-thiadiazin-2-yl and 5,6-dihydro-[1,4,2]-dioxazin-3-yl, R² represents a radical from the group consisting of halogen, cyano, nitro, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-alkylsulphonyl, $C_1$-$C_4$-haloalkylsulphinyl, $C_1$-$C_4$-haloalkylsulphonyl, amino, $C_1$-$C_4$-alkylamino, di-($C_1$-$C_4$-alkyl)amino, $C_1$-$C_4$-alkylcarbonylamino, $C_1$-$C_4$-alkoxycarbonylamino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-alkynyl, $C_3$-$C_6$-cycloalkyl-$C_1$-$C_4$-alkyl, $C_1$-$C_4$-alkylcarbonyl, $C_1$-$C_4$-alkoxycarbonyl, aminocarbonyl, pyridyl and pyrimidyl (where pyridyl and pyrimidyl for their part may be substituted by halogen, $C_1$-$C_4$-alkyl, $C_1$-$C_4$-haloalkyl, $C_1$-$C_4$-alkoxy and $C_1$-$C_4$-haloalkoxy), a represents a number from the group consisting of 0, 1, 2 and 3, D represents a heteroaryl radical from the group consisting of pyrid-2-yl, pyrid-3-yl, pyrimid-2-yl, pyrimid-4-yl, imidazolyl, pyrazol-1-yl, pyrazol-3-yl pyrazinyl, 1,2,3-triazinyl, 1,2,4-triazinyl, 1,3,5-triazinyl, thiazol-2-yl, thiazol-4-yl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl and oxazolyl (in particular pyrazol-1-yl, pyrazol-3-yl, pyrid-2-yl, pyrid-3-yl, pyrimid-2-yl, pyrimid-4-yl, thiazol-2-yl and thiazol-4-yl), R³ represents a radical from the group consisting of $C_3$-$C_6$-cycloalkyl-$C_1$-$C_4$-alkyl, $C_1$-$C_4$-alkoxycarbonyl-$C_1$-$C_4$-alkyl, alpha-hydroxyimino-$C_1$-$C_4$-alkoxycarbonylmethyl, alpha-$C_1$-$C_4$-alkoxyimino-$C_1$-$C_4$-alkoxycarbonylmethyl, C(X)NR⁵R⁶, (in which X represents sulphur, R⁵ represents hydrogen or $C_1$-$C_4$-alkyl and R⁶ represents a radical from the group consisting of hydrogen, $C_1$-$C_5$-alkyl, $C_1$-$C_4$-haloalkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkylthio-$C_1$-$C_4$-alkyl or phenyl-$C_1$-$C_4$-alkyl or X represents sulphur or oxygen and R⁵ and R⁶ together with the nitrogen atom to which they are attached form a 5- to 7-membered ring which may contain one further heteroatom from the group consisting of nitrogen, oxygen and sulphur), NR⁷R⁸ (in which R⁷ represents hydrogen or $C_1$-$C_4$-alkyl and R⁸ represents a radical from the group consisting of $C_2$-$C_4$-alkynyl, $C_3$-$C_6$-cycloalkyl-$C_1$-$C_4$-alkyl, $C_1$-$C_4$-alkoxy, $C_1$-$C_4$-haloalkoxy, $C_1$-$C_4$-alkoxycarbonyl-$C_1$-$C_4$-alkyl, $C_1$-$C_4$-alkylthio-$C_1$-$C_4$-alkyl or phenyl-$C_1$-$C_4$-alkyl or R⁷ and R⁸ together with the nitrogen atom to which they are attached form a 5- or 6-membered ring which may contain one further heteroatom from the group consisting of oxygen, sulphur and nitrogen), the heterocyclyl radicals dioxanyl, dioxolanyl, morpholinyl, triazolinonyl, oxazolinyl, dihydrooxadiazinyl, dihydrodioxazinyl and pyrazolinonyl (in particular 1,3-dioxolan-2-yl, 1,3-dioxan-2-yl and 1,2,4-triazolin-3-on-2-yl) (which for their part may be substituted by $C_1$-$C_4$-alkyl and $C_1$-$C_4$-haloalkyl), phenyl (which for its part may be substituted by halogen, cyano, nitro, $C_1$-$C_4$-alkyl or $C_1$-$C_4$-haloalkyl), the heteroaryl radicals pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (which for their part may be substituted by halogen, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cycloalkyl) and the heteroarylalkyl radicals triazolyl-$C_1$-$C_4$-alkyl, pyridyl-$C_1$-

$C_4$-alkyl, pyrimidyl-$C_1$-$C_4$-alkyl and oxadiazolyl-$C_1$-$C_4$-alkyl (which for their part may be substituted by $C_1$-$C_4$-alkyl), b represents a number from the group consisting of 1 and 2, E represents phenyl and $R^4$ represents a radical from the group consisting of halogen, cyano, $C_1$-$C_4$-alkyl, $C_1$-$C_4$-haloalkyl, $C_1$-$C_4$-alkoxy and $C_1$-$C_4$-haloalkoxy and c represents a number from the group consisting of 0, 1 and 2.

Very particular preference is also given to novel compounds of the formula (I) in which $G^1$ represents N, CH or C-halogen (in the case of C-halogen in particular CF and Cl), $R^1$ represents hydrogen, $G^2$ represents A-$R^2_a$ or D-$R^3_b$ in which A represents heterocyclyl from the group consisting of oxazolin-2-yl, 5,6-dihydro-[1,3,4]-thiadiazin-2-yl and 5,6-dihydro-[1,3,4]-oxadiazin-2-yl, $R^2$ represents a radical from the group consisting of pyridyl and pyrimidin-2-yl which may be substituted by halogen, $C_1$-$C_4$-alkyl, $C_1$-$C_4$-haloalkyl, $C_1$-$C_4$-alkoxy and $C_1$-$C_4$-haloalkoxy, a represents 0, 1 or 2 and in particular 1, D represents a heteroaryl radical from the group consisting of pyrazol-1-yl, pyrazol-3-yl, pyrid-2-yl, pyrid-3-yl, pyrimid-2-yl, pyrimid-4-yl, thiazol-2-yl and thiazol-4-yl, $R^3$ represents a radical from the group consisting of $C_3$-$C_6$-cycloalkyl-$C_1$-$C_4$-alkyl (in particular cyclopropylmethyl), alpha-hydroxyimino-$C_1$-$C_4$-alkoxycarbonylmethyl, C(X)NR$^5$R$^6$, (in which X represents sulphur, $R^5$ represents hydrogen and $R^6$ represents a radical from the group consisting of hydrogen, $C_1$-$C_5$-alkyl (in particular methyl, ethyl, n-propyl, isopropyl, isobutyl, tert-butyl, $C_1$-$C_4$-haloalkyl (in particular $CF_3CH_2$), cyano-$C_1$-$C_4$-alkyl (in particular $NCCH_2CH(C_2H_5)$, $C_3$-$C_6$-cycloalkyl (in particular cyclopropyl, cyclopentyl, cyclohexyl), $C_3$-$C_6$-cycloalkyl-$C_1$-$C_4$-alkyl (in particular cyclopropylmethyl), $C_1$-$C_4$-alkoxy-$C_1$-$C_4$-alkyl (in particular $CH_3OCH_2CH(CH_3)$, $CH_3CH_2CH_2OCH_2CH(CH_3)$, $CH_3CH_2OCH_2CH_2$, $CH_3OCH_2CH_2CH_2$, $CH_3OCH_2CHC_2H_5$, $CH_3CH_2OCH_2CH(CH_3)$, $CH_3CH_2OCH_2CH_2CH_2$, $CH_3OC(CH_3)$, $C_1$-$C_4$-alkylthio-$C_1$-$C_4$-alkyl (in particular $CH_3SCH_2CH_2$) and phenyl-$C_1$-$C_4$-alkyl (in particular $C_6H_5CH(CH_3)$ or X represents sulphur or oxygen and $R^5$ and $R^6$ together with the nitrogen atom to which they are attached form a 5- to 7-membered ring which optionally contains a further heteroatom from the group consisting of nitrogen, oxygen and sulphur (in particular, $R^5$ and $R^6$ together represents $(CH_2)_4$, $(CH_2)_5$ or $(CH_2)_2O(CH_2)_2)$), $NR^7R^8$ (in which $R^7$ represents hydrogen or methyl and $R^8$ represents $C_1$-$C_4$-alkoxycarbonyl-$C_1$-$C_4$-alkyl (in particular $CH_2CO_2CH_3$) or $R^7$ and $R^8$ together with the nitrogen atom to which they are attached form a 5- or 6-membered ring which may contain an oxygen atom, for example, stehen $R^7$ and $R^8$ together represent $(CH_2)_4$, $(CH_2)_5$ or $(CH_2)_2O(CH_2)_2)$, the heterocyclyl radicals dioxanyl, dioxolanyl, morpholinyl, triazolinonyl, oxazolinyl, dihydrooxadiazinyl, dihydrodioxazinyl and pyrazolinonyl (in particular 1,3-dioxolan-2-yl, 1,3-dioxan-2-yl and 1,2,4-triazolin-3-on-2-yl) (which for their part may be substituted by $C_1$-$C_4$-alkyl (in particular methyl) and $C_1$-$C_4$-haloalkyl (in particular $CF_3$)), phenyl (which for its part may be substituted by halogen (in particular fluorine and chlorine), the heteroaryl radicals pyridyl, pyridyl N-oxide, pyrimidinyl, pyrazolyl, thiazolyl, furanyl, thienyl, triazolyl, oxadiazolyl, thiadiazolyl, pyrazinyl, triazinyl, and isoquinolinyl (which for their part may be substituted by halogen (in particular fluorine and chlorine), nitro, $C_1$-$C_4$-alkyl (in particular methyl, ethyl, n-propyl, isopropyl and tert-butyl), $C_1$-$C_4$-haloalkyl (in particular $CF_3$, $CHF_2$ and CFClH), $C_1$-$C_4$-alkoxy (in particular methoxy and ethoxy), $C_3$-$C_6$-cycloalkyl (in particular cyclopropyl, cyclobutyl and cyclopentyl)), the heteroarylalkyl radicals triazolyl-$C_1$-$C_4$-alkyl (in particular triazolylmethyl), pyridyl-$C_1$-$C_4$-alkyl (in particular pyridylmethyl), pyrimidinyl-$C_1$-$C_4$-alkyl (in particular pyrimidinylmethyl) or oxadiazolyl-$C_1$-$C_4$-alkyl (in particular oxadiazolylmethyl (which for their part may be substituted by $C_1$-$C_4$-alkyl (in particular methyl)) and b represents 1 or 2 and in particular represents 1.

The number of substituents determined by a and b may be limited by the number of substitutable hydrogen atoms at the radicals A, D and E.

Preference according to the invention is given to compounds of the formula (I) which contain a combination of the meanings listed above as being preferred.

Particular preference according to the invention is given to compounds of the formula (I) which contain a combination of the meanings listed above as being particularly preferred.

Very particular preference according to the invention is given to compounds of the formula (I) which contain a combination of the meanings listed above as being very particularly preferred.

In an emphasized group of novel compounds of the formula (I), $G^1$ represents CH.

In a further emphasized group of novel compounds of the formula (I), $G^1$ represents N.

In a further emphasized group of novel compounds of the formula (I), $G^1$ represents C-halogen.

In a further emphasized group of novel compounds of the formula (I), $G^1$ represents CH and $R^1$ represents hydrogen.

In a further emphasized group of novel compounds of the formula (I), $G^1$ represents N and $R^1$ represents hydrogen.

In a further emphasized group of novel compounds of the formula (I), $G^1$ represents C-halogen and $R^1$ represents hydrogen.

In a further emphasized group of novel compounds of the formula (I), $G^1$ represents CH and $R^1$ represents methyl.

In a further emphasized group of novel compounds of the formula (I), $G^1$ represents N and $R^1$ represents methyl.

In a further emphasized group of novel compounds of the formula (I), $G^1$ represents C-halogen and $R^1$ represents methyl.

In a further emphasized group of novel compounds of the formula (I), $G^2$ represents D-$R^3_b$.

In a further emphasized group of novel compounds of the formula (I), $G^2$ represents D-$R^3_b$ and b represents 1.

Depending on the nature of the substituents, the compounds of the formula (I) can be present as geometrical and/or as optically active isomers or corresponding isomer mixtures of varying composition. The invention relates both to the pure isomers and to the isomer mixtures.

The invention also relates to salts, N-oxides and metal complexes of the compounds of the formula (I).

By way of example and in a complementary manner, the preparation of compounds of the formula (I) is illustrated in the formula Schemes below. Reference may also be made here to the Preparation Examples. In the schemes, the radicals $G^1$ and $G^2$ may also be written as $G_1$ and $G_2$.

Formula Scheme 1

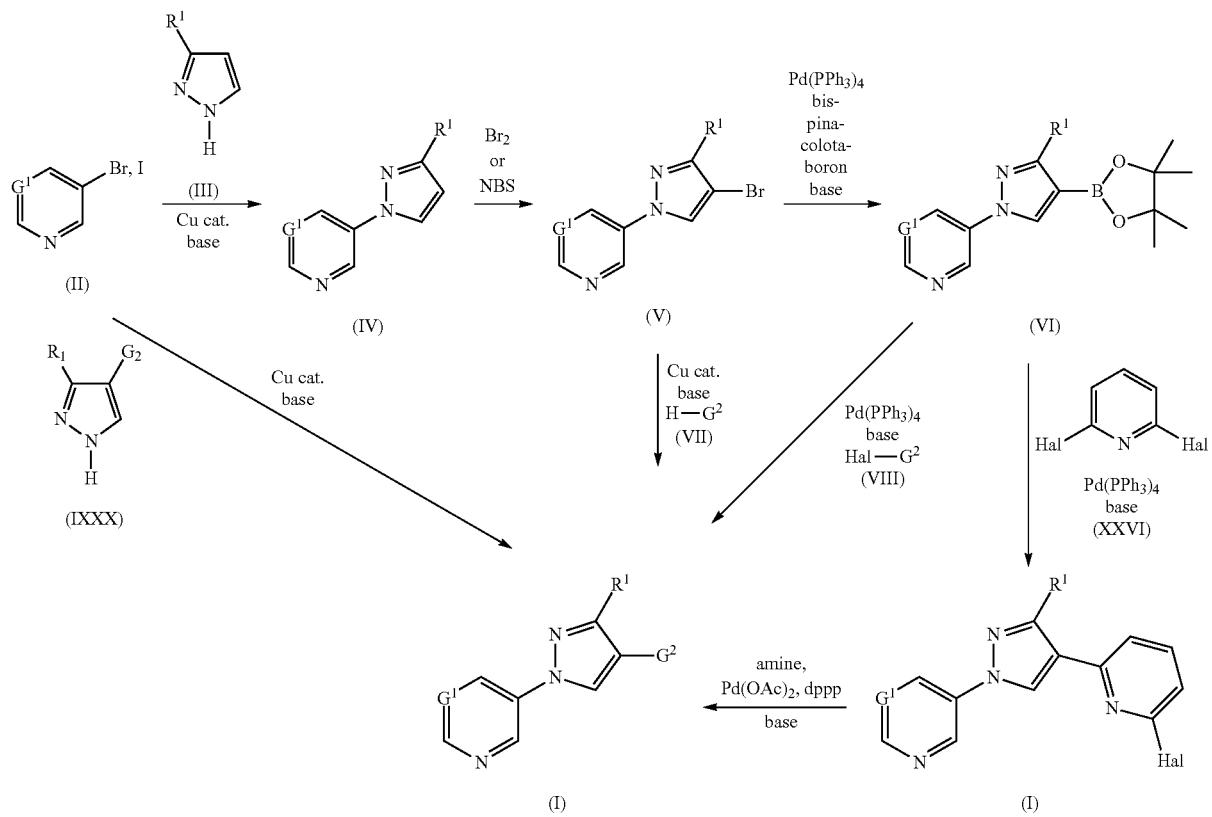

The preparation of compounds of the formula (I) according to the invention starts with 3-halopyridines of the formula (II); for example, by reacting a bromide of the formula (II) with a pyrazole of the formula (III) in the presence of a copper catalyst and an auxiliary base such as potassium carbonate, the compounds of the formula (IV) are obtained. See, for example, for 3-(4-bromopyrazol-1-yl)pyridine: Journal of Heterocyclic Chemistry 1981, 18, 9-14; European Journal of Organic Chemistry, 2004, 695. By reaction with bromine or N-bromosuccinimide, these pyrazoles of the formula (IV) afford the bromides of the formula (V). See, for example, for 3-(4-bromopyrazol-1-yl)pyridine: Journal of Heterocyclic Chemistry 18, 1981, 9-14. The bromides of the formula (V) give, by reaction with bis-pinacolata-diboron in the presence of a palladium catalyst and an auxiliary base, the boronic esters of the formula (VI). The compounds of the formula (I) according to the invention can be obtained from the bromides of the formula (V) or from the halides of the formula (II) by reaction with a compound of the formula (VII), which represents a building block H-G$^2$ which contains an N—H, such as, for example, a 3-hetarylpyrazole, in the presence of a copper catalyst and an auxiliary base or by the same process by reaction of the bromides of the formula (II) with a suitable pyrazole of the formula (IXXX). Furthermore, the halopyridines of the formula (I) can be obtained by reaction of the boronic esters of the formula (VI) with a dihalopyridine of the formula (XXVI) in the presence of a palladium catalyst and an auxiliary base (Suzuki reaction). The reaction of the halopyridines of the formula (I) with amines in the presence of a palladium catalyst and an auxiliary base subsequently affords, analogously to the method described in Journal of Organic Chemistry 72, 2007, 3606-3607, those compounds of the formula (I) according to the invention which carry the corresponding amine in G$^2$ (dppp=1,3-bis(diphenylphosphino)propane).

In addition, the compounds of the formula (I) according to the invention can be obtained by reacting the boronic esters of the formula (VI) with a halide of the formula (VIII) in the presence of a palladium catalyst and an auxiliary base (Suzuk reaction).

The compounds of the formulae (VII) and (IIX) required are known or can be prepared by methods known in principle; see the references listed in an exemplary manner below.

2-(6-Bromopyridin-2-yl)pyrimidine is described in Tetrahedron Letters, 2000, 1653, an improved preparation process results when the observations described in Tetrahedron Letters 1996, 2537 are taken into account.

For N,N-dimethyl-6-bromopyridine-2-carboxamide, see Journal of the Chemical Society, Perkin 1, 16, 1996, 1927-1934.

For (6-bromopyridin-2-yl)morpholin-4-yl-methanone, see WO 2006/65209.

For 2-bromo-6-pyrazol-1-ylpyridine, see Journal of Organic Chemistry, 1990, 4992-4994.

For tert-butyl (6-bromopyridin-2-yl)carbamate, see Journal of Medicinal Chemistry, 2005, 1886-1900.

For methyl [(6-bromopyridin-2-yl)methylamino]acetate, see U.S. Pat. No. 5,008,275.

For 2-bromo-6-methoxypyridine, see Journal of the American Chemical Society 1994, 3657-3658.

For 5-(6-bromopyridin-2-yl)-1H-pyrimidine-2,4-dione, see Journal of Heterocyclic Chemistry 32, 4, 1995, 1159-1164.

For 2-(1H-pyrazol-4-yl)pyridine, see Journal of Medicinal Chemistry, 2004, 4645-4648.

For 3-(1H-pyrazol-4-yl)pyridine, see Angewandte Chemie Int. Ed. 2006, 1282-1284.

For [(Z)-3-dimethylamino-2-(4-trifluoromethylphenyl)al-lylidene]dimethylammonium perchlorate, see Bioorganic and Medicinal Chemistry 2008, 2463-2472.

For [(Z)-3-dimethylamino-2-(3-trifluoromethylphenyl)al-lylidene]dimethylammonium perchlorate, see Journal of Organic Chemistry 1995, 3750.

For (Z)-3-hydroxy-2-(4-methoxyphenyl)propenal, see Journal of Heterocyclic Chemistry 11, 1974, 51, 52.

For (Z)-3-hydroxy-2-pyrazin-2-ylpropenal, see Tetrahedron Letters 49, 2, 2008, 305-310.

For (Z)-3-hydroxy-2-pyridin-4-ylpropenal, see Tetrahedron Letters 49, 2, 2008, 305-310.

For 4-(4-chlorophenyl)-1H-pyrazole, see Synthetic Communications 17, 2, 1987, 165-172 or Journal of Organic Chemistry, 1991, 976; Journal of Heterocyclic Chemistry 28, 1991, 1281-1285.

Taking into account the observations described in WO 2004/37808, 2-bromo-6-(dimethoxymethyl)pyridine is synthesized from 6-bromopyridine-2-carbaldehyde.

Using the methods described in WO 2008/104077, 2-bromo-6-(3,5-dimethyl-1H-pyrazol-1-yl)pyridine is synthesized from 6-chloro-2-pyridyl)hydrazine and 2,4-pentadione.

Using the methods described in Journal of Fluorine Chemistry 53, 1991 143-153, 2-chloro-6-(2,2,2-trifluoroethoxy) pyridine is synthesized from 2,6-dichloropyridine.

Taking into account the observations described in WO 2003/93231, 2-bromo-5-(1,1-difluoroethyl)pyridine is synthesized from 1-(6-bromopyridin-3-yl)ethanone using diethylaminosulphur trifluoride (DAST).

2-(6-Bromopyridin-2-yl)-4-methyl-5-(trifluoromethyl)-2,4-dihydro-3H-1,2,4-triazol-3-one can be prepared from 4-methyl-5-(trifluoromethyl)-2,4-dihydro-3H-1,2,4-triazol-3-one by copper diamine-catalyzed N-arylation. The synthesis was carried out analogously to the method described in Journal of Organic Chemistry 69, 2004, 5578-5587.

Formula Scheme 2:

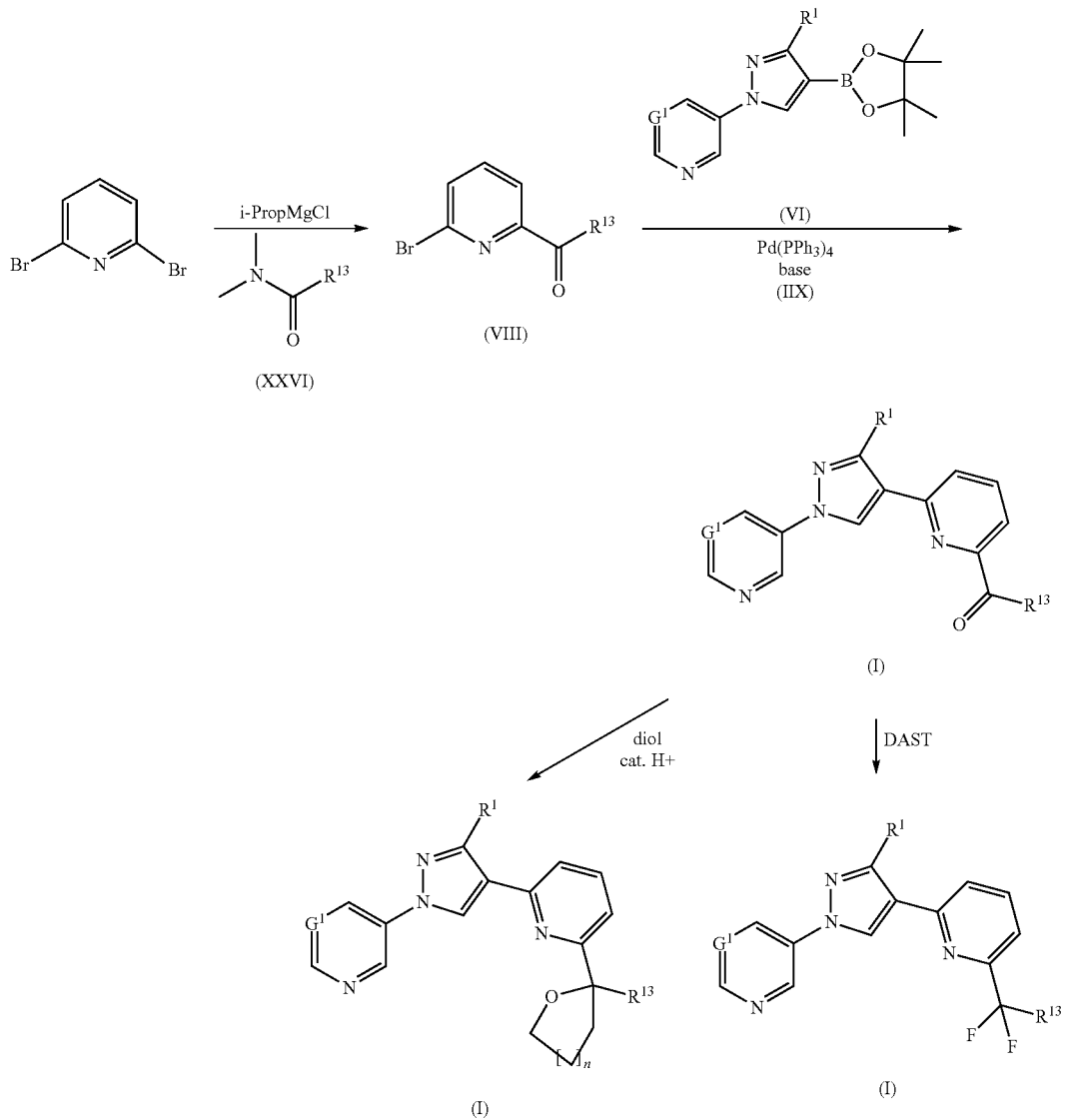

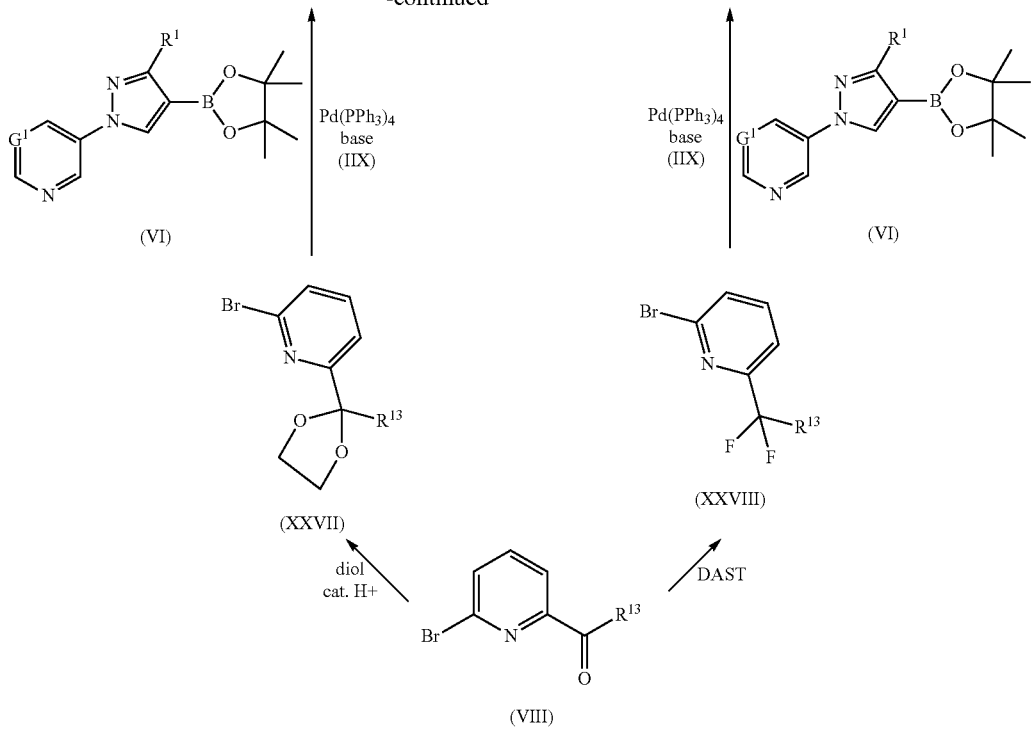

Certain compounds of the formula (VIII) of type Hal-G² required for the process described in Formula Scheme 1 can be obtained according to Formula Scheme 2 and be converted into the compounds of the formula (I) according to the invention having a group $R^{13}$ which forms part of the group $R^3$. 2,6-Dibromopyridine is metallated, for example, by reaction with isopropylmagnesium chloride, see Tetrahedron 2000, 1349; Tetrahedron Letters 1999, 4339; and converted with an acylating agent such as the dimethylamides of the formula (XXVI) into the ketones of the formula (VIII). The dimethylamides of the formula (XXVI) are known or can be prepared by methods known in principle, see for example 2-methoxy-N,N-dimethylacetamide, for example, DE 875807; Journal of Organic Chemistry 1974, 1233.

In accordance with the process described in Formula Scheme 1, the ketones of the formula (VIII) give, by reaction with the boronic esters of the formula (VI) in a transition metal-catalyzed reaction (for example a Suzuki reaction) the ketones of the formula (I) from which it is possible, by reaction with a diol under acid catalysis and removal of water, to obtain the ketals of the formula (I), or, by reaction with a fluorinating agent such as DAST, to obtain the fluorinated compounds of the formula (I), see WO 2003/93231.

Reaction of ketones of the formula (VIII) with a diol under acid catalysis and removal of water affords the ketals of the formula (XXVII) which, by reaction with the boronic esters of the formula (VI) in a transition metal-catalyzed reaction (for example a Suzuki reaction), give the ketals of the formula (I). The reaction of ketones of the formula (VIII) with a fluorinating agent such as DAST affords the fluorinated compounds of the formula (XXVIII) which can be used to obtain, by reaction with the boronic esters of the formula (VI) in a transition metal-catalyzed reaction (for example a Suzuki reaction), the fluorinated compounds of the formula (I), see WO 2003/93231.

Formula Scheme 3

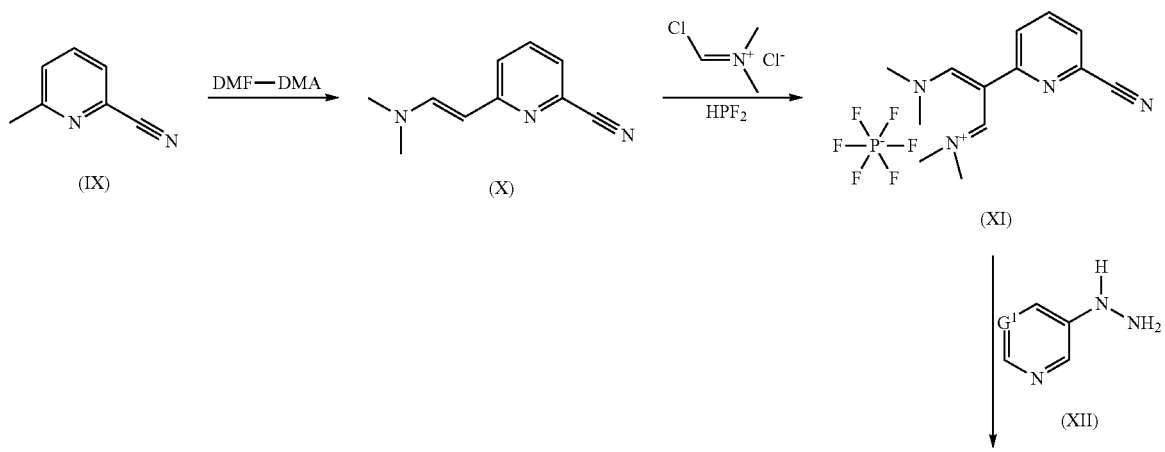

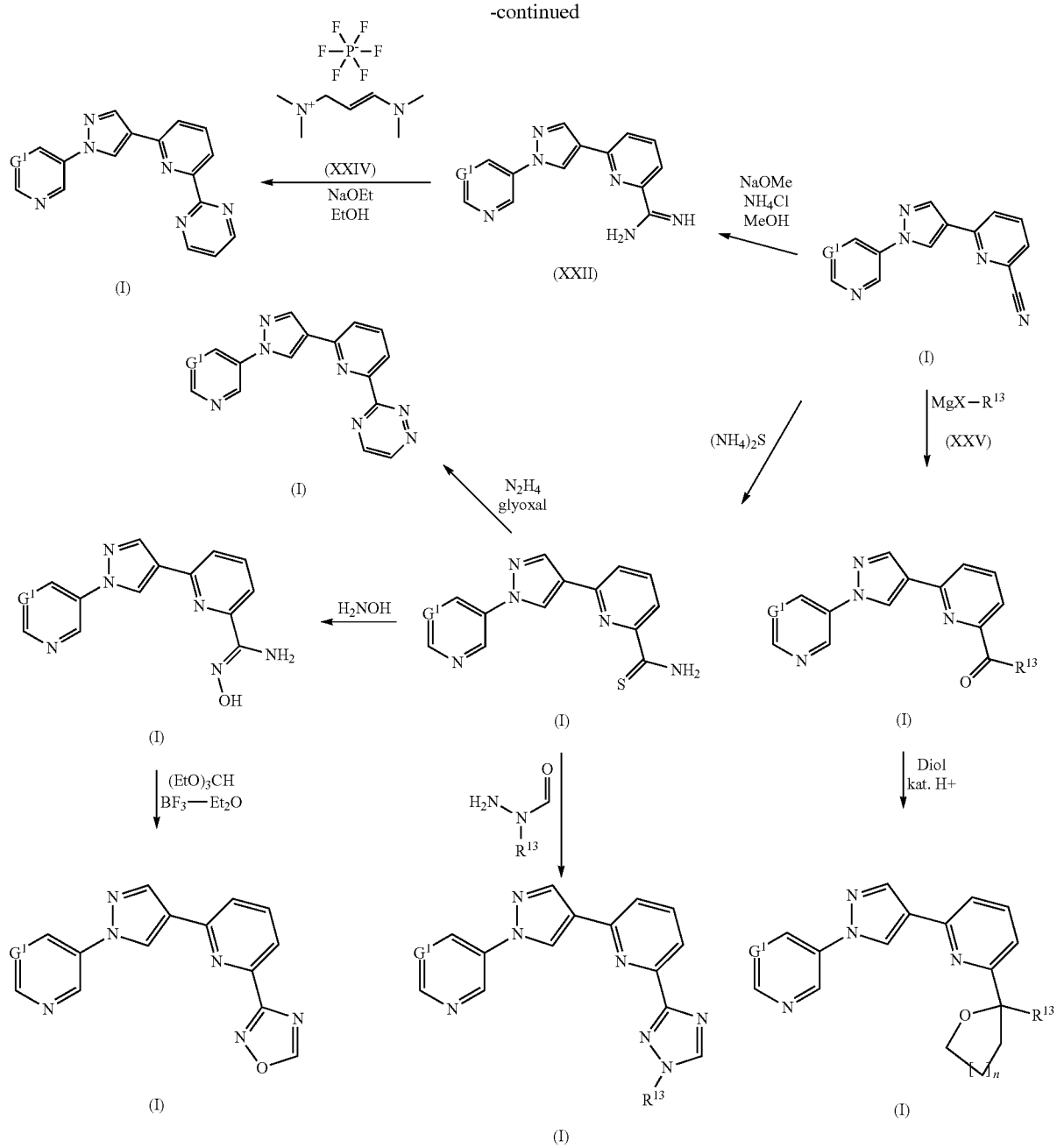

As an alternative to the process described in Formula Scheme 1, the compounds of the formula (I) according to the invention can also be obtained in accordance with Formula Scheme 3. 6-Methylpyridine-2-carbonitrile (IX) is known, see, for example, EP 1 424 336 or Chem. Pharm Bull. 7, 1959, 925. Reaction with dimethylformamide dimethyl acetal gives the enamine (X), see U.S. Pat. No. 4,176,183 and Synthesis 1997, 696. Reaction with chloromethylenedimethylammonitu chloride, the Vilsmeier reagent, see Organic Synthesis, 1987, 121, affords the vinamidinium salt (XI), again see Synthesis 1997, 696. This gives, by reaction with pyridylhydrazines of the formula (XII), the nitriles of the formula (I); a reaction of this type is described in Tetrahedron Letters 1996, 1829. Pyridylhydrazines of the formula (XII) are known or can be prepared by methods known in principle, see, for example, EP 1 426 366 or Liebigs Annalen 486, 1931, 95.

The nitriles of the formula (I) are reacted with ammonium sulphide to give the thioamides of the formula (I). The thioamides yield, by reaction with hydrazine and glyoxal, the triazines of the formula (I), see Chemische Berichte 101, 1968, 3952-3956; European Journal of Organic Chemistry 1999, 313-321; the amidrazone is formed as an intermediate, see Chemical Reviews 1970, 70(1), 151-170. The thioamides of the formula (I) give, by reaction with formhydrazides, see Chemische Berichte 1965, 3377, the triazoles of the formula (I).

From the thioamides of the formula (I), it is possible, by reaction with hydroxylamine, to obtain the hydroxamic acids of the formula (I), see Journal of Heterocyclic Chemistry 1980, 819-821; these are reacted with orthoesters to give the oxdiazoles of the formula (I), see Journal of Medicinal Chemistry 1994, 2421-2436.

By reaction with sodium alkoxide and ammonium chloride, it is possible to obtain, from the nitriles of the formula (I), the amidines of the formula (XXII), from which, as an alternative to the process described in Formula Scheme 1, it is possible to obtain the pyrimidines of the formula (I) by reaction with a vinamidinium salt of the formula (XXIV). The vinamidinium salts of the formula (XXIV) required are known or can be obtained by methods known in principle, see Journal of Organic Chemistry, 1960, 3812; Collect. Czech. Chem. Comm. Vol 61, 1996, 1637.

From the nitriles of the formula (I), it is possible to obtain, as an alternative to the process described in Formula Scheme 2, by reaction with an organometallic reagent of the formula (XXV) such as, for example a Gringnard compound, the ketones of the formula (I), see Journal of Heterocyclic Chemistry 1999, 81 and Journal of Organic Chemistry 1987, 3901. These ketones afford, by reaction with diols under acid catalysis and with removal of water, the ketals of the formula (I).

Formula Scheme 4

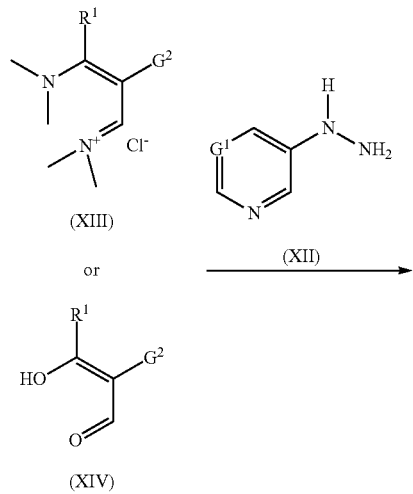

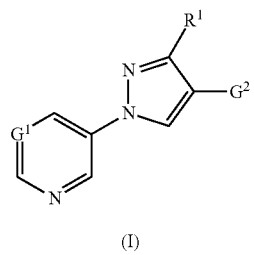

As an alternative to the processes described in Formula Schemes 1 and 2, the compounds of the formula (I) according to the invention can also be obtained in a more general manner in accordance with Formula Scheme 4. To this end, the vinamidinium salts of the formula (XIII) or the dialdehyds or enolaldehydes of the formula (XIV) are reacted with the pyridylhydrazines of the formula (XII) to give to compounds of the formula (I) according to the invention. The compounds of the formulae (XIII) and (XIV) are known or can be obtained by methods known in principle, see, for example, Journal of Heterocyclic Chemistry 28, 1991, 1281; Angewandte Chemie 1976, 496.

Formula Scheme 5

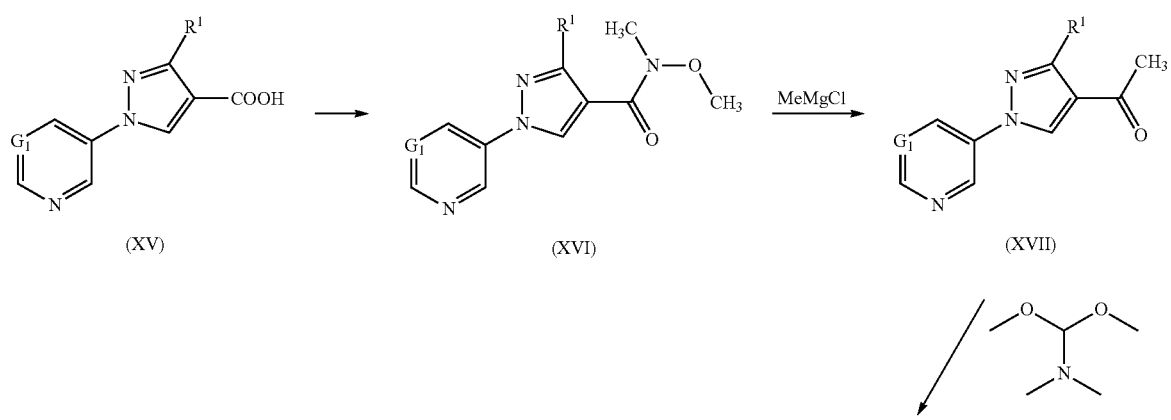

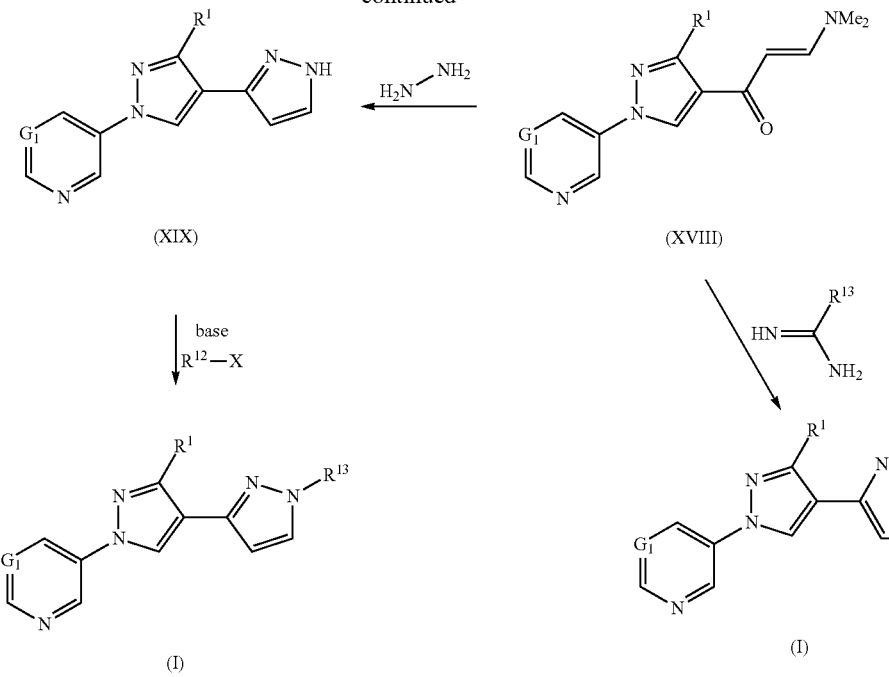

In accordance with Formula Scheme 5, it is possible to obtain those compounds of the formula (I) according to the invention which carry a pyrazole or pyrimidine in the radical $G^2$. The pyrazolecarboxylic acids of the formula (XV) are known or can be prepared by methods known in principle. For example, 1-(pyridin-3-yl)-1H-pyrazole-4-carboxylic acid is obtained by alkaline ester hydrolysis from the corresponding ethyl ester, the preparation of which is described in Journal of Organic Chemistry 2004, 5578. The acids of the formula (XV) are then converted with a chlorinating agent such as thionyl chloride into the corresponding acid chlorides. Further reaction with O,N-dimethyl-hydroxylamine in a diluent such as, for example, dichloromethane or tetrahydrofuran and in the presence of a base such as, for example, triethylamine or diisopropylethylamine, leads to the amides of the formula (XVI) which can be converted by reaction with a methylmetal compound such as methylmagnesium chloride into the ketones of the formula (XVII). By reacting the compounds of the formula (XVII) with dimethylformamide dimethyl acetal, the enaminones of the formula (XVIII) are obtained, see Heterocycles, 43, 1, 1996, 221 and Journal of Heterocyclic Chemistry 24, 1987, 837.

The enaminones of the formula (XVIII) give, by reaction with hydrazine hydrate in a diluent such as ethanol, the NH-pyrazoles of the formula (XIX). These pyrazoles can be converted by reaction with an alkylating or (het)arylating agent and an auxiliary base such as sodium hydride in a diluent such as DMF into the pyrazoles of the formula (I) according to the invention.

The pyrimidines of the formula (I) according to the invention can be obtained by reacting the enaminones of the formula (XVIII) with amidines in the presence of an auxiliary base such as sodium ethoxide in a diluent such as ethanol. The amidines required are known or can be prepared by methods known in principle.

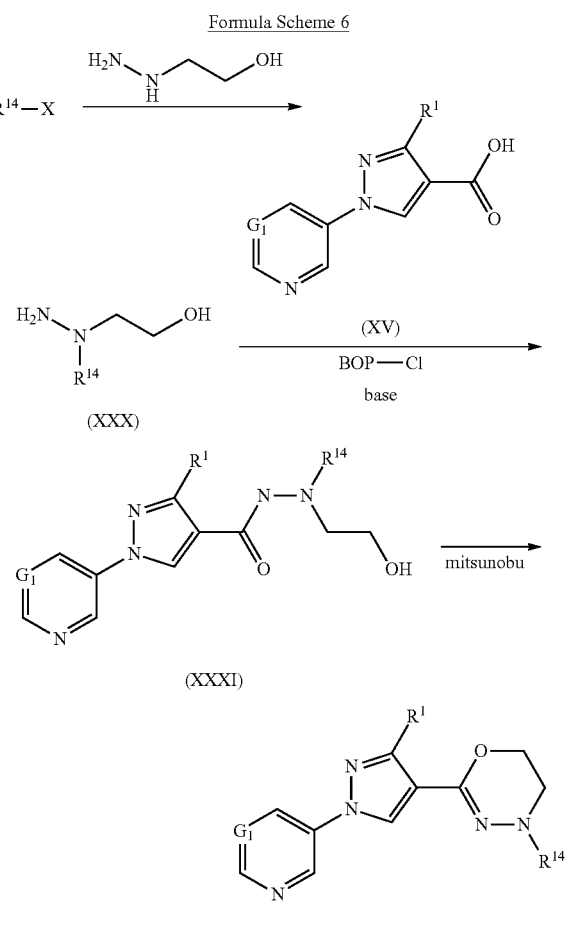

The dihydrooxdiazines of the formula (I) according to the invention having a group $R^{14}$ which forms part of the group $R^2$ are obtained in accordance with Formula Scheme 6 by initially reacting 2-hydrazinoethanol with an alkylating or (het)arylating agent $R^{14}$—X to give compounds of the formula (XXX); a reaction of this type is described in Khim. Geterosikl. Soedin 1990, 8, 1065.

These can be used to obtain, using acids of the formula (XV) with the aid of an activating agent such as bis(2-oxo-3-oxazolidinyl)phosphinyl chloride (BOP-Cl) or the corresponding acid chlorides in the presence of an auxiliary base such as triethylamine in a diluent such as DMF, the hydrazides of the formula (XXXI) which, for example in a Mitsunobu reaction as described in Heterocycles 37, 3, 1994, 1645, can be converted into the dihydrooxdiazines of the formula (I) according to the invention.

The intermediates below are novel and also form part of the subject matter of the invention.

Compounds of the Formula (VI)

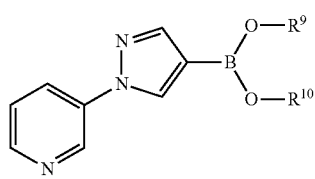

in which
$R^9$ and $R^{10}$ independently of one another represent H, $C_1$-$C_6$-alkyl (in particular methyl, ethyl, propyl and isopropyl) or, if appropriate, together with the atoms to which they are attached, a ring which preferably does not contain any further heteroatoms and which for its part may be mono- or polysubstituted by $C_1$-$C_6$-alkyl (in particular methyl, ethyl, propyl, isopropyl).

Compounds of the Formula (X)

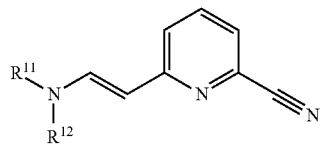

in which
$R^{11}$ and $R^{12}$ represent $C_1$-$C_6$-alkyl (in particular methyl, ethyl, propyl and isopropyl) or, together with the nitrogen atom to which they are attached, form a ring (in particular pyrrolidinyl, piperidinyl and morpholinyl).

Compounds of the Formula (XI)

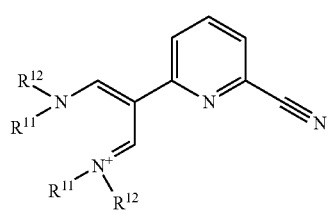

in which
$R^{11}$ and $R^{12}$ represent $C_1$-$C_6$-alkyl (in particular methyl, ethyl, propyl and isopropyl) or, together with the nitrogen atom to which they are attached, form a ring (in particular pyrrolidinyl, piperidinyl and morpholinyl)
in the form of salts, in particular from the group consisting of -hexafluorophosphate, -perchlorate, -hydrochloride, -oxalate and -tetrafluoroborate.

Compound of the Formula

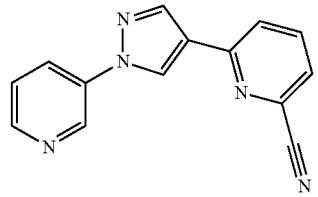 [SMILES: N#Cc1cccc(-c2cnn(-c3cccnc3)c2)n1]

Compound of the Formula

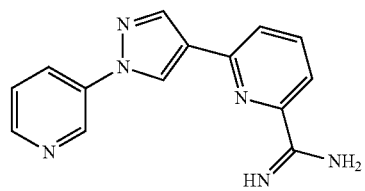 [SMILES: N=C(N)c1cccc(-c2cnn(-c3cccnc3)c2)n1]

also in the form of their salts, in particular as amidinium hydrochloride and amidinium sulphate.

The known and novel active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products, and of materials, and in the hygiene sector. They may be preferably employed as plant protection agents. They are active against normally sensitive and resistant species and against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus* spp., *Aceria sheldoni*, *Aculops* spp., *Aculus* spp., *Amblyomma* spp., *Amphitetranychus viennensis*, *Argas* spp., *Boophilus* spp., *Brevipalpus* spp., *Bryobia praetiosa*, *Chorioptes* spp., *Dermanyssus gallinae*, *Eotetranychus* spp., *Epitrimerus pyri*, *Eutetranychus* spp., *Eriophyes* spp., *Halotydeus destructor*, *Hemitarsonemus* spp., *Hyalomma* spp., *Ixodes* spp., *Latrodectus mactans*, *Metatetranychus* spp., *Nuphersa* spp., *Oligonychus* spp., *Ornithodoros* spp., *Panonychus* spp., *Phyllocoptruta oleivora*, *Polyphagotarsonemus latus*, *Psoroptes* spp., *Rhipicephalus* spp., *Rhizoglyphus* spp., *Sarcoptes* spp., *Scorpio maurus*, *Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acalymma vittatum, Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apion* spp., *Apogonia* spp., *Atomaria* spp., *Attagenus* spp., *Bruchidius obtectus, Bruchus* spp., *Cassida* spp., *Cerotoma trifurcata, Ceutorrhynchus* spp., *Chaetocnema* spp., *Cleonus mendicus, Conoderus* spp., *Cosmopolites* spp., *Costelytra zealandica, Ctenicera* spp., *Curculio* spp., *Cryptorhynchus lapathi, Cylindrocopturus* spp., *Dermestes* spp., *Diabrotica* spp., *Dichocrocis* spp., *Diloboderus* spp., *Epilachna* spp., *Epitrix* spp., *Faustinus* spp., *Gibbium psylloides, Hellula undalis, Heteronychus arator, Heteronyx* spp., *Hylamorpha elegans, Hylotrupes bajulus, Hypera postica, Hypothenemus* spp., *Lachnosterna consanguinea, Lema* spp., *Leptinotarsa decemlineata, Leucoptera* spp., *Lissorhoptrus oryzophilus, Lixus* spp., *Luperodes* spp., *Lyctus* spp., *Megascelis* spp., *Melanotus* spp., *Meligethes aeneus, Melolontha* spp., *Migdolus* spp., *Monochamus* spp., *Naupactus xanthographus, Niptus hololeucus, Oryctes rhinoceros, Oryzaephilus surinamensis, Oryzaphagus oryzae, Otiorrhynchus* spp., *Oxycetonia jucunda, Phaedon cochleariae, Phyllophaga* spp., *Phyllotreta* spp., *Popillia japonica, Premnotrypes* spp., *Psylliodes* spp., *Ptinus* spp., *Rhizobius ventralis, Rhizopertha dominica, Sitophilus* spp., *Sphenophorus* spp., *Sternechus* spp., *Symphyletes* spp., *Tanymecus* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Diplopoda, for example, *Blaniulus guttulatus*.

From the order of the Diptera, for example, *Aedes* spp., *Agromyza* spp., *Anastrepha* spp., *Anopheles* spp., *Asphondylia* spp., *Bactrocera* spp., *Bibio hortulanus, Calliphora erythrocephala, Ceratitis capitata, Chironomus* spp., *Chrysomyia* spp., *Cochliomyia* spp., *Contarinia* spp., *Cordylobia anthropophaga, Culex* spp., *Cuterebra* spp., *Dacus oleae, Dasyneura* spp., *Delia* spp., *Dermatobia hominis, Drosophila* spp., *Echinocnemus* spp., *Fannia* spp., *Gastrophilus* spp., *Hydrellia* spp., *Hylemyia* spp., *Hyppobosca* spp., *Hypoderma* spp., *Liriomyza* spp., *Lucilia* spp., *Musca* spp., *Nezara* spp., *Oestrus* spp., *Oscinella frit, Pegomyia* spp., *Phorbia* spp., *Prodiplosis* spp., *Psila rosae, Rhagoletis* spp., *Stomoxys* spp., *Tabanus* spp., *Tannia* spp., *Tetanops* spp., *Tipula* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Pomacea* spp., *Succinea* spp.

From the class of the helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti*.

It is furthermore possible to control protozoa, such as *Eimeria*.

From the order of the Heteroptera, for example, *Anasa tristis, Antestiopsis* spp., *Blissus* spp., *Calocoris* spp., *Campylomma livida, Cavelerius* spp., *Cimex* spp., *Collaria* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Monalonion atratum, Nezara* spp., *Oebalus* spp., *Pentomidae, Piesma quadrata, Piezodorus* spp., *Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.

From the order of the Homoptera, for example, *Acyrthosipon* spp., *Acrogonia* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Drosicha* spp., *Dysaphis* spp., *Dysmicoccus* spp., *Empoasca* spp., *Eriosoma* spp., *Erythroneura* spp., *Euscelis bilobatus, Ferrisia* spp., *Geococcus coffeae, Hieroglyphus* spp., *Homalodisca coagulata, Hyalopterus arnndinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva* spp., *Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp., *Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes* spp., *Trioza* spp., *Typhlocyba* spp., *Unaspis* spp., *Viteus vitifolii, Zygina* spp.

From the order of the Hymenoptera, for example, *Athalia* spp., *Diprion* spp., *Hoplocampa* spp., *Lasius* spp., *Monomorium pharaonis, Vespa* spp.

From the order of the Isopoda, for example, *Armadillidium vulgare, Oniscus asellus, Porcellio scaber*.

From the order of the Isoptera, for example, *Acromyrmex* spp., *Atta* spp., *Cornitermes cumulans, Microtermes obesi, Odontotermes* spp., *Reticulitermes* spp.

From the order of the Lepidoptera, for example, *Acronicta major, Adoxophyes* spp., *Aedia leucomelas, Agrotis* spp., *Alabama* spp., *Amyelois transitella, Anarsia* spp., *Anticarsia* spp., *Argyroploce* spp., *Barathra brassicae, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., *Choristoneura* spp., *Clysia ambiguella*,

*Cnaphalocerus* spp., *Cnephasia* spp., *Conopomorpha* spp., *Conotrachelus* spp., *Copitarsia* spp., *Cydia* spp., *Dalaca noctuides*, *Diaphania* spp., *Diatraea saccharalis*, *Earias* spp., *Ecdytolopha aurantium*, *Elasmopalpus lignosellus*, *Eldana saccharina*, *Ephestia kuehniella*, *Epinotia* spp., *Epiphyas postvittana*, *Etiella* spp., *Eulia* spp., *Eupoecilia ambiguella*, *Euproctis* spp., *Euxoa* spp., *Feltia* spp., *Galleria mellonella*, *Gracillaria* spp., *Grapholitha* spp., *Hedylepta* spp., *Helicoverpa* spp., *Heliothis* spp., *Hofmannophila pseudospretella*, *Homoeosoma* spp., *Homona* spp., *Hyponomeuta padella*, *Kakivoria flavofasciata*, *Laphygma* spp., *Laspeyresia molesta*, *Leucinodes orbonalis*, *Leucoptera* spp., *Lithocolletis* spp., *Lithophane antennata*, *Lobesia* spp., *Loxagrotis albicosta*, *Lymantria* spp., *Lyonetia* spp., *Malacosoma neustria*, *Maruca testulalis*, *Mamestra brassicae*, *Mocis* spp., *Mythimna separata*, *Nymphula* spp., *Oiketicus* spp., *Oria* spp., *Orthaga* spp., *Ostrinia* spp., *Oulema oryzae*, *Panolis flammea*, *Parnara* spp., *Pectinophora* spp., *Perileucoptera* spp., *Phthorimaea* spp., *Phyllocnistis citrella*, *Phyllonorycter* spp., *Pieris* spp., *Platynota stultana*, *Plusia* spp., *Plutella xylostella*, *Prays* spp., *Prodenia* spp., *Protoparce* spp., *Pseudaletia* spp., *Pseudoplusia includens*, *Pyrausta nubilalis*, *Rachiplusia nu*, *Schoenobius* spp., *Scirpophaga* spp., *Scotia segetum*, *Sesamia* spp., *Sparganothis* spp., *Spodoptera* spp., *Stathmopoda* spp., *Stomopteryx subsecivella*, *Synanthedon* spp., *Tecia solanivora*, *Thermesia gemmatalis*, *Tinea pellionella*, *Tineola bisselliella*, *Tortrix* spp., *Trichoplusia* spp., *Tuta absoluta*, *Virachola* spp.

From the order of the Orthoptera, for example, *Acheta domesticus*, *Blatta orientalis*, *Blattella germanica*, *Dichroplus* spp., *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp., *Xenopsylla cheopis*.

From the order of the Symphyla, for example, *Scutigerella* spp.

From the order of the Thysanoptera, for example, *Anaphothrips obscurus*, *Baliothrips biformis*, *Drepanothris reuteri*, *Enneothrips flavens*, *Frankliniella* spp., *Heliothrips* spp., *Hercinothrips femoralis*, *Rhipiphorothrips cruentatus*, *Scirtothrips* spp., *Taeniothrips cardamoni*, *Thrips* spp.

From the order of the Thysanura, for example, *Lepisma saccharina*.

The phytoparasitic nematodes include, for example, *Aphelenchoides* spp., *Bursaphelenchus* spp., *Ditylenchus* spp., *Globodera* spp., *Heterodera* spp., *Longidorus* spp., *Meloidogyne* spp., *Pratylenchus* spp., *Radopholus similis*, *Trichodorus* spp., *Tylenchulus semipenetrans*, *Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be employed as intermediates or precursors for the synthesis of other active compounds.

The active compounds can be converted to the customary formulations, such as solutions, emulsions, wettable powders, water- and oil-based suspensions, powders, dusts, pastes, soluble powders, soluble granules, granules for broadcasting, suspension-emulsion concentrates, natural materials impregnated with active compound, synthetic materials impregnated with active compound, fertilizers and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers. The formulations are prepared either in suitable plants or else before or during the application.

Suitable for use as auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and non-polar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethyl sulphoxide, and also water.

Suitable solid carriers are:
for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are nonionic and/or ionic substances, for example from the classes of the alcohol-POE- and/or -POP-ethers, acid and/or POP-POE esters, alkyl aryl and/or POP-POE ethers, fat- and/or POP-POE adducts, POE- and/or POP-polyol derivatives, POE- and/or POP-sorbitan- or -sugar adducts, alkyl or aryl sulphates, alkyl- or arylsulphonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulphonic acid derivatives, unmodified and modified celluloses, aromatic and/or aliphatic sulphonic acids and their adducts with formaldehyde.

Tackifiers such as carboxymethylcellulose, natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Other possible additives are perfumes, mineral or vegetable, optionally modified oils, waxes and nutrients (including trace nutrients), such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present.

The formulations generally comprise between 0.01 and 98% by weight of active compound, preferably between 0.5 and 90%.

The active compounds according to the invention may be used as they are or in their formulations, including a mixture with one or more suitable fungicides, bactericides, acaricides, nematicides, insecticides, microbiologicals, fertilizers, attractants, sterilants, synergists, safeners, semiochemicals and/or plant growth regulators, in order thereby, for example, to broaden the activity spectrum, to prolong the duration of action, to increase the rate of action, to prevent repulsion or to prevent development of resistance. Furthermore, combinations of this kind may improve plant growth, raise tolerance towards abiotic factors such as high or low temperatures, against drought or against increased levels of water and/or soil salt. It is also possible to improve the flowering and fruiting performance, to facilitate harvesting and increase yields, to influence ripening, to increase the quality and/or nutritional value of the harvested products, to prolong storage life and/or to improve the manageability of the harvested products. Generally speaking, combining the active compounds of the invention and co-components produces synergistic effects—that is, the activity of the mixture in question is greater than the activity of the individual components. In general it is possible to use the combinations not only in premixes, tankmixes or ready-made mixes but also in seed applications.

Particularly favourable co-components are, for example, those listed below.

Insecticides/Acaricides/Nematicides:

The active compounds identified here by their common name are known and are described, for example, in the pesticide handbook ("The Pesticide Manual" 14th Ed., British Crop Protection Council 2006) or can be found on the Internet (e.g. http://www.alanwood.net/pesticides).

(1) Acetylcholinesterase (AChE) inhibitors, for example
carbamates, for example alanycarb, aldicarb, bendiocarb, benfuracarb, butocarboxim, butoxy-carboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or
organophosphates, for example acephate, azamethiphos, azinphos (-methyl, -ethyl), cadusafos, chlorethoxyfos, chlorfenvinphos, chlormephos, chlorpyrifos (-methyl), coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion (-methyl), phenthoate, phorate, phosalone, phosmet, phosphamidon, phoxim, pirimiphos (-methyl), profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example
organochlorines, for example chlordane and endosulfan (alpha-); or
fiproles (phenylpyrazoles), for example ethiprole, fipronil, pyrafluprole and pyriprole.

(3) Sodium channel modulators/voltage-dependent sodium channel blockers, for example
pyrethroids, for example acrinathrin, allethrin (d-cis-trans, d-trans), bifenthrin, bioallethrin, bioallethrin-S-cyclopentenyl, bioresmethrin, cycloprothrin, cyfluthrin (beta-), cyhalothrin (gamma-, lambda-), cypermethrin (alpha-, beta-, theta-, zeta-), cyphenothrin [(1R)-trans-isomers], deltamethrin, dimefluthrin, empenthrin [(EZ)-(1R)-isomers], esfenvalerate, etofenprox, fenpropathrin, fenvalerate, flucythrinate, flumethrin, fluvalinate (tau-), halfenprox, imiprothrin, metofluthrin, permethrin, phenothrin [(1R)-trans-isomer], prallethrin, profluthrin, pyrethrins (pyrethrum), resmethrin, RU 15525, silafluofen, tefluthrin, tetramethrin [(1R)-isomers], tralomethrin, transfluthrin and ZXI 8901; DDT; or methoxychlor.

(4) Nicotinergic acetylcholine receptor agonists, for example neonicotinoids, for example acetamiprid, clothianidin, dinotefuran, imidacloprid, nitenpyram, thiacloprid, thiamethoxam; or nicotine.

(5) Allosteric acetylcholine receptor modulators (agonists), for example
spinosyns, for example spinetoram and spinosad.

(6) Chloride channel activators, for example
avermectins/milbemycins, for example abamectin, emamectin benzoate, lepimectin and milbemectin.

(7) Juvenile hormone analogues, for example hydroprene, kinoprene, methoprene; or fenoxycarb; pyriproxyfen.

(8) Active compounds with unknown or non-specific mechanisms of action, for example
fumigants, for example methyl bromide and other alkyl halides; or
chloropicrin; sulphuryl fluoride; borax; tartar emetic.

(9) Selective antifeedants, for example pymetrozine; or flonicamid.

(10) Mite growth inhibitors, for example clofentezine, diflovidazin, hexythiazox, etoxazole.

(11) Microbial disruptors of the insect gut membrane, for example Bacillus thuringiensis subspecies israelensis, Bacillus sphaericus, Bacillus thuringiensis subspecies aizawai, Bacillus thuringiensis subspecies kurstaki, Bacillus thuringiensis subspecies tenebrionis, and BT plant proteins, for example Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron; or
organotin compounds, for example azocyclotin, cyhexatin, fenbutatin oxide; or
propargite; tetradifon.

(13) Oxidative phoshorylation decouplers acting by interrupting the H proton gradient, for example chlorfenapyr and DNOC.

(14) Nicotinergic acetylcholine receptor antagonists, for example bensultap, cartap (hydrochloride), thiocylam, and thiosultap (sodium).

(15) Chitin biosynthesis inhibitors, type 0, for example benzoylureas, for example bistrifluron, chlorfluazuron, diflubenzuron, flucycloxuron, flufenoxuron, hexaflumuron, lufenuron, novaluron, noviflumuron, teflubenzuron and triflumuron.

(16) Chitin biosynthesis inhibitors, type 1, for example buprofezin.

(17) Moulting disruptors, for example cyromazine.

(18) Ecdysone agonists/disruptors, for example diacylhydrazines, for example chromafenozide, halofenozide, methoxyfenozide and tebufenozide.

(19) Octopaminergic agonists, for example amitraz.

(20) Complex-III electron transport inhibitors, for example hydramethylnone; acequinocyl; fluacrypyrim.

(21) Complex-I electron transport inhibitors, for example from the group of the METI acaricides, for example fenazaquin, fenpyroximate, pyrimidifen, pyridaben, tebufenpyrad, tolfenpyrad; or
rotenone (Derris).

(22) Voltage-dependent sodium channel blockers, for example indoxacarb; metaflumizone.

(23) Inhibitors of acetyl-CoA carboxylase, for example tetronic acid derivatives, for example spirodiclofen and spiromesifen; or tetramic acid derivatives, for example spirotetramat.

(24) Complex-IV electron transport inhibitors, for example phosphines, for example aluminium phosphide, calcium phosphide, phosphine, zinc phosphide; or cyanide.

(25) Complex-II electron transport inhibitors, for example cyenopyrafen.

(28) Ryanodine receptor effectors, for example diamides, for example chlorantraniliprole (Rynaxypyr), cyantraniliprole (Cyazypyr) and flubendiamide.

Further active compounds with unknown mechanism of action, for example azadirachtin, amidoflumet, benzoximate, bifenazate, chinomethionat, cryolite, cyflumetofen, dicofol, fluensulfone (5-chloro-2-[(3,4,4-trifluorobut-3-en-1-yl)sulphonyl]-1,3-thiazole), flufenerim, pyridalyl and pyrifluquinazon; and also products based on *Bacillus firmus* (I-1582, BioNeem, Votivo) and also the known active compounds below 4-{[(6-bromopyrid-3-yl)methyl](2-fluoroethyl) amino}furan-2(5H)-one (known from WO 2007/115644), 4-{[(6-fluoropyrid-3-yl)methyl](2,2-difluoroethyl) amino}furan-2(5H)-one (known from WO 2007/115644), 4-{[(2-chloro-1,3-thiazol-5-yl)methyl](2-fluoroethyl) amino}furan-2(5H)-one (known from WO 2007/115644), 4-{[(6-chloropyrid-3-yl)methyl](2-fluoroethyl) amino}furan-2(5H)-one (known from WO 2007/115644), 4-{[(6-chloropyrid-3-yl)methyl](2,2-difluoroethyl) amino}furan-2(5H)-one (known from WO 2007/115644), 4-{[(6-chloro-5-fluoropyrid-3-yl)methyl](methyl) amino}furan-2(5H)-one (known from WO 2007/115643), 4-({[(5,6-dichloropyrid-3-yl)methyl](2-fluoroethyl) amino}furan-2(5H)-one (known from WO 2007/115646), 4-{[(6-chloro-5-fluoropyrid-3-yl)methyl](cyclopropyl) amino}furan-2(5H)-one (known from WO 2007/115643), 4-{[(6-chloropyrid-3-yl)methyl](cyclopropyl)amino}furan-2(5H)-one (known from EP-A-0 539 588), 4-{[(6-chloropyrid-3-yl)methyl](methyl)amino}furan-2(5H)-one (known from EP-A-0 539 588), [(6-chloropyridin-3-yl)methyl](methyl)oxido-λ⁴-sulphanylidenecyanamide (known from WO 2007/149134), [1-(6-chloropyridin-3-yl)ethyl](methyl)oxido-λ⁴-sulphanylidenecyanamide (known from WO 2007/149134) and its diastereomers (A) and (B)

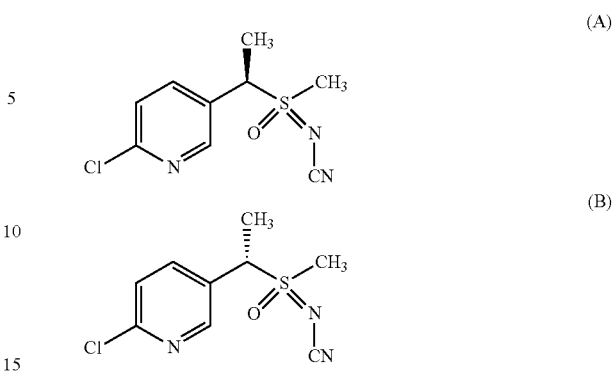

(also known from WO 2007/149134), [(6-trifluoromethylpyridin-3-yl)methyl](methyl)oxido-λ⁴-sulphanylidenecyanamide (known from WO 2007/095229), sulfoxaflor (also known from WO 2007/149134), 11-(4-chloro-2,6-dimethylphenyl)-12-hydroxy-1,4-dioxa-9-azadispiro[4.2.4.2]tetradec-11-en-10-one (known from WO 2006/089633), 3-(4'-fluoro-2,4-dimethylbiphenyl-3-yl)-4-hydroxy-8-oxa-1-azaspiro[4.5]dec-3-en-2-one (known from WO 2008/067911) and 1-[2-fluoro-4-methyl-5-[(2,2,2-trifluoroethyl)sulphinyl]phenyl]-3-(trifluoromethyl)-1H-1,2,4-triazole-5-amine (known from WO 2006/043635).

Fungicides (1) Ergosterol biosynthesis inhibitors, such as, for example, aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulphate, imibenconazole, ipconazole, metconazole, myclobutanil, naftifine, nuarimol, oxpoconazole, paclobutrazol, pefurazoate, penconazole, piperalin, prochloraz, propiconazole, prothioconazole, pyributicarb, pyrifenox, quinconazole, simeconazole, spiroxamine, tebuconazole, terbinafine, tetraconazole, triadimefon, triadimenol, tridemorph, triflumizole, triforine, triticonazole, uniconazole, uniconazole-p, viniconazole, voriconazole, 1-(4-chlorophenyl)-2-(1H-1,2,4-triazol-1-yl)cycloheptanol, methyl 1-(2,2-dimethyl-2,3-dihydro-1H-inden-1-yl)-1H-imidazole-5-carboxylate, N'-{5-(difluoromethyl)-2-methyl-4-[3-(trimethylsilyl)propox]phenyl}-N-ethyl-N-methylimidoformamide, N-ethyl-N-methyl-N'-{2-methyl-5-(trifluoromethyl)-4-[3-(trimethylsilyl)propoxy]phenyl}imidoformamide and O-[1-(4-methoxyphenoxy)-3,3-dimethylbutan-2-yl]-1H-imidazole-1-carbothioate.

(2) Respiration inhibitors (respiratory-chain inhibitors), such as, for example, bixafen, boscalid, carboxin, diflumetorim, fenfuram, fluopyram, flutolanil, fluxapyroxad, furametpyr, furmecyclox, isopyrazam mixture of the syn-epimeric racemate 1RS,4SR,9RS and of the anti-epimeric racemate 1RS,4SR,9SR, isopyrazam (anti-epimeric racemate), isopyrazam (anti-epimeric enantiomer 1R,4S,9S), isopyrazam (anti-epimeric enantiomer 1S,4R,9R), isopyrazam (syn-epimeric racemate 1RS,4SR,9RS), isopyrazam (syn-epimeric enantiomer 1R,4S,9R), isopyrazam (syn-epimeric enantiomer 1S,4R,9S), mepronil, oxycarboxin, penflufen, penthiopyrad, sedaxane, thifluzamid, 1-methyl-N-[2-(1,1,2,2-tetrafluoroethoxy)phenyl]-3-(trifluoromethyl)-1H-pyrazole-4-carboxamide, 3-(difluoromethyl)-1-methyl-N-[2-(1,1,2,2-tetrafluoroethoxy)phenyl]-1H-pyrazole-4- carboxamide, 3-(difluoromethyl)-N-[4-fluoro-2-(1,1,2,3,3,3-hexafluoropropoxy)phenyl]-1-methyl-1H-pyrazole-4-carboxamide and N-[1-(2,4-dichlorophenyl)-1-methoxypropan-2-yl]-3-(difluoromethyl)-1-methyl-1H-pyrazole-4-carboxamide.

(3) Respiration inhibitors (respiratory-chain inhibitors) on the complex MI of the respiratory chain, such as, for example, ametoctradin, amisulbrom, azoxystrobin, cyazofamid, dimoxystrobin, enestroburin, famoxadon, fenamidon, fluoxastrobin, kresoxim-methyl, metominostrobin, orysastrobin, picoxystrobin, pyraclostrobin, pyrametostrobin, pyraoxystrobin, pyribencarb, trifloxystrobin, (2E)-2-(2-{[6-(3-chloro-2-methylphenoxy)-5-fluoropyrimidin-4-yl]oxy}phenyl)-2-(methoxyimino)-N-methylethanamide, (2E)-2-(methoxyimino)-N-methyl-2-(2-{[({(1E)-1-[3-(trifluoromethyl)phenyl]ethylidene}amino)oxy]methyl}phenyl)ethanamide, (2E)-2-(methoxyimino)-N-methyl-2-{2-[(E)-({1-[3-(trifluoromethyl)phenyl]ethoxy}imino)methyl]phenyl}ethanamide, (2E)-2-{2-[({[(1E)-1-(3-{[(E)-1-fluoro-2-phenylethenyl]oxy}phenyl)ethylidene]amino}oxy)methyl]phenyl}-2-(methoxyimino)-N-methylethanamide, (2E)-2-{2-[({[(2E,3E)-4-(2,6-dichlorophenyl)but-3-en-2-ylidene]amino}-oxy)methyl]phenyl}-2-(methoxyimino)-N-methylethanamide, 2-chloro-N-(1,1,3-trimethyl-2,3-dihydro-1H-inden-4-yl)pyridine-3-carboxamide, 5-methoxy-2-methyl-4-(2-{[({(1E)-1-[3-(trifluoro-methyl)phenyl]ethylidene}amino)oxy]methyl}phenyl)-2,4-dihydro-3H-1,2,4-triazol-3-one, methyl (2E)-2-{2-[(({cyclopropyl[(4-methoxyphenyl)imino]methyl}sulphanyl)methyl]phenyl}-3-methoxy-prop-2-enoate, N-(3-ethyl-3,5,5-trimethylcyclohexyl)-3-(formylamino)-2-hydroxybenzamide, 2-{2-[(2,5-dimethylphenoxy)methyl]phenyl}-2-methoxy-N-methylacetamide and (2R)-2-{2-[(2,5-dimethylphenoxy)methyl]phenyl}-2-methoxy-N-methylacetamide.

(4) Mitosis and cell division inhibitors, such as, for example, benomyl, carbendazim, chlorfenazole, diethofencarb, ethaboxam, fluopicolid, fuberidazole, pencycuron, thiabendazole, thiophanate-methyl, thiophanate, zoxamide, 5-chloro-7-(4-methylpiperidin-1-yl)-6-(2,4,6-trifluorophenyl)[1,2,4]triazolo[1,5-a]pyrimidine and 3-chloro-5-(6-chloropyridin-3-yl)-6-methyl-4-(2,4,6-trifluorophenyl)pyridazine.

(5) Compounds with multi-site activity, such as, for example, Bordeaux mixture, captafol, captan, chlorothalonil, copper preparations such as copper hydroxide, copper naphthenate, copper oxide, copper oxychloride, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, man copper, mancozeb, maneb, metiram, metiram-zinc, oxinecopper, propamidine, propineb, sulphur and sulphur preparations such as, for example, calcium polysulphide, thiram, tolylfluanid, zineb and ziram.

(6) Resistance inductors, such as, for example, acibenzolar-S-methyl, isotianil, probenazole and tiadinil.

(7) Amino acid and protein biosynthesis inhibitors, such as, for example, andoprim, blasticidin-S, cyprodinil, kasugamycin, kasugamycin hydrochloride hydrate, mepanipyrim and pyrimethanil.

(8) ATP production inhibitors, such as, for example, fentin acetate, fentin chloride, fentin hydroxide and silthiofan.

(9) Cell wall synthesis inhibitors, such as, for example, benthiavalicarb, dimethomorph, flumorph, iprovalicarb, mandipropamid, polyoxins, polyoxorim, validamycin A and valifenalate.

(10) Lipid and membrane synthesis inhibitors, such as, for example, biphenyl, chloroneb, dicloran, edifenphos, etridiazole, iodocarb, iprobenfos, isoprothiolane, propamocarb, propamocarb hydrochloride, prothiocarb, pyrazophos, quintozene, tecnazene and tolclofos-methyl.

(11) Melanin biosynthesis inhibitors, such as, for example, carpropamid, diclocymet, fenoxanil, fthalide, pyroquilon and tricyclazole.

(12) Nucleic acid synthesis inhibitors, such as, for example, benalaxyl, benalaxyl M (kiralaxyl), bupirimate, clozylacon, dimethirimol, ethirimol, furalaxyl, hymexazol, metalaxyl, metalaxyl-M (mefenoxam), ofurace, oxadixyl and oxolinic acid.

(13) Signal transduction inhibitors, such as, for example, chlozolinate, fenpiclonil, fludioxonil, iprodione, procymidon, quinoxyfen and vinclozoline.

(14) Decouplers, such as, for example, binapacryl, dinocap, ferimzone, fluazinam and meptyldinocap.

(15) Further compounds, such as, for example, benthiazole, bethoxazin, capsimycin, carvone, chinomethionat, chlazafenon, cufraneb, cyflufenamid, cymoxanil, cyprosulfamide, dazomet, debacarb, dichlorophen, diclomezine, difenzoquat, difenzoquat methylsulphate, diphenylamine, ecomat, fenpyrazamine, flumetover, fluoromid, flusulfamide, flutianil, fosetyl-aluminium, fosetyl-calcium, fosetyl-sodium, hexachlorobenzene, irumamycin, methasulphocarb, methyl isothiocyanate, metrafenone, mildiomycin, natamycin, nickel dimethyldithiocarbamate, nitrothal-isopropyl, octhilinone, oxamocarb, oxyfenthiin, pentachlorophenol and its salts, phenothrin, phosphoric acid and its salts, propamocarb-fosetylate, propanosine-sodium, proquinazid, pyrrolnitrin, tebufloquin, tecloftalam, tolnifanid, triazoxide, trichlamide, zarilamide, 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, 1-(4-methoxyphenoxy)-3,3-dimethylbutan-2-yl 1H-imidazole-1-carboxylate, 2,3,5,6-tetrachloro-4-(methylsulphonyl)pyridine, 2,3-dibutyl-6-chlorothieno[2,3-d]pyrimidin-4(3H)-one, 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, 2-butoxy-6-iodo-3-propyl-4H-chromen-4-one, 2-chloro-5-[2-chloro-1-(2,6-difluoro-4-methoxyphenyl)-4-methyl-1H-imidazol-5-yl]pyridine, 2-phenylphenol and its salts, 3,4,5-trichloropyridine-2,6-dicarbonitrile, 3-[5-(4-chlorophenyl)-2,3-dimethyl-1,2-oxazolidin-3-yl]pyridine, 3-chloro-5(4-chlorophenyl)-4-(2,6-difluorophenyl)-6-methylpyridazine, 4-(4-chlorophenyl)-5-(2,6-difluorophenyl)-3,6-dimethylpyridazine, 5-amino-1,3,4-thiadiazole-2-thiol, 5-chlor-N'-phenyl-N'-(prop-2-yn-1-yl)thiophene-2-sulphonohydrazide, 5-methyl-6-octyl[1,2,4]triazolo[1,5-a]pyrimidin-7-amine, ethyl(2Z)-3-amino-2-cyano-3-phenylprop-2-enoate, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, N-[(5-brom-3-chloropyridin-2-yl)methyl]-2,-dichloropyridine-3-carboxamide, N-[1-(5-bromo-3- chloropyridin-2-yl)ethyl]-2,4-dichloropyridine-3-carboxamide, N-[1-(5-bromo-3-chloropyridin-2-yl)ethyl]-2-fluoro-4-iodopyridine-3-carboxamide, N-{(E)-[(cyclopropylmethoxy)imino][6-(difluoromethoxy)-2,3-difluorophenyl]methyl}-2-phenylacetamide, N-{(Z)-[(cyclopropylmethoxy)imino][6-(difuoromethoxy)-2,3-difuorophenyl]methyl}-2-phenylacetamide, N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, N-methyl-2-(1-{[5-methyl-3-(trifluoromethyl)-1H-pyrazol-1-yl]acetyl}piperidin-4-yl)-N-[(1S)-1,2,3,4-tetrahydronaphthalen-1-yl]-1,3-thiazole-4-carboxamide, pentyl {6-[({[(1-methyl-1H-tetrazol-5-yl)(phenyl)methylidene]amino}oxy)methyl]pyridin-2-yl}carbamate, phenazine-1-carboxylic acid, quinolin-8-ol and quinolin-8-ol sulphate (2:1).

(16) Further compounds, such as, for example, 1-methyl-3-(trifluoromethyl)-N-[2'-(trifluoromethyl)biphenyl-2-yl]-1H-pyrazole-4-carboxamide, N-(4'-chlorobiphenyl-2-yl)-3-(difluoromethyl)-1-methyl-1H-pyrazole-4-carboxamide, N-(2',4'-dichlorobiphenyl-2-yl)-3-(difluoromethyl)-1-methyl-1H-pyrazole-4-carboxamide, 3-(difluoromethyl)-1-methyl-N-[4'-(trifluoromethyl)biphenyl-2-yl]-1H-pyrazole-4-carboxamide, N-(2',5'-difluorobiphenyl-2-yl)-1-methyl-3-(trifluoromethyl)-1H-pyrazole-4-carboxamide, 3-(difluoromethyl)-1-methyl-N-[4'-(prop-1-yn-1-yl)biphenyl-2-yl]-1H-pyrazole-4-carboxamide, 5-fluoro-1,3-dimethyl-N-[4'-(prop-1-yn-1-yl)biphenyl-2-yl]-1H-pyrazole-4-carboxamide, 2-chloro-N-[4'-(prop-1-yn-1-yl)biphenyl-2-yl]pyridine-3-carboxamide, 3-(difluoromethyl)-N-[4'-(3,3-dimethylbut-1-yn-1-yl)biphenyl-2-yl]-1-methyl-1H-pyrazole-4-carboxamide, N-[4'-(3,3-dimethylbut-1-yn-1-yl)biphenyl-2-yl]-5-fluoro-1,3-dimethyl-1H-pyrazole-4-carboxamide, 3-(difluoromethyl)-N-(4'-ethynylbiphenyl-2-yl)-1-methyl-1H-pyrazole-4-carboxamide, N-(4'-ethynylbiphenyl-2-yl)-5-fluoro-1,3-dimethyl-1H-pyrazole-4-carboxamide, 2-chloro-N-(4'-ethynylbiphenyl-2-yl)pyridine-3-carboxamide, 2-chloro-N-[4'-(3,3-dimethylbut-1-yn-1-yl)biphenyl-2-yl]pyridine-3-carboxamide, 4-(difluoromethyl)-2-methyl-N-[4'-(trifluoromethyl)biphenyl-2-yl]-1,3-thiazole-5-carboxamide, 5-fluoro-N-[4'-(3-hydroxy-3-methylbut-1-yn-1-yl)biphenyl-2-yl]-1,3-dimethyl-1H-pyrazole-4-carboxamide, 2-chloro-N-[4'-(3-hydroxy-3-methylbut-1-yn-1-yl)biphenyl-2-yl]pyridine-3-carboxamide, 3-(difluoromethyl)-N-[4'-(3-methoxy-3-methylbut-1-yn-1-yl)biphenyl-2-yl]-1-methyl-1H-pyrazole-4-carboxamide, 5-fluoro-N-[4'-(3-methoxy-3-methylbut-1-yn-1-yl)biphenyl-2-yl]-1,3-dimethyl-1H-pyrazole-4-carboxamide, 2-chloro-N-[4'-(3-methoxy-3-methylbut-1-yn-1-yl)biphenyl-2-yl]pyridine-3-carboxamide, (5-bromo-2-methoxy-4-methylpyridin-3-yl)(2,3,4-trimethoxy-6-methylphenyl)methanone and N-[2-(4-{[3-(4-chlorophenyl)prop-2-yn-1-yl]oxy}-3-methoxyphenyl)ethyl]-N2-(methylsulphonyl)valinamide.

All of the stated co-components of classes (1) to (16) can form salts, where appropriate with suitable bases or acids, provided they are capable of so doing on the basis of their functional groups.

Each additional active compound may be mixed in a wide range, preferably in a weight ratio of from 100:1 to 1:100, particularly preferably from 5:1 to 1:5, with the active compounds according to the invention.

A mixture with other known active compounds, such as herbicides, fertilizers, growth regulators, safeners, semiochemicals, or else with agents for improving plant properties, is also possible.

In a preferred embodiment of the invention, a penetrant is additionally added to the crop protection compositions for enhancing the activity. Suitable penetrants also include, for example, substances which promote the availability of the compounds of the formula (I) in the spray coating. These include, for example, mineral or vegetable oils. Suitable oils are all mineral or vegetable oils—modified or otherwise—which can typically be used in agrochemical compositions. Mention may be made by way of example of sunflower oil, rapeseed oil, olive oil, castor oil, colza oil, maize seed oil, cotton seed oil and soybean oil, or the esters of said oils. Preference is given to rapeseed oil, sunflower oil and their methyl or ethyl esters, in particular to rapeseed oil methyl ester.

The concentration of penetrant in the compositions of the invention can be varied within a wide range. In the case of a formulated crop protection composition it is in general 1% to 95%, preferably 1% to 55%, more preferably 15%-40% by weight. In the ready-to-use compositions (spray liquors) the concentrations are generally between 0.1 and 10 g/l, preferably between 0.5 and 5 g/l.

When used as insecticides, the active compounds according to the invention can furthermore be present in their commercially available formulations and in the use forms, prepared from these formulations, as a mixture with synergists. Synergists are compounds which increase the action of the active compounds, without it being necessary for the synergistic agent added to be active itself.

When used as insecticides, the active compounds according to the invention can furthermore be present in their commercially available formulations and in the use forms, prepared from these formulations, as mixtures with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

All plants (mention may be made of turf, vines, cereals, for example wheat, barley, rye, oats, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cacao beans and peanuts; cucurbits, for example pumpkin/squash, cucumbers and melons; fibre plants, for example cotton, flax, hemp and jute; citrus fruit, for example oranges, lemons, grapefruit and tangerines; vegetables, for example spinach, lettuce, asparagus, cabbage species, carrots, onions, tomatoes, potatoes and bell peppers; Lauraceae, for example avocado, *Cinnamomum*, camphor, or also plants such as tobacco, nuts, coffee, aubergine, sugarcane, tea, pepper, grapevines, hops, bananas, latex plants and ornamentals, for example flowers, shrubs, deciduous trees and coniferous trees, this enumeration does not represent any limitation) and plant parts may be treated in accordance with the invention. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. Parts of plants also include harvested plants and vegetative and generative propagation material, for example seedlings, tubers, rhizomes, cuttings and seeds.

Treatment according to the invention of the plants and plant parts with the active compounds is carried out directly or by allowing the compounds to act on their surroundings, habitat or storage space by the customary treatment methods, for example by immersion, spraying, evaporation, fogging, scattering, painting on, injecting and, in the case of propagation material, in particular in the case of seeds, also by applying one or more coats.

As already mentioned above, it is possible to treat all plants and their parts according to the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (Genetically Modified Organisms), and parts thereof are treated. The terms "parts", "parts of plants" and "plant parts" have been explained above.

Particularly preferably, plants of the plant cultivars which are in each case commercially available or in use are treated according to the invention. Plant cultivars are to be understood as meaning plants having novel properties ("traits") which have been obtained by conventional breeding, by mutagenesis or by recombinant DNA techniques. These can be cultivars, bio- or genotypes.

Depending on the plant species or plant cultivars, their location and growth conditions (soils, climate, vegetation period, diet), the treatment according to the invention may also result in superadditive ("synergistic") effects. Thus, for example, reduced application rates and/or a widening of the activity spectrum and/or an increase in the activity of the substances and compositions which can be used according to the invention, better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products are possible, which exceed the effects which were actually to be expected.

The transgenic plants or plant cultivars (obtained by genetic engineering) which are preferably to be treated according to the invention include all plants which, by virtue of the genetic modification, received genetic material which imparts particularly advantageous, useful traits to these plants. Examples of such traits are better plant growth, increased tolerance to high or low temperatures, increased tolerance to drought or to water or soil salt content, increased flowering performance, easier harvesting, accelerated maturation, higher harvest yields, higher quality and/or a higher nutritional value of the harvested products, better storage stability and/or processability of the harvested products. Further and particularly emphasized examples of such traits are a better defence of the plants against animal and microbial pests, such as against insects, mites, phytopathogenic fungi, bacteria and/or viruses, and also increased tolerance of the plants to certain herbicidally active compounds. Examples of transgenic plants which may be mentioned are the important crop plants, such as cereals (wheat, rice), maize, soya beans, potatoes, sugar beet, tomatoes, peas and other vegetable varieties, cotton, tobacco, oilseed rape and also fruit plants (with the fruits apples, pears, citrus fruits and grapes), and particular emphasis is given to maize, soya beans, potatoes, cotton, tobacco and oilseed rape. Traits that are emphasized in particular are increased defence of the plants against insects, arachnids, nematodes and slugs and snails by virtue of toxins formed in the plants, in particular those formed in the plants by the genetic material from *Bacillus thuringiensis* (for example by the genes CryIA(a), CryIA(b), CryIA(c), CryIA, CryIIIA, CryIIIB2, Cry9c, Cry2Ab, Cry3Bb and CryIF and also combinations thereof) (referred to hereinbelow as "Bt plants"). Traits that are also particularly emphasized are the increased defence of the plants against fungi, bacteria and viruses by systemic acquired resistance (SAR), systemin, phytoalexins, elicitors and resistance genes and correspondingly expressed proteins and toxins. Traits that are furthermore particularly emphasized are the increased tolerance of the plants to certain herbicidally active compounds, for example imidazolinones, sulphonylureas, glyphosate or phosphinotricin (for example the "PAT" gene). The genes which impart the desired traits in question can also be present in combination with one another in the transgenic plants. Examples of "Bt plants" which may be mentioned are maize varieties, cotton varieties, soya bean varieties and potato varieties which are sold under the trade names YIELD GARD® (for example maize, cotton, soya beans), KnockOut® (for example maize), StarLink® (for example maize), Bollgard® (cotton), Nucotn® (cotton) and NewLeaf® (potato). Examples of herbicide-tolerant plants which may be mentioned are maize varieties, cotton varieties and soya bean varieties which are sold under the trade names Roundup Ready® (tolerance to glyphosate, for example maize, cotton, soya beans), Liberty Link® (tolerance to phosphinotricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars having these genetic traits or genetic traits still to be developed, which plant cultivars will be developed and/or marketed in the future.

The plants listed can be treated according to the invention in a particularly advantageous manner with the compounds of the general formula (I) and/or the active compound mixtures according to the invention. The preferred ranges stated above for the active compounds or mixtures also apply to the treatment of these plants. Particular emphasis is given to the treatment of plants with the compounds or mixtures specifically mentioned in the present text.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp., *Solenopotes* spp.

From the order of the Mallophagida and the suborders Amblycerina and Ischnocerina, for example, *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp.

From the order of the Siphonapterida, for example, *Pulex* spp., *Ctenocephalides* spp. (*Ctenocephalides canis*, *Ctenocephalides felis*), *Xenopsylla* spp., *Ceratophyllus* spp.

From the order of the Heteropterida, for example, *Cimex* spp., *Triatoma* spp., *Rhodnius* spp., *Panstrongylus* spp.

From the order of the Blattarida, for example, *Blatta orientalis*, *Periplaneta americana*, *Blattela germanica*, *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injections (intramuscular, subcutaneous, intravenous, intraperitoneal and the like), implants, by nasal application, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds of the formula (I) can be used as formulations (for example powders, emulsions, free-flowing compositions), which comprise the active compounds in an amount of from 1 to 80% by weight, directly or after 100 to 10 000-fold dilution, or they can be used as a chemical bath.

It has furthermore been found that the compounds according to the invention also have a strong insecticidal action against insects which destroy industrial materials.

The following insects may be mentioned as examples and as preferred—but without any limitation:

Beetles, such as *Hylotrupes bajulus*, *Chlorophorus pilosis*, *Anobium punctatum*, *Xestobium rufovillosum*, *Ptilinus pecticornis*, *Dendrobium pertinex*, *Ernobius mollis*, *Priobium carpini*, *Lyctus brunneus*, *Lyctus africanus*. *Lyctus planicollis*, *Lyctus linearis*, *Lyctus pubescens*, *Trogoxylon aequale*, *Minthes rugicollis*, *Xyleborus* spec. *Tryptodendron* spec. *Apate monachus*, *Bostrychus capucins*, *Heterobostrychus brunneus*, *Sinoxylon* spec. *Dinoderus minutus*;

Hymenopterons, such as *Sirex juvencus*, *Urocerus gigas*, *Urocerus gigas taignus*, *Urocerus augur*;

Termites, such as *Kalotermes flavicollis*, *Cryptotermes brevis*, *Heterotermes indicola*, *Reticulitermes flavipes*, *Reticulitermes santonensis*, *Reticulitermes lucifugus*, *Mastotermes darwiniensis*, *Zootermopsis nevadensis*, *Coptotermes formosanus*;

Bristletails, such as *Lepisma saccharina*.

Industrial materials in the present connection are to be understood as meaning non-living materials, such as, preferably, plastics, adhesives, sizes, papers and cardboards, leather, wood and processed wood products and coating compositions.

The ready-to-use compositions may, if appropriate, comprise further insecticides and, if appropriate, one or more fungicides.

With respect to possible additional additives, reference may be made to the insecticides and fungicides mentioned above.

The compounds according to the invention can likewise be employed for protecting objects which come into contact with saltwater or brackish water, in particular hulls, screens, nets, buildings, moorings and signalling systems, against fouling.

Furthermore, the compounds according to the invention, alone or in combinations with other active compounds, may be employed as antifouling agents.

In domestic, hygiene and stored-product protection, the active compounds are also suitable for controlling animal pests, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus*, *Argas reflexus*, *Bryobia* ssp., *Dermanyssus gallinae*, *Glyciphagus domesticus*, *Ornithodorus moubat*, *Rhipicephalus sanguineus*, *Trombicula alfreddugesi*, *Neutrombicula autumnalis*, *Dermatophagoides pteronissimus*, *Dermatophagoides forinae*.

From the order of the Araneae, for example, *Avicularidae, Araneidae.*

From the order of the *Opiliones,* for example, *Pseudoscorpiones chelifer, Pseudoscorpiones cheiridium, Opiliones phalangium.*

From the order of the Isopoda, for example, *Oniscus asellus, Porcellio scaber.*

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus.*

From the order of the Blattaria, for example, *Blatta orientalis, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

From the order of the Saltatoria, for example, *Acheta domesticus.*

From the order of the Dermaptera, for example, *Forficula auricularia.*

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

From the order of the Lepidoptera, for example, *Achroia grisella, Galleria mellonella, Plodia interpunctella, Tinea cloacella, Tinea pellionella, Tineola bisselliella.*

From the order of the Siphonaptera, for example, *Ctenocephalides canis, Ctenocephalides felis, Pulex irritans, Tunga penetrans, Xenopsylla cheopis.*

From the order of the Hymenoptera, for example, *Camponotus herculeanus, Lasius fuliginosus, Lasius niger, Lasius umbratus, Monomorium pharaonis, Paravespula* spp., *Tetramorium caespitum.*

From the order of the Anoplura, for example, *Pediculus humanus capitis, Pediculus humanus corporis, Pemphigus* spp., *Phylloera vastatrix, Phthirus pubis.*

From the order of the Heteroptera, for example, *Cimex hemipterus, Cimex lectularius, Rhodinus prolixus, Triatoma infestans.*

In the field of domestic insecticides, they are used alone or in combination with other suitable active compounds, such as phosphoric esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or polymer, liquid evaporators, gel and membrane evaporators, propeller-driven evaporators, energy-free, or passive, evaporation systems, moth papers, moth bags and moth gels, as granules or dusts, in baits for scattering or in bait stations.

PREPARATION EXAMPLES

Example 1

Step 1: 3-(4-Bromopyrazol-1-yl)pyridine

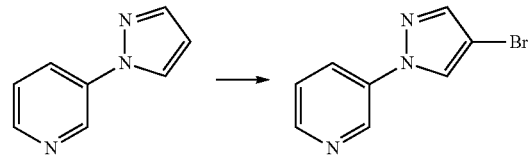 [SMILES: c1cncc(-n2cccn2)c1 ; Brc1cnn(-c2cccnc2)c1]

3-Pyrazol-1-ylpyridine (500 mg, 3.44 mmol) was dissolved in acetonitrile (15 ml), and ammonium cerium(IV) nitrate (944 mg, 1.72 mmol) was added (slightly exothermic). N-Bromosuccinimide (736 mg, 4.13 mmol) was added a little at a time (slightly exothermic) and the mixture was stirred at room temperature for 30 min and then heated under reflux for 3 hours (h). After the mixture had cooled, ethyl acetate was added. The organic phase was washed with water, washed with a sodium sulphate solution and then dried with magnesium sulphate. The solvent was removed under reduced pressure using a rotary evaporator.

Yield: 750 mg (93% of theory), log P (HCOOH) 1.56, [M$^+$+1] 224.0

$^1$H-NMR (d$_6$-DMSO): 7.54 (m, 1H), 7.90 (s, 1H), 8.20 (m, 1H), 8.55 (m, 1H), 8.79 (s, 1H), 9.06 (m, 1H).

Step 2: 3-[4-(4,4,5,5-Tetramethyl-[1,3,2]dioxaborolan-2-yl)pyrazol-1-yl]pyridine

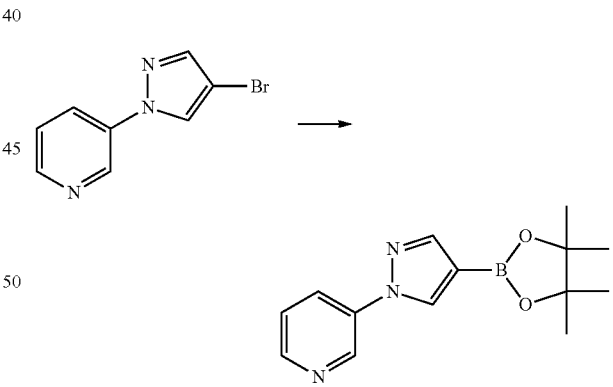

Under argon, dioxane (11 ml) was added to 3-(4-bromopyrazol-1-yl)pyridine (1.00 g, 4.46 mmol), 1,1'-bis(diphenylphosphino)ferrocene (dppf) (74 mg, 0.13 mmol), palladium dichloride-dppf (109 mg, 0.13 mmol), potassium acetate (1.31 g, 13.3 mmol) and pinacolatodiborane (1.19 g, 4.68 mmol). The mixture was heated under reflux for 24 h and then cooled. The solvent was removed under reduced pressure using a rotary evaporator and dichloromethane (100 ml) and water (100 ml) were added to the residue; the resulting solid was filtered off with suction and discarded. The filtrate was extracted with dichloromethane and the organic phase was dried with magnesium sulphate. The solvent was removed under reduced pressure using a rotary evaporator and the residue was chromatographed (ethyl acetate, cyclohexane).

Yield: 680 mg (55% of theory), log P (HCOOH) 2.19, [M++1] 272.2

$^1$H-NMR (d$_6$-DMSO): 1.30 (s, 12H), 7.51 (m, 1H), 7.90 (s, 1H), 8.25 (m, 1H), 8.51 (m, 1H), 8.73 (s, 1H), 9.12 (m, 1H).

Step 3: 2-(6-Bromopyridin-2-yl)pyrimidine

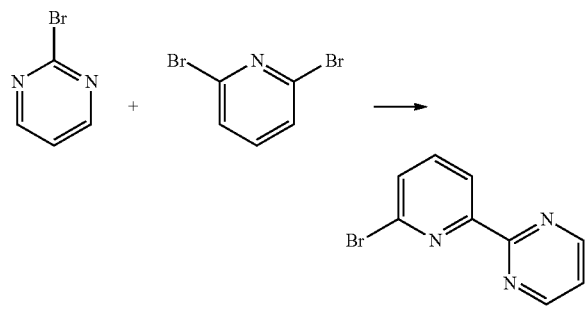

Under argon, 54.5 ml (137.1 mmol) of a 2.5-molar solution of n-butyllithium (n-Buli) were diluted with 70 ml of THF. At a temperature of less than −70° C., 32.5 g (137.1 mmol) of 2,6-dibromopyridine, dissolved in 150 ml of THF, were added dropwise. The mixture was stirred for 15 min and, still at a temperature of less than −70° C., 9.2 ml (107 mmol) of a 5.6-molar solution of zinc chloride in diethyl ether were then added. The mixture was allowed to thaw, and a solution of 17.4 g (109 mmol) of bromopyrimidine in 50 ml of THF and a suspension of 3.9 g (3.4 mmol) of tetrakis(triphenylphosphine)palladium in 50 ml of THF were added. The mixture was boiled under reflux for 4 h, and after cooling Na-EDTA in water and dilute aqueous sodium hydroxide solution to pH=10 were added. The mixture was filtered off with suction to remove undissolved particles, the aqueous phase was extracted three times with ethyl acetate, the combined organic phases were dried with MgSO$_4$ and the mixture was concentrated by evaporation. The residue was crystallized from 60 ml of benzotrifluoride, during this operation, the mixture was briefly boiled with activated carbon and filtered whilst still hot.

Yield: 14.82 g (52% of theory), log P (HCOOH) 1.3 [M+1] 236.0

$^1$H-NMR (CD$_3$CN): 7.4 (t, 1H), 7.65 (d, 1H), 7.8 (dd, 1H), 8.4 (d, 1H), 8.9 (m, 2H)

Step 4: 2-[6-(1-Pyridin-3-yl-1H-pyrazol-4-yl)pyridin-2-yl]pyrimidine

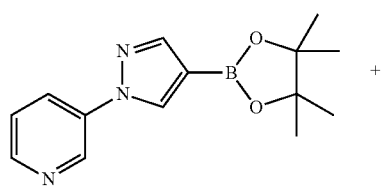

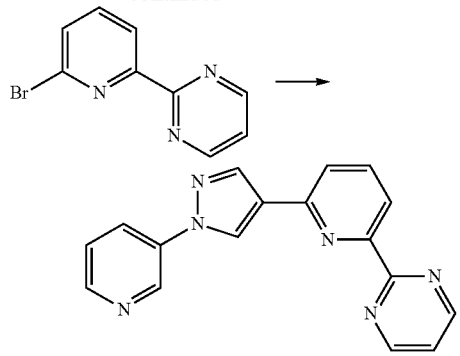

A mixture of acetonitrile (50 ml) and sodium carbonate (1N in water, 30 ml) (Solution A) was prepared under argon. Under argon, solution A was added to 3-[4-(4,4,5,5-tetramethyl-[1,3,2]dioxaborolan-2-yl)pyrazol-1-yl]pyridine (2.0 g, 7.37 mmol), 2-(6-bromopyridin-2-yl)-pyrimidine (1.74 g, 7.37 mmol) and tetrakis-(triphenylphosphine)palladium (255 mg, 0.22 mmol), and the mixture was stirred at 75 C overnight. The mixture was cooled and concentrated. Dichloromethane/water were added to the residue, and the solid formed was separated off and discarded. The filtrate was extracted and the combined organic phases were dried over magnesium sulphate and concentrated. The residue was washed initially with chloroform and then twice with diethyl ether.

Yield: 1.11 g (50% of theory), log P (HCOOH) 1.36, [M++1] 301.1

$^1$H-NMR (d$_6$-DMSO): 7.55 (m, 2H), 7.93 (d, 1H), 8.02 (m, 1H), 8.21 (d, 1H), 8.31 (m, 1H), 8.43 (s, 1H), 8.56 (m, 1H), 9.00 (m, 2H), 9.15 (m, 2H).

Alternative Synthesis to Example 1

Step 1: 6-((E)-2-Dimethylaminovinyl)pyridine-2-carbonitrile

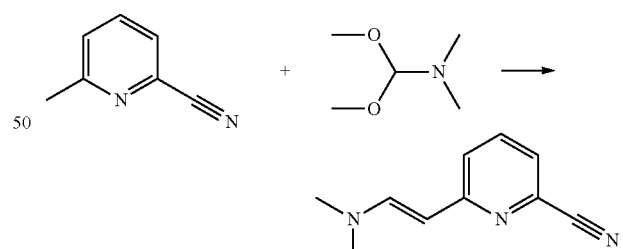

20 g (169 mmol) of 6-methylpyridine-2-carbonitrile were reacted in a mixture of in each case 100 ml of DMF and DMF-dimethyl acetal in an autoclave at 175° C. overnight. After cooling, the mixture was concentrated by evaporation, the residue was dissolved in dichloromethane, the solution was filtered, the filtrate was concentrated and the residue was subjected to distillation under reduced pressure in a kugelrohr.

Yield (proportionally calculated from 2 batches) 26.8 g (73% of theory), [M+] according to GCMS 173

¹H-NMR (CD₃CN): 2.9 (s, 6H), 5.15 (d, 1H), 7.1 (m, 2H), 7.5 (m, 2H)

Step 2: 2-(6-cyanopyridin-2-yl)-3-dimethylaminoallylidene]dimethylammonium hexafluorophosphate

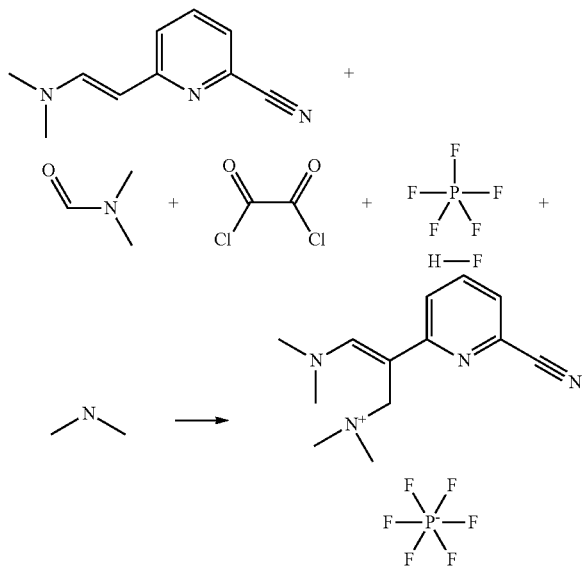

With ice-bath cooling, 7 ml (80 mmol) of oxalyl chloride were added to 5 ml (65 mmol) of DMF in about 100 ml of dichloromethane, and the mixture obtained was concentrated, resuspended in dichloromethane and, with cooling in an ice/ethanol bath, added to a solution of 7.5 g (43 mmol) of 6-((E)-2-dimethylaminovinyl)pyridine-2-carbonitrile in 100 ml of dichloromethane. The mixture was stirred for 15 min and then concentrated by evaporation. With cooling in an ice/ethanol bath, about 50 ml of ethanol and 40 ml of dimethylamine as a solution in ethanol (5.6 M, corresponds to 224 mmol) were added to the the residue. The mixture was stirred for 10 min, 6.5 ml of hexafluorophosphoric acid (60% strength aqueous solution, corresponds to 44 mol) were added, the mixture was stirred in the cooling bath for another 15 min and the crystalline precipitate formed was filtered off with suction, washed with cold ethanol and dried on a rotary evaporator.

Yield 13.1 g (81% of theory), log P (HCOOH) −0.07, [M+] 229.2 (cation without PF6−)

¹H-NMR (CD₃CN) 2.45 (br, 6H), 3.3 (s, 6H), 7.5 (s, 2H), 7.6 (m, 1H), 7.85 (m, 1H), 8.0 (m, 1H)

Step 3: 6-(1-Pyridin-3-yl-1H-pyrazol-4-yl)pyridine-2-carbonitrile

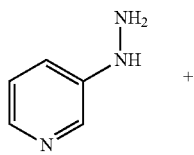

+

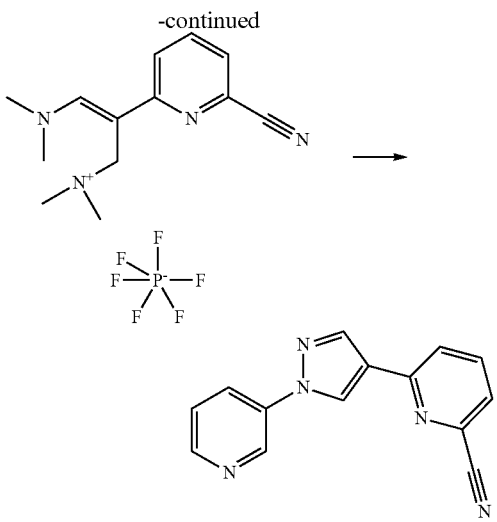

2.2 g (5.9 mmol) of 2-(6-cyanopyridin-2-yl)-3-dimethylaminoallylidene]dimethylammonium hexafluorophosphate and 0.65 g (5.9 mmol) of 3-hydrazinopyridine were dissolved in about 50 ml of dioxane/acetonitrile. The mixture was allowed to stand at RT (room temperature) overnight and then concentrated. Aq. sodium chloride, aq. Na citrate, dilute aqueous sodium hydroxide solution to pH=9 and ethyl acetate were added to the residue. The aqueous phase was then extracted twice with dichloromethane/2-propanol. The combined organic phases were dried with MgSO₄ and concentrated by evaporation, the residue was recrystallized from ethanol with filtration of the hot mixture, the filtrate was concentrated and the precipitate formed was filtered off with suction, washed with MTBE and dried on a rotary evaporator.

Yield: 0.76 g (52% of theory), log P (neutral) 1.79; [M+1] 248.1

¹H-NMR (d₆-DMSO): 7.6 (m, 1H), 7.9 (m, 1H), 8.1 (m, 2H), 8.3 (m, 1H), 8.5 (m, 1H), 8.6 (m, 1H), 9.2 (m, 1H), 9.3 (2, 1H)

Step 4: 6-(1-Pyridin-3-yl-1H-pyrazol-4-yl)pyridine-2-carboxamidine

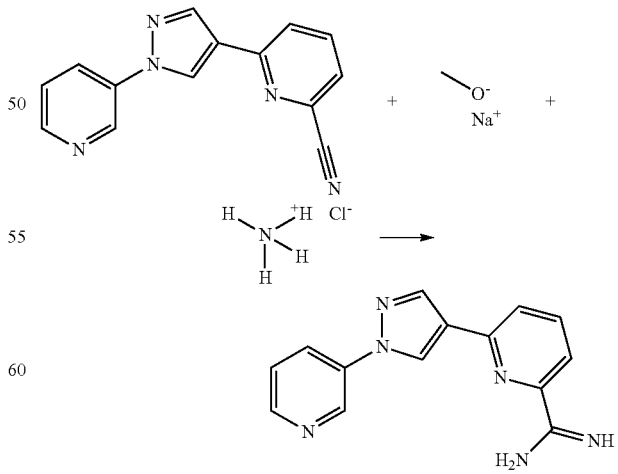

With heating, 0.7 g (2.8 mmol) of 6-(1-pyridin-3-yl-1H-pyrazol-4-yl)pyridine-2-carbonitrile was dissolved in 150 ml of abs. methanol, and 1 ml of a solution of sodium methoxide in methanol (30%, corresponds to 5.4 mmol) was added. The mixture was stirred at 65° C. until the thin-layer chromatogram (TLC) showed complete conversion, 1.5 g of ammonium chloride was added and the mixture was concentrated. The residue was boiled twice with in each case 30 ml of ethanol, the hot mixture was filtered and the combined filtrates were concentrated slightly. The mixture was allowed to stand at RT for 20 min, and the precipitate formed was filtered off with suction, washed with MTBE and dried on a rotary evaporator.

Yield: 0.74 g (95% of theory), log P (neutral) 1.99; [M+1] 265.2

¹H-NMR (d₆-DMSO) 7.5 (br, 3H), 7.65 (m, 1H), 8.2 (m, 2H), 8.35 (2H), 8.6 (d, 1H), 8.7 (s, 1H), 9.2 (m, 1H), 9.7 (s, 1H)

Step 5: 2-[6-(1-Pyridin-3-yl-1H-pyrazol-4-yl)pyridin-2-yl]pyrimidine

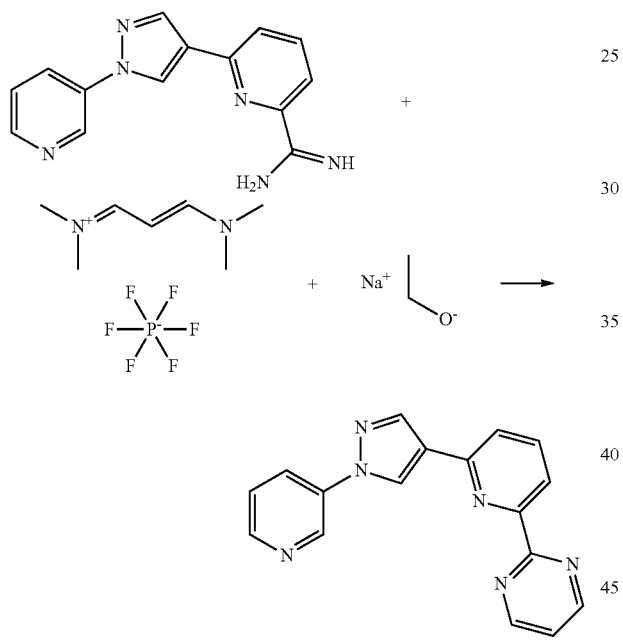

Under argon, 0.73 g (2.7 mmol) of 6-(1-pyridin-3-yl-1H-pyrazol-4-yl)pyridine-2-carboxamidine and 0.8 g (2.9 mmol) of (3-dimethylaminoallylidene)dimethylammonium hexafluorophosphate in 30 ml of ethanol were heated under reflux with 3 ml of sodium ethoxide as a solution in ethanol (21%, corresponds to 8.1 mmol) for 6 h. The mixture was concentrated, Na citrate buffer, dil. aqueous sodium hydroxide solution to pH=9, aq. NaCl and ethyl acetate/THF were added, the aqueous phase was extracted three more times with dichloromethane/2-propanol and the combined organic phases were dried with MgSO₄ and concentrated by evaporation. The residue was recrystallized from ethanol, during this operation, the mixture was briefly boiled with activated carbon and filtered whilst still hot, the filtrate was concentrated slightly and the precipitate formed was washed with MTBE and dried on a rotary evaporator. The residue was purified further by filtration through silica gel using acetone.

Yield: 0.37 g (43% of theory), log P (neutral) 1.52, [M+1] 301.1

¹H-NMR (CD₃CN): 7.45 (t, 1H), 7.5 (dd, 1H), 7.8 (d, 1H), 7.95 (t, 1H), 8.2 (m, 1H), 8.3 (d, 1H), 8.35 (s, 1H), 8.55 (d, 1H), 8.8 (s, 1H), 8.95 (m, 2H), 9.1 (d, 1H)

Example 2

Step 1:
3-Dimethylamino-1-pyrimidin-2-ylpropenone

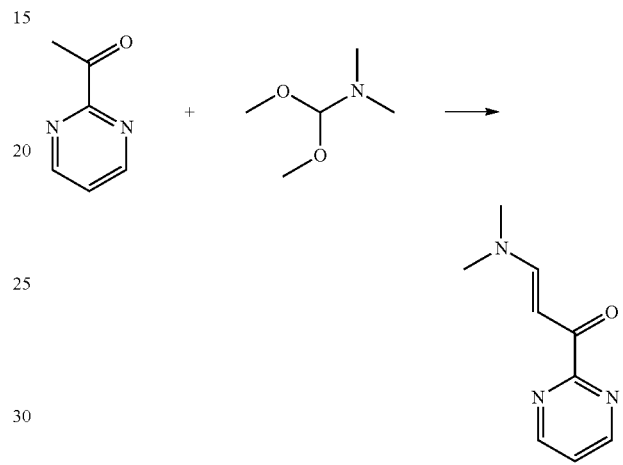

11 g (90 mmol) of 2-acetylpyrimidine and 23 g (193 mmol) of DMF-DMA (dimethylacetamide) were stirred on a very short distillation bridge at 100° C. for 1 h. During this time, a small amount of distillate was formed. The mixture was concentrated by evaporation and the residue was recrystallized from benzotrifluoride.

Yield: 11.4 g (70% of theory)

¹H-NMR (d₆-DMSO): 3.1 (s, 6H), 6 (d, 1H), 7.5 (t, 1H), 7.7 (d, 1H), 8.9 (d, 2H)

Step 2: 2-(1H-Pyrazol-3-yl)pyrimidine

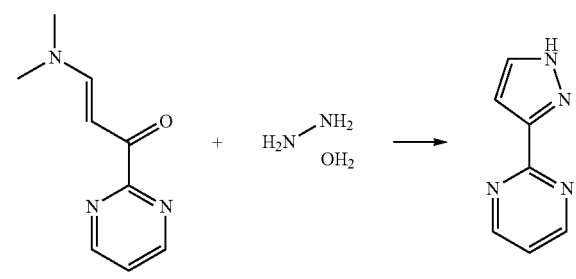

11.2 g (63.2 mmol) of 3-dimethylamino-1-pyrimidin-2-ylpropenone and 4.5 mil (92.5 mmol) of hydrazine hydrate were heated under reflux in 200 ml of EtOH for 2 h. The mixture was concentrated by evaporation and the residue was recrystallized from benzotrifluoride.

Yield: 8.72 g (94% of theory) log P (HCOOH) 0.1

$^1$H-NMR (d$_6$-DMSO) 9.65 (s, 1H), 7.4 (s, 1H), 7.6-7.8 (br, 1H), 8.85 (m, 2H), 13-13.5 (br, 1H)

Step 3: 1'-(Pyridin-3-yl)-3-(pyrimidin-2-yl)-1'H-1,4'-bipyrazole

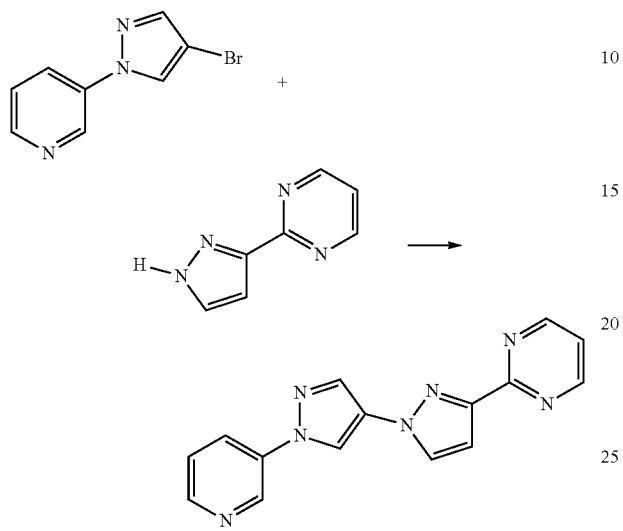

Under argon, 3-(4-bromopyrazol-1-yl)pyridine (800 mg, 3.57 mmol), 2-(1H-pyrazol-3-yl)-pyrimidine (783 mg, 5.35 mmol), caesium carbonate (1.86 g, 5.71 mmol), Cu$_2$O (29 mg, 0.17 mmol) and salicylaldoxime (97.8 mg, 0.71 mmol) were stirred in DMF (4 ml) at 130° C. After 36 h, the mixture was cooled and filtered. The filtrate was concentrated and the residue was chromatographed on silica gel initially with ethyl acetate/cyclohexane and then with ethyl acetate/isopropanol.

Yield: 274 mg (27% of theory), log P (HCOOH) 1.18, [M$^+$+1] 290.1

$^1$H-NMR (d$_6$-DMSO): 7.19 (m, 1H), 7.48 (m, 1H), 7.60 (m, 1H), 8.33 (m, 1H), 8.40 (s, 1H), 8.43 (m, 1H), 8.58 (m, 1H), 8.90 (m, 2H), 9.19 (m, 1H), 9.24 (s, 1H)

Example 3

1'-Pyridin-3-yl-3-trifluoromethyl-1'H-[1,4']bipyrazolyl

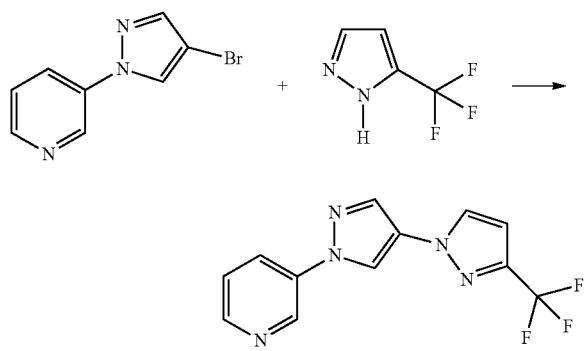

Under argon, DMF (5 ml) was added to 3-(4-bromopyrazol-1-yl)pyridine (1.00 g, 4.46 mmol), 3-trifluorometh- ylpyrazole (911 mg, 6.69 mmol), caesium carbonate (2.33 g, 7.14 mmol). Cu$_2$O (36 mg, 0.22 mmol) and salicylaldoxime (122 mg, 0.89 mmol), and the mixture was stirred at 130° C. After 24 h, the mixture was cooled to room temperature and filtered through silica gel (acetone). The solvent was removed under reduced pressure. A saturated NaCl solution was added to the residue, and the organic components were extracted with ethyl acetate. The organic phase was dried with magnesium sulphate and the solvent was removed under reduced pressure. The residue was chromatographed (ethyl acetate, cyclohexane).

Yield: 200 mg (15% of theory), log P (HCOOH) 2.27, [M$^+$+1] 280.1

$^1$H-NMR (d$_6$-DMSO): 6.97 (m, 1H), 7.57 (m, 1H), 8.28 (m, 1H), 8.31 (s, 1H), 8.44 (m, 1H), 8.58 (m, 1H), 9.13 (m, 2H).

Example 4

2-[1-(Pyridin-3-yl)-1H-pyrazol-4-yl]-6-(trifluoromethyl)pyridine

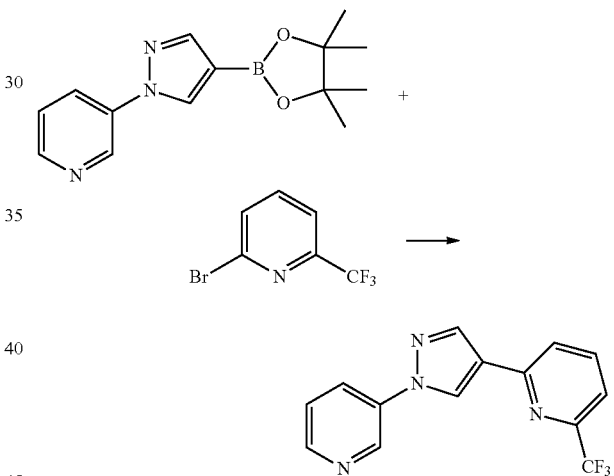

A mixture of acetonitrile (4.8 ml) and sodium carbonate (1N in water, 5.9 ml) was prepared (solution A). Under argon, solution A was added to 3-[4-(4,4,5,5-tetramethyl-[1,3,2]dioxaborolan-2-yl)pyrazol-1-yl]pyridine (400 mg, 1.47 mmol), 2-bromo-6-(trifluoromethyl)pyridine (333 mg, 1.47 mmol) and tetrakis(triphenylphosphine)palladium (51 mg, 0.04 mmol), and the mixture was stirred at 75° C. overnight. The mixture was cooled and concentrated. Ethyl acetate/water were added to the residue, and the mixture was extracted. The organic phase was dried over magnesium sulphate and concentrated. The residue was purified initially on silica gel (ethyl acetate, cyclohexane) and then by preparative HPLC (RP, acetonitrile, water).

Yield: 210 mg (49% of theory), log P (HCOOH) 2.51, [M$^+$+1] 291.1

$^1$H-NMR (d$_6$-DMSO): 7.56 (m, 1H), 7.72 (m, 1H), 8.09 (m, 2H), 8.31 (m, 1H), 8.40 (s, 1H), 8.56 (m, 1H), 9.18 (m, 2H)

Example 5

Step 1: 6-(1-Pyridin-3-yl-1H-pyrazol-4-yl)pyridine-2-carbothioamide

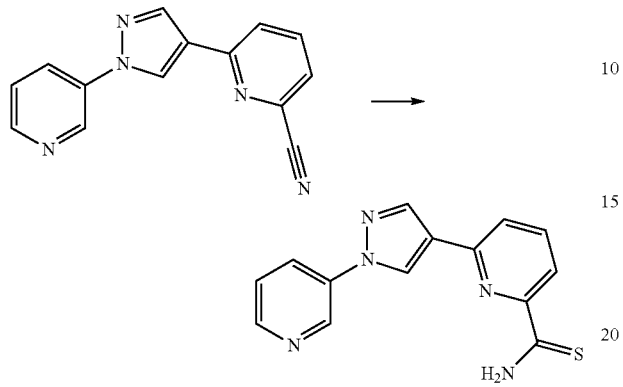

With heating, 1 g (4 mmol) of 6-(1-pyridin-3-yl-1H-pyrazol-4-yl)pyridine-2-carbonitrile was dissolved in 30 ml of pyridine, and 1.5 ml of ammonium sulphide (40% strength aqueous solution, corresponds to 8.8 mmol) were added. After 1 h, the mixture was concentrated by evaporation. The residue was recrystallized from ethanol with filtration of the hot mixture, the filtrate was concentrated slightly and the precipitate formed was filtered off with suction, washed with MTBE and dried on a rotary evaporator.

Yield: 1.2 g (98% of theory), log P (neutral) 1.77, [M+1] 282.1

$^1$H-NMR ($d_6$-DMSO): 7.6 (m, 1H), 7.9 (m, 2H), 8.3 (m, 1H), 8.4 (d, 1H), 8.55 (m, 2H), 9.25 (d, 1H), 9.4 (s, 1H)

Step 2: N-Hydroxy-6-(1-pyridin-3-yl-1H-pyrazol-4-yl)pyridine-2-carboxamidine

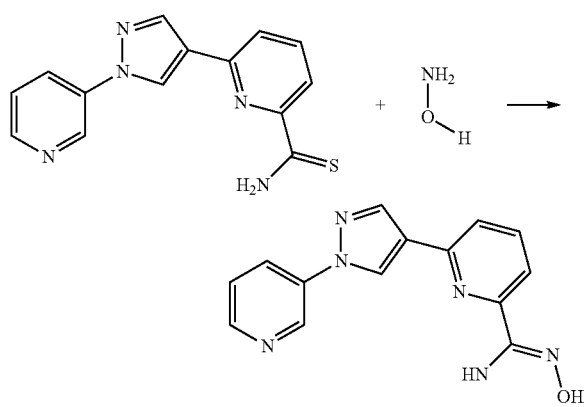

With heating, 0.4 g (1.4 mmol) of 6-(1-pyridin-3-yl-1H-pyrazol-4-yl)pyridine-2-carbothioamide were dissolved in 40 ml of dioxane-THF 1:3, 0.4 ml of hydroxylamine (50% strength aqueous solution, corresponds to 6.8 mmol) was added and the mixture was stirred at 60° C. for 1 h and then concentrated by evaporation. The crude product obtained in this manner was not purified any further.

Yield: 0.34 g, log P (neutral) 1.23, [M+H] 281.1

Step 3: 2-[1,2,4]Oxadiazol-3-yl-6-(1-pyridin-3-yl-1H-pyrazol-4-yl)pyridine

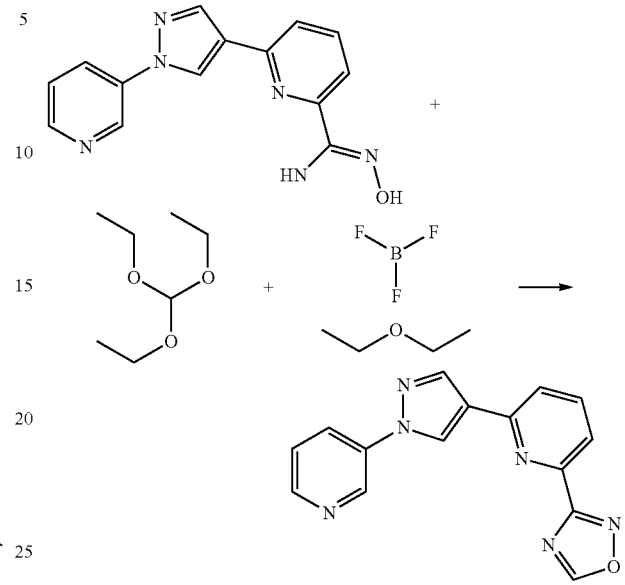

0.24 g of N-hydroxy-6-(1-pyridin-3-yl-1H-pyrazol-4-yl)pyridine-2-carboxamidine (crude product from the previous step) was dissolved in THF/triethyl orthoformate, and 0.2 g of $BF_3$-$ET_2O$ was added. After 2 h, ethyl acetate, aq. citrate buffer pH=6 and aq. NaCl were added and the aqueous phase was extracted 3 times with ethyl acetate. The combined organic phases were dried with $MgSO_4$ and concentrated by evaporation, and the residue was purified by chromatography on silica gel (petroleum ether/acetone).

Yield: 0.1 g log P (neutral) 1.54, [M+1] 291.1

$^1$H-NMR ($d_6$-DMSO): 7.55 (dd, 1H), 8.0 (m, 2H), 8.05 (m, 1H), 8.3 (m, 1H), 8.4 (s, 1H), 8.55 (m, 1H), 9.2 (m, 2H), 9.7 (s, 1H)

Example 6

2-(1-Methyl-1H-[1,2,4]triazol-3-yl)-6-(1-pyridin-3-yl-1H-pyrazol-4-yl)pyridine

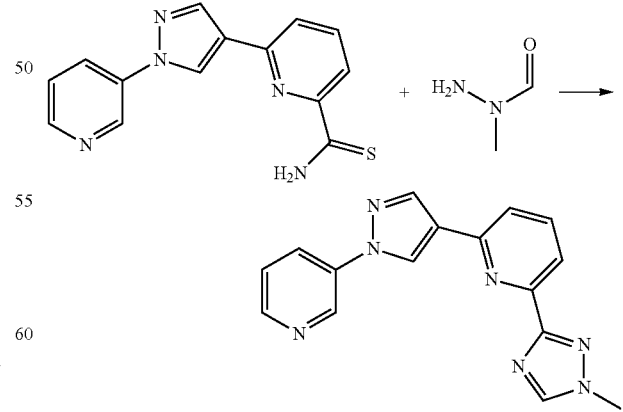

0.57 g (2 mmol) of 6-(1-pyridin-3-yl-1H-pyrazol-4-yl)pyridine-2-carbothioamide and 2.5 ml (27 mmol) of 1-methyl-1-formylhydrazine were stirred at 145° C. for 6 h. After cooling, the mixture was purified by chromatography on silica gel (cyclohexane/acetone).

Yield: 0.31 g (50% of theory), log P (neutral) 1.29; [M+1] 304.2

$^1$H-NMR (d$_6$-DMSO): 4 (s, 3H), 7.55 (m, 1H), 7.8 (m, 1H), 7.95 (m, 2H), 8.3 (m, 1H), 8.4 (s, 1H), 8.55 (s, 1H), 8.6 (m, 1H), 9.1 (s, 1H), 9.2 (m, 1H)

Example 7

3-[6-(1-Pyridin-3-yl-1H-pyrazol-4-yl)pyridin-2-yl]-[1,2,4]triazine

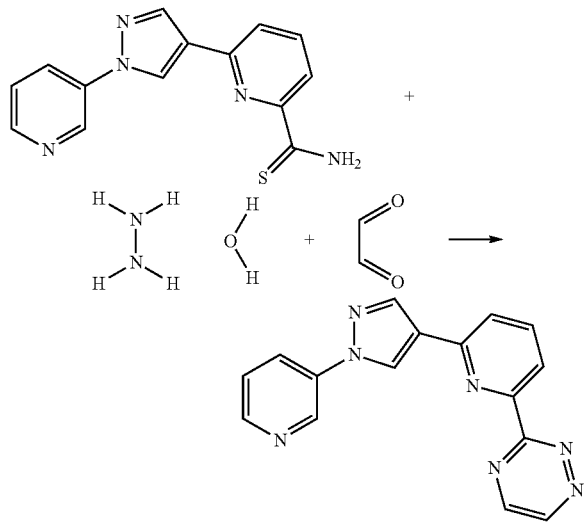

0.4 g (1.4 mmol) of 6-(1-pyridin-3-yl-1H-pyrazol-4-yl) pyridine-2-carbothioamide in 30 ml of ethanol and 0.2 ml (4.1 mmol) of hydrazine hydrate were heated under reflux for 20 min; during this time a clear mixture was formed. 0.6 ml of glyoxal (40% strength solution, corresponds to 4 mmol) was added, and the mixture was heated under reflux for a further 20 min. The mixture was filtered and concentrated by evaporation, and the residue was purified by chromatography on silica gel (petroleum ether/acetone).

Yield: 0.13 g (29% of theory), log P (neutral) 1.32, [M+1] 302.1

$^1$H-NMR (d$_6$-DMSO): 7.55 (dd, 1H), 8.0 (m, 1H), 8.1 (m, 1H), 8.3 (m, 2H), 8.45 (s, 1H), 8.55 (m, 1H), 9.1 (d, 1H), 9.2 (m, 2H), 9.5 (m, 1H)

Example 8

Step 1: N-Methoxy-N-methyl-1-(pyridin-3-yl)-1H-pyrazole-4-carboxamide

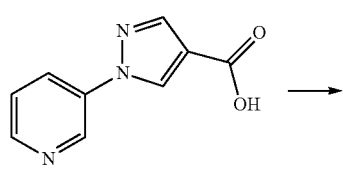

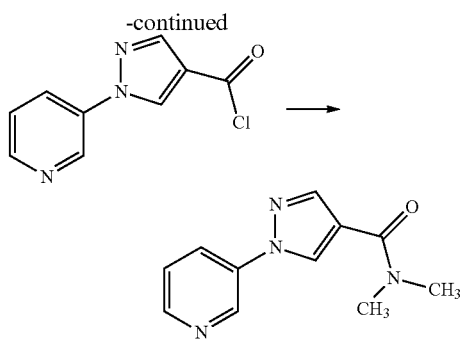

Under argon, 1-(pyridin-3-yl)-1H-pyrazole-4-carboxylic acid (7.54 g, 39.8 mmol) was initially charged in dichloromethane (190 ml), and dimethylformamide (2 ml) was added. Oxalyl chloride (14.67 g, 115 mmol) was then added at room temperature, and the mixture was stirred at room temperature for 1 h. The solvent was removed under reduced pressure on a rotary evaporator, toluene (10 ml) was added to the residue and the mixture was concentrated. The acid chloride was directly reacted further.

The acid chloride was dissolved in dioxane (125 ml), and diisopropylethylamine (Hünig base, 22.9 g, 177 mmol) was added dropwise. The mixture was then stirred at room temperature for 30 min. (Methoxyamino)methane hydrochloride (4.32 g, 44.3 mmol) was suspended in dioxane (245 mil) and added a little at a time (slightly exothermic). The mixture was stirred at room temperature overnight. Undissolved particles were filtered off. The filtrate was concentrated, and chloroform was added. The solid was filtered off with suction and purified by column chromatography (ethyl acetate).

Yield: 6.510 g (63% of theory), log P (HCOOH) 0.91, [M$^+$+1] 233.1

$^1$H-NMR (d$_6$-DMSO): 3.27 (s, 3H), 3.77 (s, 3H), 7.53-7.57 (m, 1H), 8.14 (s, 1H), 8.27-8.30 (m, 1H), 8.58 (m, 1H), 8.89 (s, 1H), 9.14 (m, 1H)

Step 2:

1-[1-(Pyridin-3-yl)-1H-pyrazol-4-yl]ethanone

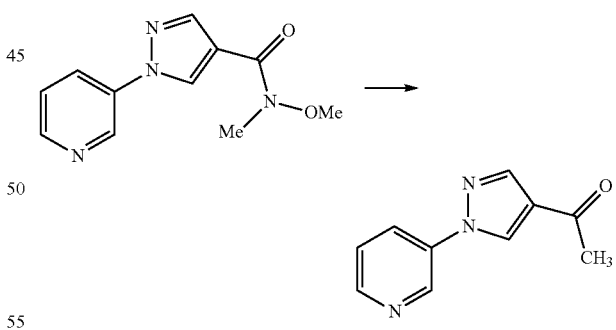

Under argon, N-methoxy-N-methyl-1-(pyridin-3-yl)-1H-pyrazole-4-carboxamide (5.00 g, 21.5 mmol) was initially charged in dry THF (200 ml) and cooled to 0° C. Methylmagnesium chloride (17.9 ml, 3M in THF) was added dropwise, and the mixture was stirred at room temperature overnight. Saturated ammonium chloride solution (160 ml) was added to the reaction mixture, and the phases were separated. The aqueous phase was once more extracted with ethyl acetate, and the combined organic phases were dried with magnesium sulphate. The solvent was removed under reduced pressure on a rotary evaporator.

Yield: 4.110 g (99% of theory), log P (HCOOH) 0.76, [M++1] 188.1

¹H-NMR (d₆-DMSO): 2.47 (s, 3H), 7.57 (m, 1H), 8.21 (s, 1H), 8.28 (m, 1H), 8.59 (m, 1H), 9.14 (m, 1H), 9.19 (s, 1H)

Step 3: (2E)-3-(Dimethylamino)-1-[1-(pyridin-3-yl)-1H-pyrazol-4-yl]prop-2-en-1-one

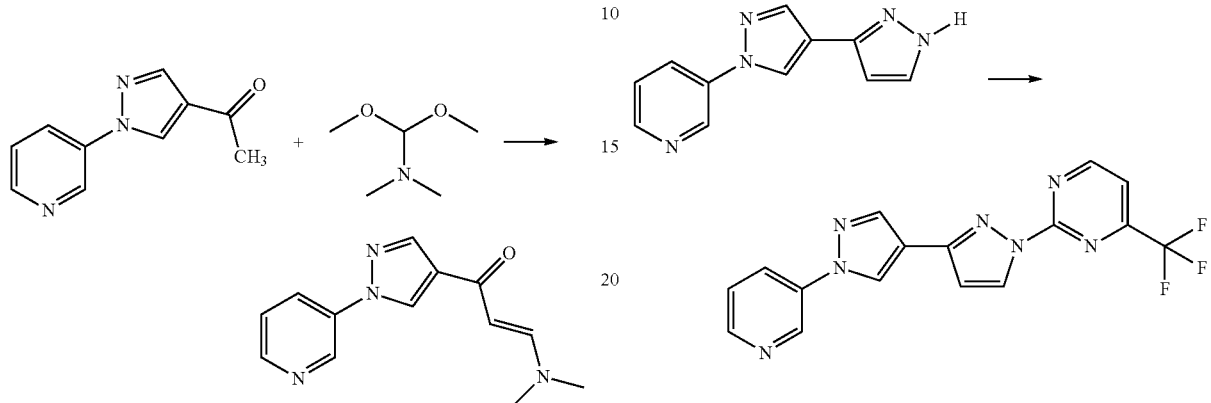

1-[1-(Pyridin-3-yl)-1H-pyrazol-4-yl]ethanone (860 mg, 4.59 mmol), dimethylformamide dimethyl acetal (6 ml) and dimethylformamide (6 ml) were combined in a round-bottom flask, and the mixture was heated at 100 C for 6 h using a distillation bridge. The mixture was then cooled and concentrated.

Yield: 1.13 g (100% of theory), log P (HCOOH) 0.93, [M++1] 243.2

¹H-NMR (d₆-DMSO): 3.01 (bs, 6H), 5.65 (d, 1H), 7.55 (m, 1H), 7.63 (d, 1H), 8.13 (s, 1H), 8.26 (m, 1H), 8.54 (m, 1H), 8.99 (s, 1H), 9.13 (m, 1H)

Step 4: 1'-(Pyridin-3-yl)-1H,1'H-3,4'-bipyrazole

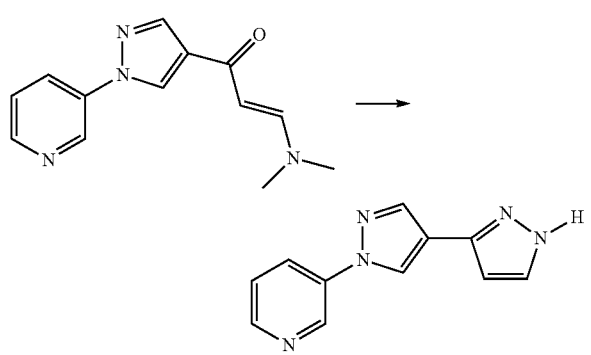

(2E)-3-(Dimethylamino)-1-[1-(pyridin-3-yl)-1H-pyrazol-4-yl]prop-2-en-1-on (800 mg, 3.30 mmol) was initially charged in ethanol (7 ml), and hydrazine (6.60 ml, 6.60 mmol) was added dropwise. The mixture was heated under reflux for 5 h and then cooled and concentrated.

Yield: 700 mg (100% of theory), log P (HCOOH) 0.79, [M++1] 212.1

¹H-NMR (d₆-DMSO): 6.51 (m, 1H), 7.54 (m, 1H), 7.73 (m, 1H), 8.09 (m, 1H), 8.22 (m, 1H), 8.52 (m, 1H), 8.81 (m, 1H), 9.11 (m, 1H), 12.65 (m, 1H)

Step 5: 1'-(Pyridin-3-yl)-1-[4-(trifluoromethyl)pyrimidin-2-yl]-1H,1'H-3,4'-bipyrazole

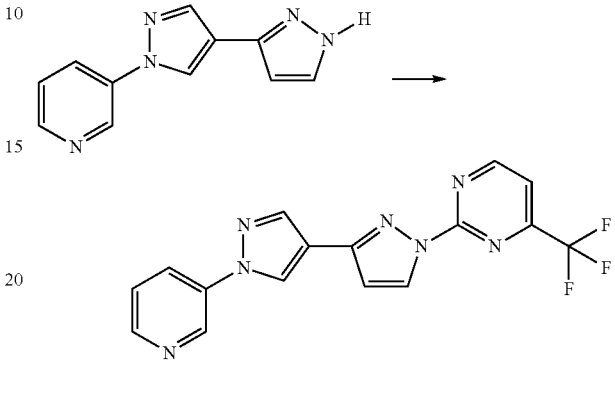

Under argon, 1'-(pyridin-3-yl)-1H,1'H-3,4'-bipyrazole (200 mg, 0.94 mmol) was initially charged in dimethylamide. Sodium hydride (56.8 mg, 1.42 mmol, 60% in paraffin oil) was added, and the mixture was stirred at room temperature for 30 min (slightly exothermic). 2-Chloro-4-trifluoromethylpyrimidine (173 mg, 0.94 mmol) was added, and the mixture was stirred at 40 C overnight. The mixture was then concentrated, and the residue was triturated with dichloromethane.

Yield: 240 mg (71% of theory), log P (HCOOH) 2.15, [M++1] 358.1

¹H-NMR (d₆-DMSO): 7.00 (m, 1H), 7.56 (m, 1H), 7.90 (d, 1H), 8.31 (m, 2H), 8.56 (m, 1H), 8.73 (m, 1H), 9.10 (s, 1H), 9.17-9.22 (m, 2H)

Example 9

2-(Pentafluoroethyl)-4-[1-(pyridin-3-yl)-1H-pyrazol-4-yl]pyrimidine

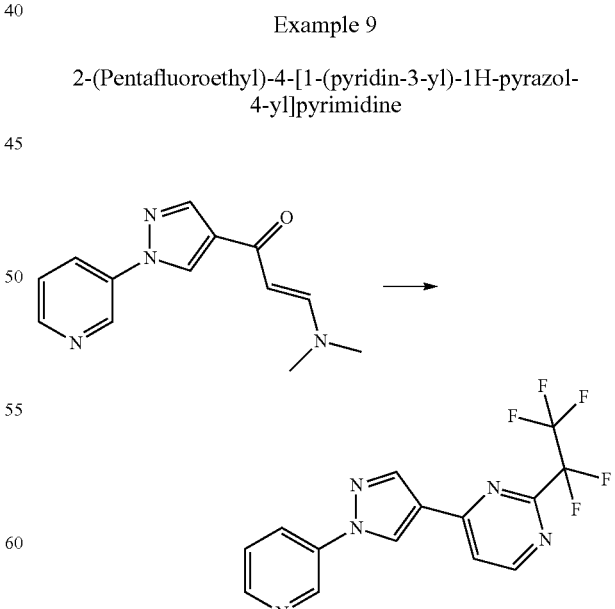

(2E)-3-(Dimethylamino)-1-[1-(pyridin-3-yl)-1H-pyrazol-4-yl]prop-2-en-1-one (200 mg, 0.82 mmol), sodium methoxide (56 mg, 1.03 mmol) and 2,2,3,3,3-pentafluoropropionamidine (166 mg, 1.02 mmol) were together initially charged in methanol (2 ml). The mixture was stirred at 55° C. overnight. The mixture was cooled and concentrated by evaporation. The residue was purified by column chromatography (acetone, isopropanol, 1:1).

Yield: 125 mg (44% of theory), log P (HCOOH) 2.7, [M++1] 342.1

$^1$H-NMR (d$_6$-DMSO): 7.58 (m, 1H), 8.13 (d, 1H), 8.33 (m, 1H), 8.52 (s, 1H), 8.61 (m, 1H), 9.03 (d, 1H), 9.18 (m, 1H), 9.37 (s, 1H)

Example 10

Step 1: 1-[6-(1-Pyridin-3-yl-1H-pyrazol-4-yl)pyridin-2-yl]ethanone

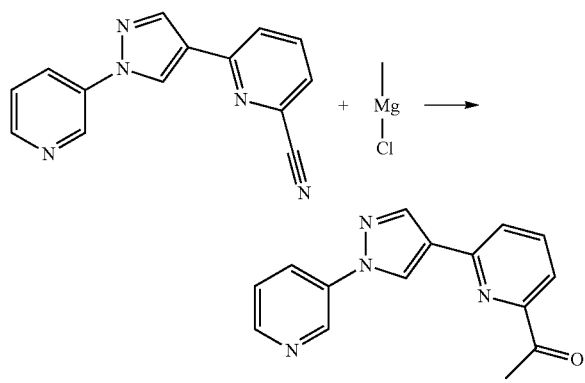

Under argon, 0.52 g (2.1 mmol) of 6-(1-pyridin-3-yl-1H-pyrazol-4-yl)pyridine-2-carbonitrile in 100 ml of THF was stirred with 1.5 ml of methylmagnesium chloride (3 M, corresponds to 24 mmol) and a few spatula tips of CuBr-dimethyl sulphide complex at room temperature for 2 h. Dilute hydrochloric acid, citrate buffer and dil. aqueous sodium hydroxide solution to pH=9 and also aq. NaCl and ethyl acetate were added. The aqueous phase was extracted 3 times with ethyl acetate, and the combined organic phases were dried with MgSO$_4$ and concentrated by evaporation. The residue was purified by chromatography on silica gel (petroleum ether/acetone).

Yield: 0.12 g (20% of theory). log P (neutral) 1.94 [M+1] 265.2

$^1$H-NMR (d$_6$-DMSO): 2.7 (s, 3H), 7.55 (m, 1H), 7.8 (m, 1H), 8.0 (m, 2H), 8.3 (m, 1H), 8.45 (s, 1H), 5.8 (m, 1H), 9.2 (m, 2H)

Step 2: 2-(2-Methyl-1,3-dioxolan-2-yl)-6-(1-pyridin-3-yl-1H-pyrazol-4-yl)pyridine

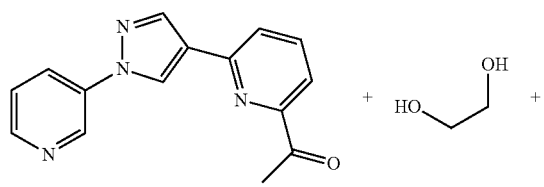

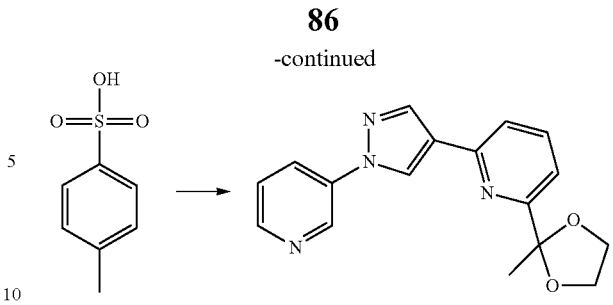

In 100 ml of 1,1-benzotrifluoride, 0.13 g (0.49 mmol) of 1-[6-(1-pyridin-3-yl-1H-pyrazol-4-yl)pyridin-2-yl]ethanone, 0.1 g (0.58 mmol) of 4-toluenesulphonic acid and 1.8 ml (32 mmol) of 1,2-ethanediol were heated under reflux in a reflux apparatus with Soxleth extractor which had been charged with 4 Å molecular sieve for 2 h. The reaction mixture concentrated by evaporation, ethyl acetate, dil. aqueous sodium hydroxide solution, citrate buffer to pH=9 and also aq. NaCl were added to the residue, the aqueous phase was extracted twice with ethyl acetate, the combined organic phases were dried with MgSO$_4$ and concentrated by evaporation. The residue was purified by chromatography on silica gel (petroleum ether/acetone).

Yield: 0.12 g (75% of theory), log P (neutral) 1.89, [M+1] 309.1

1H-NMR (d$_6$-DMSO): 1.7 (s, 3H), 3.9 (m, 2H), 4.1 (m, 2H), 7.4 (d, 1H), 7.55 (m, 1H), 7.7 (m, 1H), 7.8 (m, 1H), 8.3 (d, 1H), 8.35 (s, 1H), 8.55 (m, 1H), 9.1 (s, 1H), 9.2 (s, 1H)

Example 11

Step 1: 1-(6-Bromopyridin-2-yl)-2-methoxyethanone

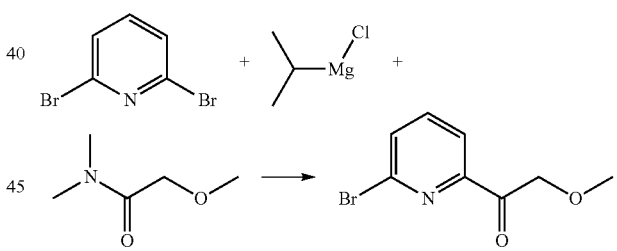

14.5 g (61.2 mmol) of 2,6-dibrompyridine were dissolved in about 50 ml of THF, and 35 ml of 2 M isopropylmagnesium chloride (corresponds to 70 mmol) were added under argon. The temperature of the mixture increased. The mixture was stirred at room temperature for another 1.5 h and at 30° C. for 2 h and then cooled in a CO$_2$/EtOH bath, and a solution of 8 g (68.2 mmol) of 2-methoxy-N,N-dimethylacetamide in THF was added, the thickened reaction material was diluted with more THF and allowed to thaw, ethyl acetate, aq. citric acid, dil. aqueous sodium hydroxide solution to pH=6, aq. NaCl were added, the aqueous phase was extracted three times with ethyl acetate and the combined organic phases were dried with MgSO$_4$ and concentrated by evaporation. The residue was distilled under reduced pressure in a kugelrohr and the distillate was recrystallized from a little benzotrifluoride.

Yield (proportionally calculated from 2 batches): 5.36 g (34% of theory) log P (neutral) 1.73 [M+1] 232.0 (heavy isotope)

¹H-NMR (CD₃CN): 3.4 (s, 3H), 4.85 (s, 2H), 7.75 (1H), 7.8 (m, 1H), 7.95 (m, 1H)

Step 2: 2-Methoxy-1-[6-(1-pyridin-3-yl-1H-pyrazol-4-yl)pyridin-2-yl]ethanone

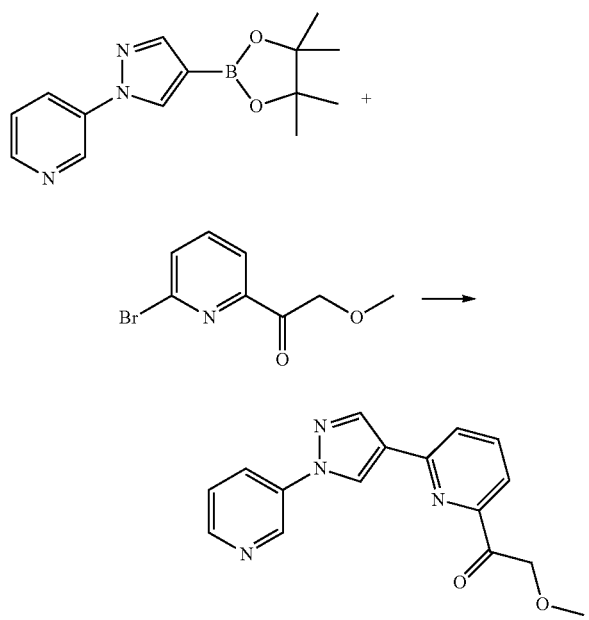

Under argon, 0.042 g (0.23 mmol) of palladium(II) chloride, 0.27 g (1 mmol) of triphenylphosphane and 1 g tetrabutylammonium chloride were stirred in 20 ml of DMF at 100° C. for 10 min, and, after cooling, 0.9 g (3.9 mmol) of 1-(6-bromopyridin-2-yl)-2-methoxyethanone, 0.98 g (3.6 mmol) of 3-[4-(4,4,5,5-tetramethyl-[1,3,2]dioxaborolan-2-yl)-pyrazol-1-yl]-pyridine and 1 g (7.2 mmol) of potassium carbonate were added. The mixture was stirred at 105° C. for another 2 h. After cooling, the mixture was concentrated by evaporation, aq. NaCl, ethyl acetate and dil. aqueous sodium hydroxide solution to pH=9 were added to the residue and the aqueous phase was extracted four times with ethyl acetate. The combined organic phases were dried with MgSO₄ and concentrated by evaporation. The residue was purified by chromatography on silica gel (petroleum ether/acetone).

Yield: 0.62 g (58% of theory) log P (HCOOH) 1.66 [M+1] 295.1

¹H-NMR (d₆-DMSO): 3.4 (s, 3H), 5.2 (s, 2H), 7.54 (m, 1H), 7.8 (m, 1H), 8.05 (m, 2H), 8.3 (m, 1H), 8.45 (s, 1H), 8.55 (m, 1H), 9.2 (m, 2H)

Step 3: 2-(1,1-Difluoro-2-methoxyethyl)-6-(1-pyridin-3-yl-1H-pyrazol-4-yl)pyridine

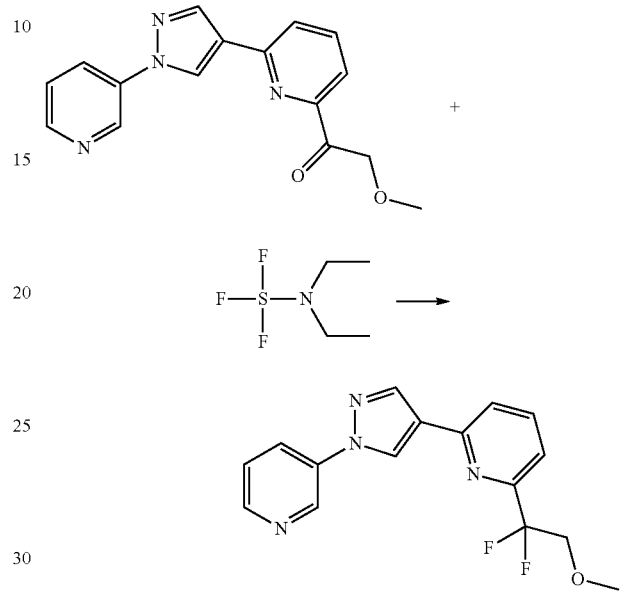

0.2 g (0.68 mmol) of 2-methoxy-1-[6-(1-pyridin-3-yl-1H-pyrazol-4-yl)pyridin-2-yl]ethanone stirred with 1.5 ml (11.3 mmol) of diethylaminosulphur trifluoride in carbon tetrachloride with two drops of trifluoroacetic acid at 77° C. in a reflux apparatus with PFA flask for 1 h. After cooling, ice, then citrate buffer, dil. aqueous sodium hydroxide solution to pH=9, aq. NaCl and ethyl acetate were added, the aqueous phase was extracted 3 times with ethyl acetate and the combined organic phases were dried with MgSO₄ and concentrated by evaporation. The residue was purified by chromatography on silica gel (petroleum ether/acetone).

Yield: 0.12 g (54% of theory), log P (neutral) 2.3 [M+1] 317.2

¹H-NMR (CD₃CN): (CD₃CN): 3.4 (s, 3H), 4.15 (t, 2H), 7.45 (m, 1H), 7.55 (m, 1H), 7.75 (d, 1H), 7.9 (dd, 1H), 8.15 (m, 1H), 8.3 (s, 1H), 8.55 (m, 1H), 8.75 (s, 1H), 9.1 (m, 1H)

Further compounds according to the invention listed in the table below were prepared analogously; in the table, Examples Nos. 1 to 11 are the end products of the preparation examples described in detail above.

| Example No. | | logP (neutral) | logP (HCOOH) | [M⁺ + 1] | ¹H-NMR Data/(solvent) |
|---|---|---|---|---|---|
| 1 | | 1.52 | 1.36 | 301.1 | (CD₃CN): 7.45 (t, 1H), 7.5 (dd, 1H), 7.8 (d, 1H), 7.95 (t, 1H), 8.2 (m, 1H), 8.3 (d, 1H), 8.35 (s, 1H), 8.55 (d, 1H), 8.8 (s, 1H), 8.95 (m, 2H) 9.1 (d, 1H) |

-continued
| Example No. | | logP (neutral) | logP (HCOOH) | [M+ + 1] | 1H-NMR Data/(solvent) |
|---|---|---|---|---|---|
| 2 | 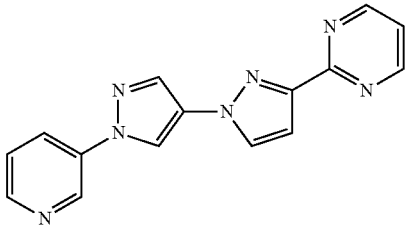 [SMILES: c1cnc(-c2ccn(-c3cnn(-c4cccnc4)c3)n2)nc1] | | 1.18 | 290.1 | (D6-DMSO): 7.19 (m, 1H), 7.48 (m, 1H), 7.60 (m, 1H), 8.33 (m, 1H), 8.40 (s, 1H), 8.43 (m, 1H), 8.58 (m, 1H), 8.90 (m, 2H), 9.19 (m, 1H), 9.24 (s, 1H) |
| 3 | 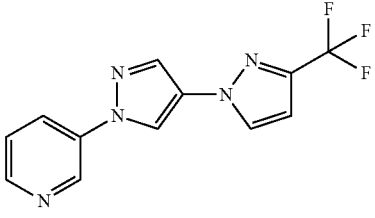 [SMILES: FC(F)(F)c1ccn(-c2cnn(-c3cccnc3)c2)n1] | | 2.27 | 280.1 | (D6-DMSO): 6.97 (m, 1H), 7.57 (m, 1H), 8.28 (m, 1H), 8.31 (s, 1H), 8.44 (m, 1H), 8.58 (m, 1H), 9.13 (m, 2H) |
| 4 | 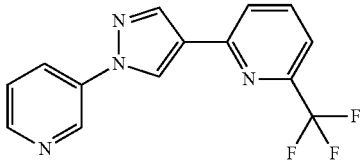 [SMILES: FC(F)(F)c1cccc(-c2cnn(-c3cccnc3)c2)n1] | | 2.51 | 291.1 | (D6-DMSO): 7.56 (m, 1H), 7.72 (m, 1H), 8.09 (m, 2H), 8.31 (m, 1H), 8.40 (s, 1H), 8.56 (m, 1H), 9.18 (m, 2H) |
| 5 | 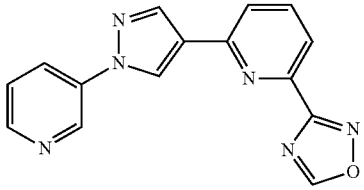 [SMILES: c1cncc(-n2cc(-c3cccc(-c4ncon4)n3)cn2)c1] | 1.54 | | 291.1 | (D6-DMSO): 7.55 (dd, 1H), 8.0 (m, 2H), 8.05 (m, 1H), 8.3 (m, 1H), 8.4 (s, 1H), 8.55 (m, 1H), 9.2 (m, 2H), 9.7 (s, 1H) |
| 6 | 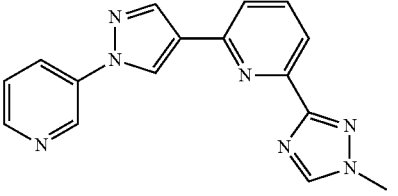 [SMILES: Cn1cnc(-c2cccc(-c3cnn(-c4cccnc4)c3)n2)n1] | 1.29 | | 304.2 | (D6-DMSO): 4 (s, 3H), 7.55 (m, 1H), 7.8 (m, 1H), 7.95 (m, 2H) 8.3 (m, 1H), 8.4 (s, 1H), 8.55 (s, 1H), 8.6 (m, 1H), 9.1 (s, 1H), 9.2 (m, 1H) |
| 7 | 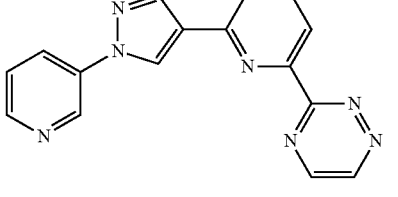 | 1.32 | | 302.1 | (D6-DMSO): 7.55 (dd, 1H), 8.0 (m, 1H), 8.1 (m, 1H), 8.3 (m, 2H), 8.45 (s, 1H), 8.55 (m, 1H), 9.1 (d, 1H), 9.2 (m, 2H), 9.5 (m, 1H) |
| 8 | 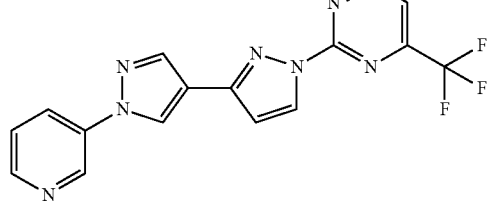 | | 2.15 | 358.1 | (D6-DMSO): 7.00 (m, 1H), 7.56 (m, 1H), 7.90 (d, 1H), 8.31 (m, 2H), 8.56 (m, 1H), 8.73 (m, 1H), 9.10 (s, 1H), 9.17-9.22 (m, 2H) |

-continued

| Example No. | Structure | logP (neutral) | logP (HCOOH) | [M⁺ + 1] | ¹H-NMR Data/(solvent) |
|---|---|---|---|---|---|
| 9 | | | 2.7 | 342.1 | (D₆-DMSO): 7.58 (m, 1H), 8.13 (d, 1H), 8.33 (m, 1H), 8.52 (s, 1H), 8.61 (m, 1H), 9.03 (d, 1H), 9.18 (m, 1H), 9.37 (s, 1H) |
| 10 | | | 1.89 | 309.1 | (D₆-DMSO): 1.7 (s, 3H), 3.9 (m, 2H), 4.1 (m, 2H), 7.4 (d, 1H), 7.55 (m, 1H), 7.7 (d, 1H), 7.8 (m, 1H), 8.3 (m, 1H), 8.35 (s, 1H), 8.55 (m, 1H), 9.1 (s, 1H), 9.2 (m, 1H) |
| 11 | | | 2.3 | 317.2 | (CD₃CN): 3.4 (s, 3H), 4.15 (t, 2H), 7.45 (m, 1H), 7.55 (m, 1H), 7.75 (d, 1H), 7.9 (dd, 1H), 8.15 (m, 1H), 8.3 (s, 1H), 8.55 (m, 1H), 8.75 (s, 1H), 9.1 (m, 1H) |
| 12 | | | 0.81 | 223.1 | (D₆-DMSO), 7.25 (m, 1H), 7.55 (m, 1H), 7.8 (m, 2H), 8.3 (m, 1H) 8.35 (s, 1H), 8.55 (m, 2H), 9.1 (s, 1H), 9.15 (m, 1H) |
| 13 | | | 1.59 | 309.2 | (D₆-DMSO): 1.50 (m, 1H), 2.08 (m, 1H), 4.02 (m, 2H), 4.18 (m, 2H), 5.53 (s, 1H), 7.40 (d, 1H), 7.56 (m, 1H), 7.77 (d, 1H), 7.86 (m, 1H), 8.30 (m, 1H), 8.33 (s, 1H), 8.54 (m, 1H), 9.07 (s, 1H), 9.16 (m, 1H) |
| 14 | | | 1.81 | 319.1 | (D₆-DMSO): 7.55 (m, 1H), 7.92 (m, 1H), 8.05 (m, 1H), 8.22 (m, 1H), 8.31 (m, 1H), 8.45 (m, 1H), 8.55 (m, 1H), 9.0 (m, 2H), 9.10 (m, 1H), 9.22 (m, 1H) |
| 15 | | | 2.13 | 292 | (D₆-DMSO): 7.60 (m, 1H), 8.11 (d, 1H), 8.32 (m, 1H), 8.55 (s, 1H), 8.60 (m, 1H), 9.00 (d, 1H), 9.19 (m, 1H), 9.39 (s, 1H) |

-continued

| Example No. | Structure | logP (neutral) | logP (HCOOH) | [M⁺ + 1] | ¹H-NMR Data/(solvent) |
|---|---|---|---|---|---|
| 16 | | | 2.1 | 388.1 | (D₆-DMSO): 3.40 (s, 3H), 7.56 (m, 1H) 7.77 (m, 2H), 8.04 (t, 1H), 8.28 (m, 1H), 8.35 (s, 1H), 8.57 (m, 1H), 9.10 (s, 1H), 9.16 (m, 1H) |
| 17 | | | 1.24 | 294.1 | (D₆-DMSO): 3.04 (s, 6H), 7.39 (d, 1H), 7.55 (m, 1H), 7.84 (d, 1H), 7.93 (t, 1H), 8.29 (m, 1H), 8.37 (s, 1H), 8.55 (m, 1H), 9.17 (s, 1H), 9.17 (m, 1H) |
| 18 | | | 1.23 | 336.2 | (D₆-DMSO): 3.67 (m, 8H), 7.46 (d, 1H), 7.56 (m, 1H), 7.86 (d, 1H), 7.95 (t, 1H), 8.36 (s, 1H), 8.55 (m, 1H), 9.10 (s, 1H), 9.17 (m, 1H) |
| 19 | | | 2.21 | 289.2 | (D₆-DMSO): 6.59 (m, 1H), 7.57 (m, 1H), 7.72 (d, 1H), 7.78 (d, 1H), 7.81 (m, 1H), 8.00 (t, 1H), 8.33 (m, 1H), 8.49 (s, 1H), 8.57 (m, 1H), 8.91 (m, 1H), 9.20 (m, 1H), 9.27 (s, 1H) |
| 20 | | | 2.05 | 257 | (D₆-DMSO): 7.34 (d, 1H), 7.56 (m, 1H), 7.78 (d, 1H), 7.88 (t, 1H), 8.30 (m, 1H), 8.36 (s, 1H), 8.56 (m, 1H), 9.13 (s, 1H), 9.17 (m, 1H) |
| 21 | | | 2.64 | 317.2 | (D₆-DMSO): 2.22 (s, 3H), 2.72 (s, 3H), 6.12 (s, 1H), 7.56 (m, 1H), 7.66 (m, 2H), 7.95 (t, 1H), 8.28 (m, 1H), 8.36 (s, 1H), 8.57 (m, 1H), 9.09 (s, 1H), 9.16 (m, 1H) |
| 22 | | | 2.38 | 291.1 | (D₆-DMSO): 7.57 (m, 1H), 8.01 (m, 1H), 8.22 (m, 1H), 8.29 (m, 1H), 8.46 (s, 1H), 8.57 (m, 1H), 8.91 (m, 1H), 9.17 (m, 1H), 9.27 (s, 1H) |

| Example No. | | logP (neutral) | logP (HCOOH) | [M+ + 1] | ¹H-NMR Data/(solvent) |
|---|---|---|---|---|---|
| 23 | | | 1.19 | 290.1 | (D₆-DMSO): 7.09 (s, 1H), 7.37 (m, 1H), 7.61 (m, 1H), 7.91 (m, 1H), 8.04 (m, 1H), 8.32 (m, 1H), 8.37 (m, 2H), 8.59 (m, 1H), 8.63 (m, 1H), 9.18 (m, 2H) |
| 24 | | | 2.18 | 302 | (D₆-DMSO): 5.69 (s, 1H), 7.48 (d, 1H), 7.54 (m, 1H), 7.81 (m, 1H), 8.29 (m, 1H), 8.34 (s, 1H), 8.55 (m, 1H), 9.12 (s, 1H), 9.17 (m, 1H) |
| 25 | | | 2.96 | 321.1 | (D₆-DMSO): 5.11 (q, 2H), 6.82 (d, 1H), 7.49 (d, 1H), 7.58 (m, 1H), 7.82 (t, 1H), 8.28 (m, 1H), 8.39 (s, 1H), 8.56 (m, 1H), 9.15 (m, 2H) |
| 26 | | | 2.51 | 294.1 | (D₆-DMSO): 2.39 (s, 3H), 6.96 (m, 1H), 7.56 (m, 1H), 8.22 (m, 1H), 8.29 (m, 1H), 8.54 (m, 1H), 9.01 (s, 1H), 9.09 (m, 1H) |
| 27 | | | 2.87 | 282.1 | (D₆-DMSO): 1.50 (s, 9H), 7.41 (d, 1H), 7.56 (m, 1H), 7.62 (d, 1H), 7.76 (t, 1H), 8.23 (m, 1H), 8.28 (s, 1H), 8.55 (m, 1H), 9.00 (s, 1H), 9.13 (m, 1H), 9.19 (m, 1H) |
| 28 | | | 1.71 | 320.1 | (D₆-DMSO): 4.07 (s, 3H), 6.85 (d, 1H), 6.90 (m, 1H), 7.56 (m, 1H), 8.24 (s, 1H), 8.29 (m, 1H), 8.54 (m, 2H), 8.69 (m, 1H), 9.03 (s, 1H), 9.17 (m, 1H) |
| 29 | | | 2.46 | 287.1 | (D₆-DMSO): 2.09 (t, 3H), 7.55 (m, 2H), 7.91 (d, 1H), 8.00 (m, 1H), 8.31 (m, 1H), 8.40 (s, 1H), 8.57 (m, 1H), 9.16 (m, 2H) |

-continued

| Example No. | | logP (neutral) | logP (HCOOH) | [M+ + 1] | 1H-NMR Data/(solvent) |
|---|---|---|---|---|---|
| 30 | | | 1.73 | 248.1 | (D6-DMSO): 7.55 (m, 1H), 7.85 (m, 1H), 8.1 (m, 2H), 8.3 (m, 1H), 8.4 (s, 1H), 8.55 (d, 1H), 9.15 (m, 1H), 9.25 (s, 1H) |
| 31 | | | 1.52 | 308.1 | (D6-DMSO): 6.92 (m, 1H), 7.57 (m, 1H), 8.23-8.34 (m, 2H), 8.56 (m, 1H), 8.64 (m, 1H), 8.93 (m, 2H), 9.05 (s, 1H), 9.19 (m, 1H) |
| 32 | | | 2.18 | 324.1 | (D6-DMSO): 2.08 (s, 3H), 3.63 (s, 3H), 4.39 (s, 2H), 6.55 (d, 1H), 7.03 (d, 1H), 7.53-7.59 (m, 2H), 8.21 (s, 1H), 8.24 (m, 1H), 8.54 (m, 1H), 8.92 (s, 1H), 9.12 (m, 1H) |
| 33 | | | 1.33 | 290.1 | (D6-DMSO): 6.92 (m, 1H), 7.45 (t, 1H), 7.56 (m, 1H), 8.26 (s, 1H), 8.29 (m, 1H), 8.55 (m, 1H), 8.69 (s, 1H), 8.87 (d, 1H), 8.90 (m, 1H), 9.06 (s, 1H), 9.17 (m, 1H) |
| 34 | | | 1.17 | 301.1 | (D6-DMSO): 7.54 (m, 1H), 7.75 (m, 1H), 7.95 (m, 1H), 8.13 (m, 2H), 8.39 (m, 3H), 8.72 (m, 1H), 9.0 (m, 2H) |
| 35 | | | 2.23 | 292.1 | (D6-DMSO): 7.57 (m, 1H), 7.79 (d, 1H), 8.36 (m, 1H), 8.44 (s, 1H), 8.59 (m, 1H), 9.17 (d, 1H), 9.22 (m, 1H), 9.26 (s, 1H) |
| 36 | | | 1.5 | 295.1 | (D6-DMSO): 4.01 (m, 2H), 4.15 (m, 2H), 5.78 (s, 1H), 7.39 (d, 1H), 7.57 (m, 1H), 7.79 (d, 1H), 7.88 (t, 1H), 8.29 (m, 1H), 8.35 (s, 1H), 8.56 (m, 1H), 9.09 (s, 1H), 9.17 (m, 1H) |

-continued
| Example No. | | logP (neutral) | logP (HCOOH) | [M+ + 1] | 1H-NMR Data/(solvent) |
|---|---|---|---|---|---|
| 37 | 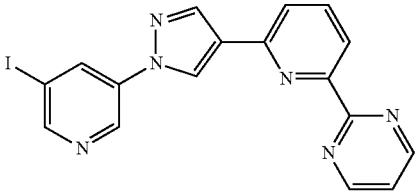 [SMILES: Ic1cncc(-n2cc(-c3cccc(-c4ncccn4)n3)cn2)c1] | | 2.37 | 426.9 | (D6-DMSO): 7.54 (m, 1H), 7.90 (m, 1H), 8.05 (m, 1H), 8.23 (m, 1H), 8.42 (m, 1H), 8.75 (m, 2H), 9.00 (m, 2H), 9.20 (m, 2H). |
| 38 | 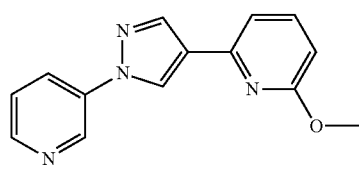 [SMILES: COc1cccc(-c2cnn(-c3cccnc3)c2)n1] | | 2.12 | 253.1 | (D6-DMSO): 3.96 (s, 3H), 6.68 (d, 1H), 7.40 (d, 1H), 7.60 (m, 1H), 7.75 (t, 1H), 8.32 (m, 1H), 8.38 (s, 1H), 8.57 (m, 1H), 9.16 (s, 1H), 9.19 (m, 1H) |
| 39 | 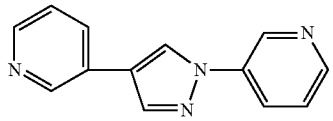 [SMILES: c1cncc(-c2cnn(-c3cccnc3)c2)c1] | | 0.39 | 223.1 | (D6-DMSO): 7.45 (m, 1H), 7.55 (m, 1H), 8.1 (m, 1H), 8.25 (m, 1H), 8.35 (s, 1H), 8.45 (m, 1H), 8.55 (d, 1H), 8.95 (m, 1H), 9.1 (s, 1H), 9.15 (m, 1H) |
| 40 | 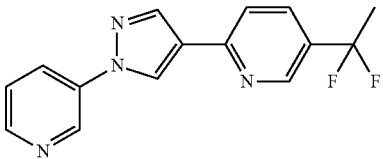 [SMILES: CC(F)(F)c1ccc(-c2cnn(-c3cccnc3)c2)nc1] | | 2.04 | 287.1 | (D6-DMSO): 2.04 (t, 3H), 7.56 (m, 1H), 7.91 (d, 1H), 8.01 (m, 1H), 8.29 (m, 1H), 8.41 (s, 1H), 8.56 (m, 1H), 8.77 (m, 1H), 9.17 (m, 1H), 9.19 (s, 1H) |
| 41 | 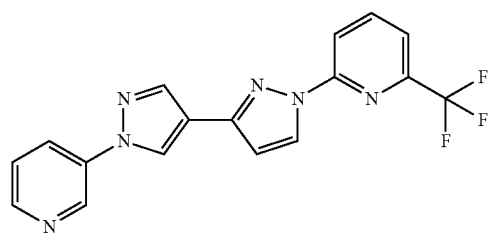 [SMILES: FC(F)(F)c1cccc(-n2ccc(-c3cnn(-c4cccnc4)c3)n2)n1] | | 3.18 | 357.1 | (D6-DMSO): 6.95 (s, 1H), 7.56 (m, 1H), 7.81 (m, 1H), 8.24-8.31 (m, 4H), 8.55 (m, 1H), 8.63 (s, 1H), 9.05 (s, 1H), 9.16 (s, 1H) |
| 42 | 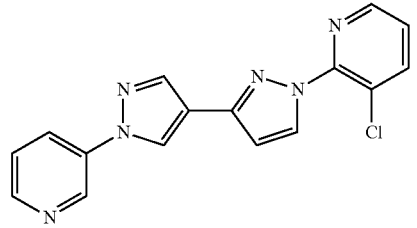 [SMILES: Clc1cccnc1-n1ccc(-c2cnn(-c3cccnc3)c2)n1] | | 1.81 | 323.1 | (D6-DMSO): 6.84 (m, 1H), 7.55 (m, 2H), 8.18 (m, 2H), 8.29 (m, 2H), 8.54 (m, 2H), 8.96 (s, 1H), 9.15 (m, 1H) |
| 43 | 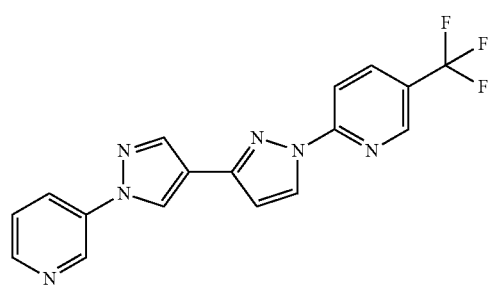 [SMILES: FC(F)(F)c1ccc(-n2ccc(-c3cnn(-c4cccnc4)c3)n2)nc1] | | 3.22 | 357.1 | (D6-DMSO): 6.96 (s, 1H), 7.56 (m, 1H), 8.17 (d, 1H), 8.28 (m, 2H), 8.38 (m, 1H), 8.55 (m, 1H), 8.72 (s, 1H), 8.85 (s, 1H), 9.05 (s, 1H), 9.17 (m, 1H) |

-continued

| Example No. | | logP (neutral) | logP (HCOOH) | [M⁺ + 1] | ¹H-NMR Data/(solvent) |
|---|---|---|---|---|---|
| 44 | | | 1.56 | 362.1 | (D₆-DMSO): 4.00 (s, 6H), 6.35 (s, 1H), 7.57 (m, 1H), 7.93 (d, 1H), 8.32 (m, 1HG), 8.53 (s, 1H), 8.58 (m, 1H), 8.93 (d, 1H), 9.18 (m, 1H), 9.33 (s, 1H) |
| 45 | | | 1.75 | 297.1 | (D₆-DMSO): 3.40 (s, 6H), 5.31 (s, 1H), 7.35 (d, 1H), 7.57 (m, 1H), 7.62 (d, 1H), 7.77 (m, 1H), 8.30 (m, 1H), 8.34 (s, 1H), 8.56 (m, 1H), 9.07 (s, 1H), 9.16 (m, 1H) |
| 46 | | | 0.86 | 302.1 | (D₆-DMSO): 7.60 (m, 1H), 7.68 (m, 1H), 8.00 (m, 1H), 8.38 (m, 1H), 8.59 (m, 2H), 9.04 (m, 3H), 9.22 (m, 1H), 9.45 (s, 1H) |
| 47 | | | 1.55 | 307 | (D₆-DMSO): 7.36 (m, 1H), 7.58 (m, 1H), 7.92 (t, 1H), 8.16 (d, 1H), 8.22 (s, 1H), 8.32-8.36 (m, 2H), 8.58 (m, 1H), 8.63 (m, 1H), 9.19 (m, 1H), 9.22 (s, 1H) |
| 48 | | | 1.52 | 302.1 | (D₆-DMSO): 3.79 (m, 2H), 6.17 (m, 1H), 6.47 (d, 1H), 6.73 (m, 1H), 6.99 (d, 1H), 7.45 (t, 1H), 7.54 (m, 1H), 8.24 (s, 1H), 8.26 (m, 1H), 8.54 (m, 1H), 8.64 (s, 1H), 9.15 (m, 1H) |
| 49 | | | 1.69 | 353.2 | |

-continued

| Example No. | | logP (neutral) | logP (HCOOH) | [M+ + 1] | 1H-NMR Data/(solvent) |
|---|---|---|---|---|---|
| 50 | 4-(trifluoromethyl)phenyl pyrazole linked to pyridin-3-yl | | 2.98 | 290.1 | (D6-DMSO): 7.55 (m, 1H), 7.75 (m, 2H), 7.95 (m, 2H), 8.3 (d, 1H), 8.35 (s, 1H), 8.55 (m, 1H), 9.15 (m, 2H) |
| 51 | pyridin-3-yl pyrazole linked to 4-chlorophenyl | | 2.71 | 256.1 | (D6-DMSO): 7.45 (m, 2H), 7.55 (m, 1H), 7.75 (m, 2H), 8.25 (m, 2H), 8.55 (br, 1H), 9 (s, 1H), 9.15 (br, 1H) |
| 52 | 3-(trifluoromethyl)phenyl pyrazole linked to pyridin-3-yl | | 2.99 | 290.1 | (D6-DMSO): 7.55-7.7 (m, 3H), 8.05 (m, 2H), 8.3 (d, 1H), 8.4 (s, 1H), 8.55 (m, 1H), 9.15 (m, 2H) |
| 53 | 4-methoxyphenyl pyrazole linked to pyridin-3-yl | | 2.12 | 252.1 | (D6-DMSO): 3.8 (s, 3H), 7 (m, 2H), 7.55 (m, 1H), 7.6 (m, 2H), 8.15 (s, 1H), 8.25 (d, 1H), 8.5 (m, 1H), 8.9 (s, 1H), 9.1 (m, 1H) |
| 54 | 2-(triazol-2-yl)-6-(1-(pyridin-3-yl)pyrazol-4-yl)pyridine | | 1.63 | 290.1 | (D6-DMSO): 7.59-7.62 (m, 1H), 7.88-7.90 (m, 1H), 7.91-7.93 (m, 1H), 8.13 (t, 1H), 8.23 (s, 2H), 8.36-8.38 (m, 1H), 8.46 (s, 1H), 8.58-8.59 (m, 1H), 9.21-9.22 (m, 1H), 9.28 (s, 1H) |
| 55 | pyridin-3-yl pyrazole linked to pyridine linked to dioxazine | | 1.4 | 308.2 | (D6-DMSO): 4.21 (t, 2H), 4.56 (t, 2H), 7.54-7.60 (m, 1H), 7.64-7.69 (m, 1H), 7.88-7.95 (m, 2H), 8.33-8.35 (m, 1H), 8.38 (s, 1H), 8.56-8.57 (m, 1H), 9.18-9.20 (m, 2H) |

-continued

| Example No. | | logP (neutral) | logP (HCOOH) | [M+ + 1] | 1H-NMR Data/(solvent) |
|---|---|---|---|---|---|
| 56 | | | 1.31 | 301.1 | (D6-DMSO): 3.42 (s, 3H), 7.59-7.63 (m, 1H), 7.87-7.89 (m, 1H), 8.11-8.13 (m, 1H), 8.20 (t, 1H), 8.33-8.36 (m, 1H), 8.54 (s, 1H), 8.58-8.60 (m, 1H), 9.21-9.22 (m, 1H), 9.37 (s, 1H) |
| 57 | | | 2.12 | 348.2 | (D6-DMSO): 4.12-4.21 (m, 2H), 7.57-7.63 (m, 2H), 7.91-7.94 (m, 1H), 7.98-8.06 (m, 2H), 8.25-8.29 (m, 1H), 8.54-8.59 (m, 1H), 8.63 (s, 1H), 9.15-9.16 (m, 1H), 9.22 (broad, NH), 9.31 (s, 1H) |
| 58 | | 1.68 | 1.54 | 321.1 | (D6-DMSO): 2.78 (s, 3H), 3.02-3.05 (m, 2H), 4.50-4.52 (m, 2H), 7.56-7.59 (m, 1H), 7.63 (d, 1H), 7.75 (d, 1H), 7.77-7.84 (m, 1H), 8.31-8.35 (m, 2H), 8.55-8.56 (m, 1H), 9.12 (s, 1H), 9.18-9.19 (m, 1H) |
| 59 | | 3.14 | 3.1 | 309.1 | (D6-DMSO): 7.77-7.79 (m, 1H), 8.10-8.19 (m, 2H), 8.36-8.39 (m, 1H), 8.49-8.50 (m, 1H), 8.60-8.61 (m, 1H), 9.12-9.13 (m, 1H), 9.32-9.33 (m, 1H) |
| 60 | | 2.12 | 1.97 | 335.2 | (D6-DMSO): 0.38-0.42 (m, 2H), 0.66-0.70 (m, 2H), 3.37-3.40 (m, 2H), 4.30-4.33 (m, 2H), 5.62 (s, 1H), 7.44-7.46 (m, 1H), 7.56-7.60 (m, 1H), 7.80-7.82 (m, 1H), 7.88-7.92 (m1H), 8.31-8.35 (m, 1H), 8.38 (s, 1H), 8.55-8.57 (m, 1H), 9.17 (s, 1H), 9.19-9.20 (m, 1H) |
| 61 | | | 1.68 | 290.2 | (D6-DMSO): 7.61-7.64 (m, 1H), 7.92-7.94 (m, 1H), 7.98-8.00 (m, 1H), 8.08-8.09 (m, 1H), 8.16 (t, 1H), 8.3-8.35 (m, 1H), 8.59-8.62 (m, 2H), 9.21-9.23 (m, 2H), 9.44-9.45 (m, 1H) |
| 62 | | | 2.16 | 331.1 | (D6-DMSO): 1.22-1.25 (m, 2H), 1.29-1.33 (m, 2H), 2.46-2.48 (m, 1H), 7.57-7.61 (m, 1H), 7.87-7.90 (m, 1H), 7.98-8.00 (m, 1H), 8.03-8.08 (m, 1H), 8.33-8.36 (m, 1H), 8.43 (s, 1H), 8.57-8.58 (m, 1H), 9.20-9.21 (m, 1H), 9.23 (s, 1H) |

-continued

| Example No. | Structure | logP (neutral) | logP (HCOOH) | [M⁺ + 1] | ¹H-NMR Data/(solvent) |
|---|---|---|---|---|---|
| 63 | | | 2.02 | 273.0 | (D6-DMSO): 6.97 (t, 1H), 7.56-7.61 (m, 2H), 7.98 (d, 1H), 8.06 (t, 1H), 8.32-8.35 (m, 1H), 8.43 (s, 1H), 8.57-8.58 (m, 1H), 9.18-9.19 (m, 1H), 9.24 (s, 1H) |
| 64 | | | 1.14 | 290.1 | (D6-DMSO): 7.61-7.64 (m, 1H), 7.85-7.98 (m, 2H), 8.03 (t, 1H), 8.14 (s, 1H), 8.27-8.30 (m, 1H), 8.59-8.60 (m, 1H), 8.67 (s, 1H), 9.16-9.17 (m, 1H), 9.42 (s, 1H) |
| 65 | | | 3.22 | 297.1 | (D6-DMSO): 1.51-1.54 (m, 2H), 1.81-1.85 (m, 2H), 7.57-7.60 (m, 1H), 7.63-7.68 (m, 2H), 7.86-7.90 (m, 1H), 8.30-8.33 (m, 1H), 8.36 (s, 1H), 8.55-8.57 (m, 1H), 9.16 (s, 1H), 9.18-9.19 (m, 1H) |
| 66 | | | 3.22 | 315.1 | (D6-DMSO): 1 (d, 6H), 2.9 (sep, 1H), 7.5 (d, 1H), 7.55 (dd, 1H), 8.4 (m, 1H), 8.0 (m, 1H), 8.3 (m, 1H), 8.4 (s, 1H), 8.55 (d, 1H), 9.15 (s, 1H), 9.2 (m, 1H) |
| 67 | | | 2.84 | 293.2 | (CD3CN): 1.2 (d, 6H), 4.25 (sep, 1H), 7.5 (m, 1H), 7.85 (m, 2H), 7.95 (m, 1H), 8.2 (m, 1H), 8.35 (s, 1H), 8.55 (m, 1H), 8.8 (s, 1H), 9.2 (m, 1H) |
| 68 | | 1.56 | 1.51 | 310.1 | (D6-DMSO): 1.47-1.50 (m, 1H), 2.02-2.09 (m, 1H), 3.96-4.02 (m, 2H), 4.16-4.20 (m, 2H), 5.54 (s, 1H), 7.41-7.43 (m, 1H), 7.79-7.81 (m, 1H), 7.89-7.93 (m, 1H), 8.46 (s, 1H), 9.17 (s, 1H), 9.24 (s, 1H), 9.40 (s, 2H) |
| 69 | | | 1.78 | 323.2 | (D6-DMSO): 1.36-1.42 (m, 1H), 1.51 (s, 3H), 1.86-1.92 (m, 1H), 3.74-3.80 (m, 2H), 3.88-3.92 (m, 2H), 7.37 (d, 1H), 7.57-7.60 (m, 1H), 7.73-7.75 (m, 1H), 7.88-7.92 (m, 1H), 8.32-8.35 (m, 1H), 8.37 (s, 1H), 8.56-8.58 (m, 1H), 9.14 (s, 1H), 9.19-9.20 (m, 1H) |

-continued
| Example No. | | logP (neutral) | logP (HCOOH) | [M⁺ + 1] | ¹H-NMR Data/(solvent) |
|---|---|---|---|---|---|
| 70 | 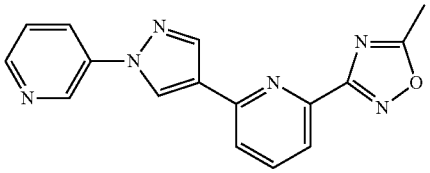 [SMILES: Cc1nc(-c2cccc(-c3cnn(-c4cccnc4)c3)n2)no1] | | 1.66 | 305.1 | (D6-DMSO): 2.71 (s, 3H), 7.61-7.64 (m, 1H), 7.91-7.94 (m, 1H), 8.00-8.02 (m, 1H), 8.06-8.09 (m, 1H), 8.37-8.41 (m, 1H), 8.45 (s, 1H), 8.58-8.60 (m, 1H), 9.22-9.23 (m, 1H), 9.26 (s, 1H) |
| 71 | 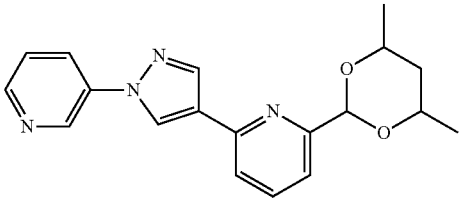 [SMILES: CC1CC(C)OC(c2cccc(-c3cnn(-c4cccnc4)c3)n2)O1] | | 2.37 | 337.2 | (D6-DMSO): 1.20 (d, 6H), 1.22 (m, 1H) 1.68 (m, 1H), 4.00 (m, 2H), 5.55 (s, 1H), 7.41 (d, 1H), 7.55 (m, 1H), 7.75 (d, 1H), 7.86 (m, 1H), 8.28 (m, 1H), 8.33 (s, 1H), 8.54 (m, 1H), 9.07 (s, 1H), 9.16 (m, 1H) |
| 72 | 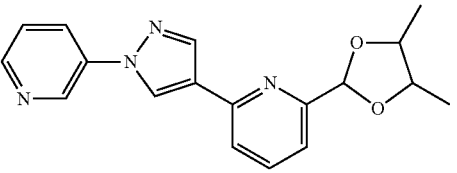 [SMILES: CC1OC(c2cccc(-c3cnn(-c4cccnc4)c3)n2)OC1C] | | | 323.2 | note: isomer mixture 58% (logP$_{HCOOH}$ 2.13) and 42% (logP$_{HCOOH}$ 2.09) |
| 73 | 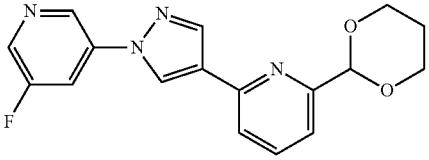 [SMILES: Fc1cncc(-n2cc(-c3cccc(C4OCCCO4)n3)cn2)c1] | 2.13 | 2.12 | 327.2 | (D6-DMSO): 1.40-1.51 (m, 1H), 2.02-2.11 (m, 1H), 3.96-4.04 (m, 2H), 4.16-4.20 (m, 2H), 5.54 (s, 1H), 7.40-7.42 (m, 1H), 7.78-7.81 (m, 1H), 7.89-7.92 (m, 1H), 8.32-8.36 (m, 1H), 8.42 (s, 1H), 8.57-8.58 (m, 1H), 9.11-9.12 (m, 1H), 9.23 (s, 1H) |
| 74 | 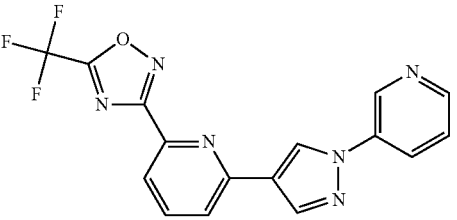 [SMILES: FC(F)(F)c1nc(-c2cccc(-c3cnn(-c4cccnc4)c3)n2)no1] | | 2.77 | 359.1 | (D6-DMSO): 7.58-7.62 (m, 1H), 8.01-8.04 (m, 1H), 8.08-8.16 (m, 2H), 8.34-8.37 (m, 1H), 8.47 (s, 1H), 8.58-8.59 (m, 1H), 9.21-9.22 (m, 1H), 9.28 (s, 1H) |
| 75 | 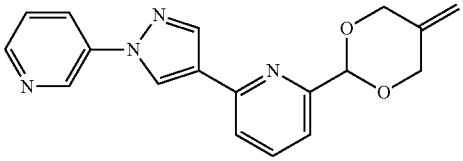 [SMILES: C=C1COC(c2cccc(-c3cnn(-c4cccnc4)c3)n2)OC1] | | 1.9 | 321.1 | (D6-DMSO): 4.49 (m, 2H), 4.55 (m, 2H), 5.06 (s, 2H), 5.69 (s, 1H), 7.39 (d, 1H), 7.54 (m, 1H), 7.78 (d, 1H), 7.86 (t, 1H), 8.30 (m, 1H), 8.33 (s1H), 8.54 (m, 1H), 9.08 (s, 1H), 9.16 (m, 1H) |
| 76 | 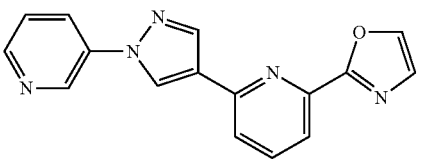 [SMILES: c1cncc(-n2cc(-c3cccc(-c4ncco4)n3)cn2)c1] | 1.69 | 1.575 | 290.1 | (D6-DMSO): 7.48-7.49 (m, 1H), 7.58-7.61 (m, 2H), 7.93-8.06 (m, 3H), 8.34-8.37 (m, 2H), 8.57-8.59 (m, 1H), 9.20-9.21 (m, 1H), 9.25 (s, 1H) |
| 77 | 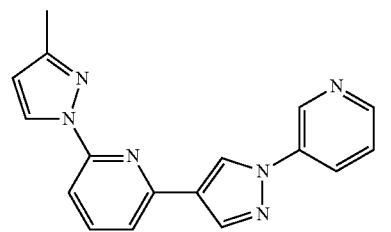 [SMILES: Cc1ccn(-c2cccc(-c3cnn(-c4cccnc4)c3)n2)n1] | | 2.51 | 303.2 | (D6-DMSO): 2.31 (s, 3H), 6.38-6.39 (m, 1H), 7.55-7.59 (m, 1H), 7.64-7.70 (m, 2H), 7.93-7.98 (m, 1H), 8.29-8.33 (m, 1H), 8.47-8.48 (m, 1H), 8.56-8.57 (m, 1H), 8.77-8.78 (m, 1H), 9.19-9.20 (m, 1H), 9.24-9.25 (m, 1H) |

-continued

| Example No. | | logP (neutral) | logP (HCOOH) | [M+ + 1] | 1H-NMR Data/(solvent) |
|---|---|---|---|---|---|
| 78 | | | 1.49 | 305.1 | (D6-DMSO): 2.21(s, 3H), 7.09 (broad, 2H), 7.60-7.63 (m, 1H), 7.81-7.83 (m, 1H), 7.92-7.95 (m, 2H), 8.29-8.33 (m, 1H), 8.57-8.59 (m, 1H), 8.63 (s, 1H), 9.19-9.20 (m, 1H), 9.47 (s, 1H) |
| 79 | | | 2.59 | 303.1 | (D6-DMSO): 2.16-2.17 (m, 3H), 7.56-7.72 (m, 4H), 7.94-7.98 (m, 1H), 8.30-8.33 (m, 1H), 8.47-8.48 (m, 1H), 8.56-8.58 (m, 1H), 8.66-8.67 (m, 1H), 9.19-9.20 (m, 1H), 9.24-9.25 (m, 1H) |
| 80 | | | 1.86 | 306.1 | (D6-DMSO): 2.04-2.13 (m, 2H), 2.57-2.62 (m, 2H), 4.16 (t, 2H), 7.49-7.52 (m, 1H), 7.54-7.58 (m, 1H), 7.79-7.83 (m, 1H), 8.13-8.16 (m, 1H), 8.26-8.30 (m, 1H), 8.34 (s, 1H), 8.52-8.56 (m, 1H), 9.07 (s, 1H), 9.16-9.17 (m, 1H) |
| 81 | | | 1.59 | 320.2 | (D6-DMSO): 1.83-1.95 (m, 4H), 2.50-2.53 (m, 2H), 4.00 (t, 2H), 7.54-7.57 (m, 2H), 7.60-7.63 (m, 1H), 7.77-7.81 (m, 1H), 8.27-8.30 (m, 1H), 8.34 (s, 1H), 8.54-8.56 (m, 1H), 9.08 (s, 1H), 9.16-9.17 (m, 1H) |
| 82 | | | 2.23 | 390.1 | (D6-DMSO): 1.36 (t, 6H), 4.44 (q, 4H), 6.28 (s, 1H), 7.56-7.60 (m, 1H), 7.92 (d, 1H), 8.29-8.33 (m, 1H), 8.52 (s, 1H) 8.58-8.60 (m, 1H), 8.93 (d, 1H), 9.17-9.18 (m, 1H), 9.32 (s, 1H) |
| 83 | | | 1.51 | 300.1 | (D6-DMSO): 2.53 (s, 6H), 7.54-7.57 (m, 1H), 8.04 (s, 1H), 8.25 (s, 1H), 8.26-8.28 (m, 1H), 8.54-8.55 (m, 1H), 8.97-8.98 (m, 1H), 9.14-9.15 (m, 1H) |
| 84 | | 1.45 | 0.9 | 292.1 | (D6-DMSO): 4.03(t, 2H), 4.47 (t, 2H), 7.55-7.61 (m, 1H), 7.85-7.89 (m, 1H), 7.92-7.98 (m, 2H), 8.32-8.37 (m, 1H), 8.39 (s, 1H), 8.56-8.59 (m, 1H), 9.18-9.23 (m, 2H) |

-continued

| Example No. | | logP (neutral) | logP (HCOOH) | [M+ + 1] | 1H-NMR Data/(solvent) |
| --- | --- | --- | --- | --- | --- |
| 85 | | | 1.66 | 295.1 | (D6-DMSO): 3.45 (s, 3H), 5.2 (s, 2H), 7.55 (dd, 1H), 7.8 (m, 1H), 8.05 (m 2H), 8.3 (d, 1H), 8.45 (s, 1H), 8.6 (m, 1H), 9.2 (m, 2H) |
| 86 | | 1.3 | 0.29 | 238.1 | (D6-DMSO): 5.88 (broad, 1H), 6.35 (d, 1H), 6.93 (d, 1H), 7.42 (t, 1H), 7.54-7.58 (m, 1H), 8.22 (m, 1H), 8.26-8.30 (m, 1H), 5.53-8.55 (m1H), 8.97 (s, 1H), 9.15 (d, 1H) |
| 87 | | 1.69 | 1.53 | 348.1 | (D6-DMSO): 4.10-4.19 (m, 2H), 7.57-7.61 (m, 1H), 7.94-7.96 (m, 1H), 8.29-8.36 (m, 2H), 8.48 (s, 1H), 8.56-8.58 (m, 1H), 9.05-9.06 (m, 1H), 9.20 (d, 1H), 9.26 (t, 1H), 9.33 (s, 1H) |
| 88 | | | 1.91 | 326.0 | (CDCl3): 7.30-7.69 (m, 3H), 7.88-7.95 (m, 1H), 8.22-9.05 (m, 6H), 9.30 (m, 1H) |
| 89 | | | 1.37 | 316.1 | (D6-DMSO): 6.36-6.40 (m, 1H), 6.50-6.53 (m, 1H), 7.50-7.58 (m, 2H), 7.65-7.68 (m, 1H), 7.83-7.86 (m, 1H), 7.98-8.03 (m, 2H), 8.28-8.32 (m, 1H), 8.40 (s, 1H), 8.55-8.56 (m, 1H), 9.16-9.18 (m, 2H) |
| 90 | | 2.53 | 2.37 | 335.1 | (D6-DMSO): 1.56-1.69 (m, 1H), 1.70-1.78 (m, 1H), 2.18-2.26 (m, 2H), 2.30-2.40 (m, 2H), 4.00-4.07 (m, 1H), 4.19 (d, 1H), 5.81 (s, 1H), 7.35 (d, 1H), 7.56-7.59 (m, 1H), 7.81 (d, 1H), 7.91 (t, 1H), 8.31-8.33 (d, 1H), 8.39 (s, 1H), 8.55-8.57 (m, 1H), 9.18-9.20 (m, 2H) |
| 91 | | | 0.84 | 280.2 | (D6-DMSO): 3.94 (s, 3H), 7.56-7.59 (m, 1H), 7.66-7.68 (m, 1H), 7.90-7.93 (m, 1H), 7.96-8.00 (m, 1H), 8.29-8.33 (m, 1H), 8.50 (s, 1H), 8.55-8.57 (m, 1H), 9.19-9.20 (m, 1H), 9.32 (s, 1H), 9.49 (broad, 1H) |

-continued

| Example No. | | logP (neutral) | logP (HCOOH) | [M⁺ + 1] | ¹H-NMR Data/(solvent) |
|---|---|---|---|---|---|
| 92 | (structure) | | 1.98 | 299.2 | (CD3CN): 3.4 (s, 3H), 3.9 (m, 2H), 5.7 (m, 1H), 7.3 (m, 1H), 7.5 (m, 1H), 7.6 (d, 1H), 7.8 (m, 1H), 8.15 (d, 1H), 8.25 (s, 1H), 8.55 (m, 1H), 8.7 (s, 1H), 9.1 (m, 1H) |
| 93 | (structure) | | 1.16 | 290.1 | |
| 94 | (structure) | | 1.31 | 280.1 | (D6-DMSO): 2.13 (s, 3H), 7.46-7.48 (m, 1H), 7.54-7.58 (m, 2H), 7.78 (t, 1H), 7.89 (d, 1H), 8.23-8.27 (m, 1H), 8.29 (s, 1H), 8.54-8.56 (m, 1H), 9.02 (s, 1H), 9.12-9.13 (m, 1H), 10.15 (s, 1H) |
| 95 | (structure) | | 1.32 | 229.0 | (D6-DMSO): 7.54-7.56 (m, 1H), 7.66 (d, 1H), 7.84 (d, 1H), 8.26 (s, 1H), 8.28-8.32 (m, 1H), 8.55-8.57 (m, 1H), 9.13 (d, 1H), 9.16-9.17 (m, 1H) |
| 96 | (structure) | 0.32 | 1.36 | 291.1 | (D6-DMSO): 5.7 (br, 1H), 7.65 (dd, 1H), 8-8.15 (m, 3H), 8.3 (d, 1H), 8.6 (m, 1H), 8.65 (s, 1H), 9.2 (m, 1H), 9.4 (s, 1H) |
| 97 | (structure) | 1.2 | 0.95 | 305.1 | (D6-DMSO): 4.4 (s, 2H), 7.6 (dd, 1H), 7.95 (d, 1H), 8.3 (d, 1H), 8.35 (d, 1H), 8.5 (s, 1H), 8.6 (d, 1H), 9.05 (m, 1H), 9.2 (m, 1H), 9.3-9.4 (m, 2H), |
| 98 | (structure) | | 0.78 | 212.1 | (D6-DMSO): 6.51 (broad, 1H), 7.48-7.57 (m, 1H), 7.71 (broad, 1H), 8.08 (broad, 1H), 8.19-8.27 (m, 1H), 8.52 (broad, 1H), 8.81 (s, 1H), 9.12 (broad, 1H) |

-continued
| Example No. | | logP (neutral) | logP (HCOOH) | [M+ + 1] | 1H-NMR Data/(solvent) |
|---|---|---|---|---|---|
| 99 | 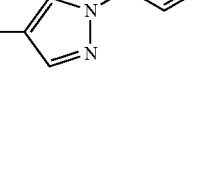 | 1.96 | 1.83 | 295.1 | (D6-DMSO): 1.37 (t, 3H), 4.39 (q, 2H), 7.57-7.61 (m, 1H), 7.88-7.93 (m, 1H), 8.01-8.07 (m, 2H), 8.32-8.35 (m, 1H), 8.42 (s, 1H), 8.56-8.58 (m, 1H), 9.18-9.22 (m, 1H), 9.33 (s, 1H) |
| 100 | 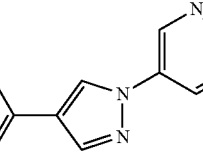 | | 0.46 | 349.1 | (D6-DMSO): 2.30-2.40 (m, 1H), 3.50 (m, 2H), 3.67 (m, 2H), 7.39-7.42 (m, 1H), 7.54-7.58 (m, 1H), 7.83-7.85 (m, 1H), 7.94 (t, 1H), 8.27-8.31 (m, 1H), 8.34-8.35 (m, 1H), 8.55-8.57 (m, 1H), 9.10-9.11 (m, 1H), 9.16-9.17 (m, 1H) |
| 101 | 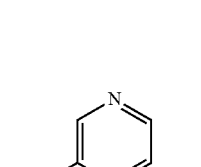 | 1.24 | 0.01 | 223.1 | (D6-DMSO): 7.55 (m, 1H), 7.7 (d, 2H), 8.25 (d, 1H), 8.4 (s, 1H), 8.55 (m, 3H), 9.15 (m, 1H), 9.2 (s, 1H) |
| 102 | 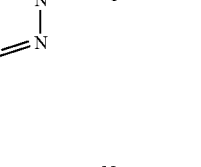 | | 1.64 | 335.1 | (D6-DMSO): 7.06 (d, 1H), 7.54-7.58 (m, 1H), 8.29-8.32 (m, 2H), 8.55-8.57 (m, 1H), 8.79-8.80 (m, 1H), 9.13-9.14 (m, 1H), 9.17-9.18 (m, 1H), 9.57 (s, 1H) |
| 103 | 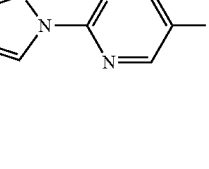 | 2.28 | 2.21 | 334.0 | (D6-DMSO): 7.60 (m, 1H), 7.75 (m, 1H), 7.80 (m, 1H), 7.99 (m, 1H), 8.32 (m, 1H), 8.38 (m, 1H), 8.60 (m, 1H), 9.20 (m, 2H), 11.9 (m, 1H) |
| 104 | 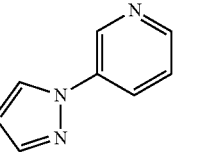 | 2.55 | 2.44 | 337.1 | (D6-DMSO): 0.78 (s, 3H), 1.25 (s, 3H), 3.66-3.69 (m, 4H), 5.44 (s, 1H), 7.44 (d, 1H), 7.53-7.56 (m, 1H), 7.76 (m, 1H), 7.88 (m, 1H), 8.28 (m, 1H), 8.30 (s, 1H), 8.54 (m, 1H), 9.07 (s, 1H), 9.15 (m1H) |
| 105 | 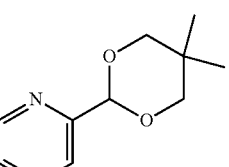 | | 1.77 | 241.1 | (D6-DMSO): 6.97-7.00 (m, 1H), 7.54-7.58 (m, 1H), 7.71-7.74 (m, 1H), 7.98-8.04 (m, 1H), 8.27-8.31 (m, 1H), 8.35 (s, 1H), 8.55-8.57 (m, 1H), 9.13-9.14 (m, 1H), 9.16-9.17 (m, 1H) |

-continued
| Example No. | | logP (neutral) | logP (HCOOH) | [M⁺ + 1] | ¹H-NMR Data/(solvent) |
|---|---|---|---|---|---|
| 106 | 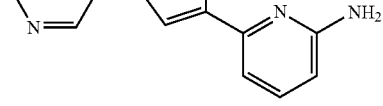 | 1.59 | 0.64 | 256.1 | (D6-DMSO): 5.90 (m, 2H), 6.38 (m, 1H), 6.95 (m, 1H), 7.43 (m, 1H), 8.28 (m, 2H), 8.57 (m, 1H), 9.05 (m, 2H) |
| 107 | 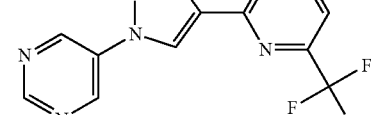 | 2.38 | 2.36 | 292.1 | (D6-DMSO): 7.77-7.79 (m, 1H), 8.11-8.19 (m, 2H), 8.54 (s, 1H), 9.19 (s, 1H), 9.34 (s, 1H), 9.41 (s, 2H) |
| 108 | 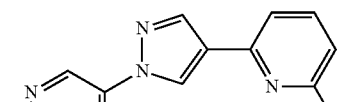 |  | 2.2 | 266.1 | (D6-DMSO): 7.89-7.94 (m, 1H), 8.12-8.15 (m, 2H), 8.34-8.38 (m, 1H), 8.52 (s, 1H), 8.60-8.61 (m, 1H), 9.12-9.13 (m, 4H), 9.37 (s, 1H) |
| 109 |  | 2.18 | 2.11 | 416.0 | (D6-DMSO): 4.12 (m, 2H), 7.60 (m, 1H), 8.32 (m, 2H), 8.60 (m, 2H), 8.87 (m, 1H), 9.20 (m, 1H), 9.45 (m, 2H) |
| 110 | 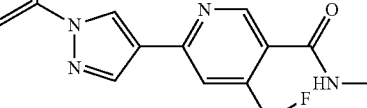 |  | 1.56 | 251.1 | (D6-DMSO): 7.54-7.59 (m, 1H), 7.77-7.82 (m, 1H), 8.07-8.09 (m, 2H), 8.29-8.34 (m, 1H), 8.45 (s, 1H), 8.56-8.58 (m, 1H), 9.17-9.18 (m, 1H), 9.22 (s, 1H), 10.05 (s, 1H) |
| 111 |  |  | 2.17 | 379.0 | (D6-DMSO): 7.55 (m, 1H), 7.91 (m, 1H), 8.03 (m, 1H), 8.21 (m, 1H), 8.45 (m, 1H), 8.65 (m, 2H), 8.99 (m, 2H), 9.20 (m, 2H) |
| 112 | 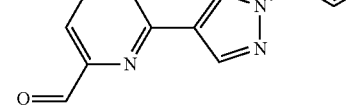 |  | 1.37 | 289.1 | (D6-DMSO): 7.54-7.57 (m, 2H), 8.11 (s, 2H), 8.18-8.23 (m, 2H), 8.51-8.55 (m, 2H), 8.79-8.82 (m, 2H), 8.84 (s, 2H), 9.09-9.10 (m, 2H) |

-continued

| Example No. | | logP (neutral) | logP (HCOOH) | [M⁺ + 1] | ¹H-NMR Data/(solvent) |
|---|---|---|---|---|---|
| 113 | | | 0.89 | 224.1 | (D6-DMSO): 7.55 (m, 1H), 7.85 (d, 1H), 8.3 (d, 1H), 8.5 (s, 1H), 8.6 (m, 1H), 8.8 (d, 1H), 9.1 (s, 1H), 9.2 (m, 1H), 9.3 (s, 1H) |
| 114 | | | 0.86 | 281.0 | (D6-DMSO): 5.96 (m, 2H), 7.56 (m, 1H), 7.70-7.83 (m, 3H), 8.28 (m, 1H), 8.49 (s, 1H), 8.55 (m, 2H), 9.18 (m, 1H), 9.30 (s, 1H), 9.72 (s, 1H) |

The intermediates below of the formula (VI) were obtained in accordance with the preparation processes described above.

| Example No | | logP (neutral) | logP (HCOOH) | [M⁺ + 1] | ¹H-NMR Data/(solvent) |
|---|---|---|---|---|---|
| VI-1 | | | 2.19 | 272.2 | (d₆-DMSO): 1.30 (s, 12H), 7.51 (m, 1H), 7.90 (s, 1H), 8.25 (m, 1H), 8.51 (m, 1H), 8.73 (s, 1H), 9.12 (m, 1H) |
| VI-2 | | | 2.88 | 290.1 | (d₆-DMSO): 1.30 (s, 12H), 7.96 (s, 1H), 8.28-8.32 (m, 1H), 8.55-8.56 (m, 1H), 8.91 (s, 1H), 9.08 (s, 1H) |
| VI-3 | | | 2.10 | 273.2 | (d₆-DMSO): 1.30 (s, 12H), 8.00 (s, 1H), 8.94 (s, 1H), 9.15 (s, 1H), 9.36 (s, 2H) |

Biological Examples

Example No. 1

*Myzus* Test (Spray Treatment)

Solvents: 78 parts by weight of acetone
1.5 parts by weight of dimethylformamide
Emulsifier 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration. Discs of leaves of Chinese cabbage (*Brassica pekinensis*) which are infested by all stages of the green peach aphid (*Myzus persicae*) are sprayed with an active compound preparation of the desired concentration.

After 6 days, the effect in % is determined. 100% means that all aphids have been killed; 0% means that none of the aphids has been killed.

In this test, for example, the following compounds of the Preparation Examples show an activity of 80% at an application rate of 500 g/ha: 35, 105, 110, 112

In this test, for example, the following compounds of the Preparation Examples show an activity of 80% at an application rate of 100 g/ha: 25

In this test, for example, the following compounds of the Preparation Examples show an activity of 90% at an application rate of 500 g/ha:
8, 13, 14, 16, 29, 40, 43, 50, 51, 61, 65, 87, 92, 95, 96, 97, 103, 106, 107, 108, 109

In this test, for example, the following compounds of the Preparation Examples show an activity of 100% at an application rate of 500 g/ha:
1, 2, 3, 4, 5, 6, 7, 9, 10, 11, 12, 15, 17, 18, 19, 21, 22, 23, 24, 26, 27, 28, 30, 31, 32, 33, 34, 36, 37, 38, 39, 42, 44, 45, 46, 47, 48, 49, 54, 56, 57, 58, 59, 60, 62, 63, 64, 66, 67, 68, 69, 70, 71, 72, 73, 74, 75, 76, 77, 78, 79, 80381, 82, 83, 84, 85, 86, 88, 89, 90, 91, 93, 94, 98, 99, 100, 101, 102

In this test, for example, the following compounds of the Preparation Examples show an activity of 100% at an application rate of 100 g/ha: 55

Example No. 2

Phaedon Test (Spray Treatment)

Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration. Discs of leaves of Chinese cabbage (*Brassica pekinensis*) are sprayed with an active compound preparation of the desired concentration and, after drying, populated with larvae of the mustard beetle (*Phaedon cochleariae*).

After 7 days, the effect in % is determined. 100% means that all beetle larvae have been killed; 0% means that none of the beetle larvae has been killed.

In this test, for example, the following compounds of the Preparation Examples show an activity of 100% at an application rate of 500 g/ha: 16, 22

Example No. 3

*Spodoptera frugiperda* Test (Spray Treatment)

Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration. Discs of maize leaves (*Zea mays*) are sprayed with an active compound preparation of the desired concentration and, after drying, populated with caterpillars of the armyworm (*Spodoptera frugiperda*).

After 7 days, the effect in % is determined. 100% means that all caterpillars have been killed; 0% means that none of the caterpillars has been killed.

In this test, for example, the following compounds of the Preparation Examples show an activity of 100% at an application rate of 500 g/ha: 16, 32

Example No. 4

*Tetranychus* Test; OP-Resistant (Spray Treatment)

Solvents: 78 parts by weight of acetone
1.5 parts by weight of dimethylformamide
Emulsifier: 0.5 part by weight of alkylaryl polyglycol ether To produce a suitable preparation of active compound, 1 part by weight of active compound is mixed with the stated amounts of solvents and emulsifier, and the concentrate is diluted with emulsifier-containing water to the desired concentration. Discs of bean leaves (*Phaseolus vulgaris*) which are infested by all stages of the greenhouse red spider mite (*Tetranychus urticae*) are sprayed with an active compound preparation of the desired concentration.

After 6 days, the effect in % is determined. 100% means that all spider mites have been killed; 0% means that none of the spider mites has been killed.

In this test, for example, the following compounds of the Preparation Examples show an activity of 90% at an application rate of 500 g/ha: 34

The invention claimed is:
1. A compound of formula (I), a salt, or an N-oxide thereof,

(I)

in which
$G^1$ represents N,
$R^1$ represents hydrogen, alkyl, haloalkyl, cycloalkyl, halogen, cyano, alkoxy, haloalkoxy, amino, alkylamino, dialkylamino or alkylthio,
$G^2$ represents $A\text{-}R^2_a$, $D\text{-}R^3_b$ or $E\text{-}R^4_c$, in which
A represents a heterocyclyl selected from the group consisting of 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, oxazolin-2-yl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 5,6-dihydro-[1,3,4]-oxadiazin-2-yl, 5,6-dihydro-[1,3,4]-thiadiazin-2-yl, 5,6-dihydro-[1,4,2]-dioxazin-3-yl, hydroxypyridyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,3-dihydrothien-2-yl, 2,3-dihydrothien-3-yl, 2,4-dihydrothien-2-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 2-piperidinyl, 3-piperidinyl, 4-piperidinyl, 1,3-dioxan- 5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, $R^2$ represents a radical selected from the group consisting of halogen, cyano, nitro, alkyl, haloalkyl, optionally substituted cycloalkyl, alkoxy, haloalkoxy, alkylthio, haloalkylthio, alkylsulphinyl, alkylsulphonyl, haloalkylsulphinyl, haloalkylsulphonyl, amino, alkylamino, dialkylamino, alkylcarbonylamino, alkoxycarbonylamino, alkoxyalkyl, haloalkoxyalkyl, alkenyl, alkynyl, optionally substituted cycloalkylalkyl, alkylcarbonyl, alkoxycarbonyl, aminocarbonyl, pyridyl and pyrimidyl (where pyridyl and pyrimidyl are optionally substituted by halogen, alkyl, haloalkyl, alkoxy and haloalkoxy), a represents a number selected from the group consisting of 0, 1, 2 and 3, D represents a heteroaryl radical selected from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl, $R^3$ represents a radical selected from the group consisting of optionally substituted cycloalkyl, optionally substituted cycloalkenyl, optionally substituted cycloalkylalkyl (where in the cycloalkyl moiety of the cycloalkylalkyl radical one or two $CH_2$ groups is optionally replaced by oxygen or sulphur, but two oxygen atoms must not be directly adjacent to one another), bis(alkoxy)alkyl, bis(haloalkoxy)alkyl, alkoxy(alkylsulphanyl)alkyl, alkoxy(alkylsulphinyl)alkyl, alkoxy(alkylsulphonyl)alkyl, bis(alkylsulphanyl)alkyl, bis(haloalkylsulphanyl)alkyl, bis(hydroxyalkylsulphanyl)alkyl, alkoxycarbonylalkyl, alpha-hydroxyimino-alkoxycarbonylalkyl, and alpha-alkoxyimino-alkoxycarbonylalkyl, or represents $C(X)NR^5R^6$ (in which X represents sulphur, or NOH, $R^5$ represents hydrogen or alkyl, and $R^6$ represents a radical selected from the group consisting of hydrogen, alkyl, haloalkyl, cyanoalkyl, alkynyl, cycloalkyl, cycloalkylalkyl, alkylcarbonyl, alkoxyalkyl, alkoxycarbonyl, alkoxycarbonylalkyl, alkylthioalkyl, aryl, arylalkyl and hetarylalkyl, or X represents sulphur, NOH, $NR^{15}$ or oxygen, $R^{15}$ represents a radical selected from the group consisting of hydrogen, alkyl, haloalkyl, cyanoalkyl, alkynyl, cycloalkyl, cycloalkylalkyl, alkylcarbonyl, alkoxyalkyl, alkoxycarbonyl, alkoxycarbonylalkyl, alkylthioalkyl, aryl, arylalkyl and hetarylalkyl, and $R^5$ and $R^6$ together with the nitrogen atom to which they are attached form a ring which optionally contains one or more further heteroatoms selected from the group consisting of NH, $NCH_3$, $NC_2H_5$, oxygen and sulphur, where two oxygen atoms must not be directly adjacent to one another, or $R^5$ and $R^{15}$ together with the nitrogen atoms to which they are attached form a ring which optionally contain one or more further heteroatoms selected from the group consisting of NH, $NCH_3$, $NC_2H_5$, oxygen and sulphur, where two oxygen atoms must not be directly adjacent to one another), or represents $NR^7R^8$ (in which $R^7$ represents hydrogen or alkyl and $R^8$ represents alkynyl, cycloalkylalkyl, alkoxy, haloalkoxy, alkoxycarbonylalkyl, alkylthioalkyl, arylalkyl or hetarylalkyl, or $R^7$ and $R^8$ together with the nitrogen atom to which they are attached form a ring which optionally contains one or more further heteroatoms selected from the group consisting of NH, $NCH_3$, $NC_2H_5$, oxygen and sulphur, where two oxygen atoms must not be directly adjacent to one another), or represents a heterocyclyl radical selected from the group consisting of dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide (where in these heterocyclyl radicals two hydrogen atoms attached to the same carbon atom are optionally replaced by $=CH_2$, $-CH_2-CH_2-$, $-CH_2-CH_2-CH_2-$ or $-CH_2-CH_2-CH_2-CH_2-$), morpholinyl, triazolinonyl, oxazolinyl, dihydrooxadiazinyl, dihydrodioxazinyl, dihydrooxazolyl, dihydrooxazinyl and pyrazolinonyl, wherein said heterocyclyl radical is optionally substituted by alkyl, haloalkyl, alkoxy or alkoxyalkyl, or represents phenyl, wherein said phenyl is optionally substituted by halogen, cyano, nitro, alkyl or haloalkyl, or represents a heteroaryl radical selected from the group consisting of pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl, wherein said heteroaryl radical is optionally substituted by halogen, nitro, alkyl, haloalkyl, alkoxy, haloalkoxy, alkoxyalkyl, alkylthio, alkylthioalkyl or cycloalkyl, or represents a heteroarylalkyl radical selected from the group consisting of triazolylalkyl, pyridylalkyl, pyrimidylalkyl and oxadiazolylalkyl, wherein said heteroarylalkyl radical is optionally substituted by alkyl, b represents a number selected from the group consisting of 1, 2 and 3, E represents aryl, $R^4$ represents a radical selected from the group consisting of nitro, amino, formyl, cyano, alkylamino, haloalkylamino, dialkylamino, alkyl, haloalkyl, optionally substituted cycloalkyl, optionally substituted cycloalkenyl, optionally substituted cycloalkylalkyl (where in the cycloalkyl moiety of the cycloalkylalkyl radical one or two $CH_2$ groups is optionally replaced by oxygen or sulphur, but two oxygen atoms must not be directly adjacent to one another), alkoxy, haloalkoxy, alkoxyalkyl, halogenated alkoxyalkyl, bis(alkoxy)alkyl, bis(haloalkoxy)alkyl, alkoxy(alkylsulphanyl)alkyl, alkoxy(alkylsulphinyl)alkyl, alkoxy(alkylsulphonyl)alkyl, bis(alkylsulphanyl)alkyl, bis(haloalkylsulphanyl)alkyl, bis(hydroxyalkylsulphanyl)alkyl, alkoxycarbonyl, alkoxycarbonylalkyl, alpha-hydroxyimino-alkoxycarbonylalkyl, and alpha-alkoxyimino-alkokycarbonylalkyl, or represents $C(X)NR^5R^6$ (in which X represents oxygen, sulphur, $NR^{15}$ or NOH, $R^5$ represents hydrogen or alkyl and $R^6$ and $R^{15}$ independently of one another represent a radical selected from the group consisting of hydrogen, alkyl, haloalkyl, cyanoalkyl, alkynyl, cycloalkyl, cycloalkylalkyl, alkylcarbonyl, alkoxyalkyl, alkoxycarbonyl, alkoxycarbonylalkyl, alkylthioalkyl, aryl, arylalkyl and hetarylalkyl, or $R^6$ represents OH, or $R^5$ and $R^6$ together with the nitrogen atom to which they are attached form a ring which optionally contain one or more further heteroatoms selected from the group consisting of NH, $NCH_3$, $NC_2H_5$, oxygen and sulphur, where two oxygen atoms must not be directly adjacent to one another, or $R^5$ and $R^{15}$ together with the nitrogen atoms to which they are attached form a ring which optionally contain one or more further heteroatoms selected from the group consisting of NH, $NCH_3$, $NC_2H_5$, oxygen and sulphur, where two oxygen atoms must not be directly adjacent to one another), or represents $NR^7R^8$ (in which $R^7$ represents hydrogen or alkyl and $R^8$ represents a radical selected from the group consisting of hydrogen, alkyl, haloalkyl, cyanoalkyl, alkynyl, cycloalkyl, cycloalkylalkyl, alkoxy, haloalkoxy, alkoxyalkyl, alkoxycarbonyl, alkoxycarbonylalkyl, alkylthioalkyl, aryl, arylalkyl and hetarylalkyl, or $R^7$ and $R^8$ together with the nitrogen atom to which they are attached form a ring which optionally contain one or more further heteroatoms selected from the group consisting of NH, $NCH_3$, $NC_2H_5$, oxygen and sulphur), or represents alkylthio, alkylsulphinyl, alkylsulphonyl, or represents a heterocyclyl radical selected from the group consisting of dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide (where in these heterocyclyl radicals two hydrogen atoms attached to the same carbon atom are optionally replaced by $=CH_2$, $-CH_2-CH_2-$, $-CH_2-CH_2-CH_2-$ or $-CH_2-CH_2-CH_2-CH_2-$), morpholinyl, triazolinonyl, oxazolinyl, dihydrooxadiazinyl, dihydrodioxazinyl, dihydrooxazolyl, dihydrooxazinyl and pyrazolinonyl (where all the heterocyclyl radicals for their part are optionally substituted by alkyl, haloalkyl, alkoxy or alkoxyalkyl), or represents phenyl, wherein said phenyl is substituted by halogen, cyano, nitro, alkyl or haloalkyl, or represents a heteroaryl radial selected from the group consisting of pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl, wherein said heteroaryl radial is optionally substituted by halogen, nitro, alkyl, haloalkyl, alkoxy, haloalkoxy, alkoxyalkyl, alkylthio, alkylthioalkyl or cycloalkyl, or represents a heteroarylalkyl radical selected from the group consisting of triazolylalkyl, pyridylalkyl, pyrimidylalkyl oxadiazolylalkyl, wherein said heteroarylalkyl radical is optionally substituted by halogen or alkyl, and c represents a number selected from the group consisting of 0, 1, 2 and 3.

2. A composition comprising at least one compound of formula (I) according to claim 1, and one or more extenders, surfactants, or combinations thereof.

3. A method for controlling pests comprising contacting a compound of formula (I) according to claim 1 with the pests, their habitat, or a combination thereof.

4. The compound according to claim 1,
in which
$R^3$ represents a heterocyclyl radical selected from the group consisting of dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide (where in these heterocyclyl radicals two hydrogen atoms attached to the same carbon atom is optionally replaced by $=CH_2$, $-CH_2-CH_2-$, $-CH_2-CH_2-CH_2-$ or $-CH_2-CH_2-CH_2-CH_2-$), morpholinyl, triazolinonyl, oxazolinyl, dihydrooxadiazinyl, dihydrodioxazinyl, dihydrooxazolyl, dihydrooxazinyl and pyrazolinonyl (where all the heterocyclyl radicals are optionally substituted by alkyl, haloalkyl, alkoxy, or alkoxyalkyl).

5. The compound according to claim 1,
in which
$R^4$ represents a heterocyclyl radical selected from the group consisting of dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide (where in these heterocyclyl radicals two hydrogen atoms attached to the same carbon atom is optionally replaced by $=CH_2$, $-CH_2-CH_2-$, $-CH_2-CH_2-CH_2-$ or $-CH_2-CH_2-CH_2-CH_2-$), morpholinyl, triazolinonyl, oxazolinyl, dihydrooxadiazinyl, dihydrodioxazinyl, dihydrooxazolyl, dihydrooxazinyl and pyrazolinonyl (where all the heterocyclyl radicals are optionally substituted by alkyl, haloalkyl, alkoxy, or alkoxyalkyl).

6. The compound according to claim 1,
in which
$R^1$ represents hydrogen or $C_1$-$C_6$-alkyl; and
$G^2$ represents A-$R^2{}_a$, D-$R^3{}_b$ or E-$R^4{}_c$,
wherein
A represents oxazolin-2-yl, 5,6-dihydro-[1,3,4]-oxadiazin-2-yl, 5,6-dihydro-[1,3,4]-thiadiazin-2-yl, 5,6-dihydro-[1,4,2]-dioxazin-3-yl or hydroxypyridyl,
$R^2$ represents a radical selected from the group consisting of halogen, cyano, nitro, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylsulphinyl, $C_1$-$C_6$-alkylsulphonyl, $C_1$-$C_6$-haloalkylsulphinyl, $C_1$-$C_6$-haloalkylsulphonyl, amino, $C_1$-$C_6$-alkylamino, di-($C_1$-$C_6$-alkyl)amino, $C_1$-$C_6$-alkylcarbonylamino, $C_1$-$C_6$-alkoxycarbonylamino, $C_1$-$C_6$-alkoxy-$C_1$-$C_6$-alkyl, $C_1$-$C_6$-haloalkoxy-$C_1$-$C_6$-alkyl, $C_2$-$C_6$-alkenyl, $C_2$-$C_6$-alkynyl, $C_3$-$C_6$-cycloalkyl-$C_1$-$C_6$-alkyl, $C_1$-$C_6$-alkylcarbonyl, $C_1$-$C_6$-alkoxycarbonyl, aminocarbonyl, pyridyl and pyrimidyl (where pyridyl and pyrimidyl are optionally substituted by halogen, $C_1$-$C_6$-alkyl, $C_1$-$C_6$-haloalkyl, $C_1$-$C_6$-alkoxy and $C_1$-$C_6$-haloalkoxy), a represents 0, 1, 2 or 3, D represents a heteroaryl radical selected from the group consisting of pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl, $R^3$ represents a radical from the group consisting of $C_3$-$C_6$-cycloalkyl-$C_1$-$C_6$-alkyl, $C_1$-$C_6$-alkoxycarbonyl-$C_1$-$C_6$-alkyl, alpha-hydroxyimino-$C_1$-$C_6$-alkoxycarbonylmethyl and alpha-$C_1$-$C_6$-alkoxyimino-$C_1$-$C_6$-alkoxycarbonylmethyl, or represents $C(X)NR^5R^6$ (in which X represents sulphur or NOH, $R^5$ represents hydrogen or $C_1$-$C_6$-alkyl, and $R^6$ represents a radical selected from the group consisting of hydrogen, $C_1$-$C_6$-alkyl, $C_1$-$C_6$-haloalkyl, cyano-$C_1$-$C_6$-alkyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy-$C_1$-$C_6$-alkyl, $C_1$-$C_6$-alkoxycarbonyl-$C_1$-$C_6$-alkyl, $C_1$-$C_6$-alkylthio-$C_1$-$C_6$-alkyl, phenyl-$C_1$-$C_6$-alkyl and hetaryl-$C_1$-$C_6$-alkyl in which hetaryl represents pyrimidyl, or X represents sulphur, NOH or oxygen and $R^5$ and $R^6$ together with the nitrogen atom to which they are attached form a 5- to 7-membered ring which optionally contains one or more heteroatoms selected from the group consisting of nitrogen, oxygen and sulphur), or represents $NR^7R^8$ (in which $R^7$ represents hydrogen or $C_1$-$C_6$-alkyl and $R^8$ represents a radical selected from the group consisting of $C_2$-$C_6$-alkynyl, $C_3$-$C_6$-cycloalkyl-$C_1$-$C_6$-alkyl, $C_1$-$C_6$-alkoxy, $C_1$-$C_6$-haloalkoxy, $C_1$-$C_6$-alkoxycarbonyl-$C_1$-$C_6$-alkyl, $C_1$-$C_6$-alkylthio-$C_1$-$C_6$-alkyl, phenyl-$C_1$-$C_6$-alkyl and hetaryl-$C_1$-$C_6$-alkyl in which hetaryl represents pyrimidyl, or $R^7$ and $R^8$ together with the nitrogen atom to which they are attached form a 5- to 7-membered ring which optionally contains one heteroatom selected from the group consisting of nitrogen, oxygen and sulphur), or represents a heterocyclyl radical selected from the group consisting of dioxanyl, dioxolanyl, morpholinyl, triazolinonyl, oxazolinyl, dihydrooxadiazinyl, dihydrodioxazinyl and pyrazolinonyl (each of which is optionally substituted by $C_1$-$C_6$-alkyl, $C_1$-$C_6$-haloalkyl, $C_1$-$C_6$-alkoxy or $C_1$-$C_6$-alkoxy-$C_1$-$C_6$-alkyl), or represents phenyl (which is substituted by halogen, cyano, nitro, $C_1$-$C_6$-alkyl or $C_1$-$C_6$-haloalkyl), or represents a heteroaryl radical selected from the group consisting of pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (each of which is optionally substituted by halogen, nitro, $C_1$-$C_6$-alkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyl, $C_1$-$C_6$-alkylthio, $C_1$-$C_6$-alkylthio-$C_1$-$C_6$-alkyl or $C_3$-$C_6$-cycloalkyl), or represents a heteroarylalkyl radical selected from the group consisting of triazolyl-$C_1$-$C_6$-alkyl, pyridyl-$C_1$-$C_6$-alkyl, pyrimidyl-$C_1$-$C_6$-alkyl and oxadiazolyl-$C_1$-$C_6$-alkyl (each of which is optionally substituted by $C_1$-$C_6$-alkyl), b represents 0, 1, 2 or 3, E represents phenyl, $R^4$ represents cyano, $C_1$-$C_6$-haloalkyl, $C_1$-$C_6$-alkoxy, $C_1$-$C_6$-haloalkoxy, dioxolanyl or dihydrodioxazinyl, and c represents 1, 2 or 3.

7. The compound according to claim 1, in which $R^1$ represents hydrogen; and $G^2$ represents $A$-$R^2_a$, $D$-$R^3_b$ or $E$-$R^4_c$, wherein A represents oxazolin-2-yl, 5,6-dihydro-[1,3,4]-oxadiazin-2-yl 5,6-dihydro-[1,3,4]-thiadiazin-2-yl or 5,6-dihydro-[1,4,2]-dioxazin-3-yl, $R^2$ represents a radical selected from the group consisting of halogen, cyano, nitro, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-alkylsulphonyl, $C_1$-$C_4$-haloalkylsulphinyl, $C_1$-$C_4$-haloalkylsulphonyl, amino, $C_1$-$C_4$-alkylamino, di-($C_1$-$C_4$-alkyl)amino, $C_1$-$C_4$-alkylcarbonylamino, $C_1$-$C_4$-alkoxycarbonylamino, $C_1$-$C_4$-alkoxy-$C_1$-$C_4$-alkyl, $C_1$-$C_4$-haloalkoxy-$C_1$-$C_4$-alkyl, $C_2$-$C_4$-alkenyl, $C_2$-$C_4$-alkynyl, $C_3$-$C_6$-cycloalkyl-$C_1$-$C_4$-alkyl, $C_1$-$C_4$-alkylcarbonyl, $C_1$-$C_4$-alkoxycarbonyl, aminocarbonyl, pyridyl and pyrimidyl (where pyridyl and pyrimidyl are optionally substituted by halogen, $C_1$-$C_4$-alkyl, $C_1$-$C_4$-haloalkyl, $C_1$-$C_4$-alkoxy or $C_1$-$C_4$-haloalkoxy), a represents 0, 1, 2 or 3, D represents a heteroaryl radical selected from the group consisting of pyrid-2-yl, pyrid-3-yl, pyrimid-2-yl, pyrimid-4-yl, imidazolyl, pyrazol-1-yl, pyrazol-3-yl, pyrazinyl, 1,2,3-triazinyl, 1,2,4-triazinyl, 1,3,5-triazinyl, thiazol-2-yl, thiazol-4-yl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl and oxazolyl, $R^3$ represents a radical selected from the group consisting of $C_3$-$C_6$-cycloalkyl-$C_1$-$C_4$-alkyl, $C_1$-$C_4$-alkoxycarbonyl-$C_1$-$C_4$-alkyl, alpha-hydroxyimino-$C_1$-$C_4$-alkoxycarbonylmethyl and alpha-$C_1$-$C_4$-alkoxyimino-$C_1$-$C_4$-alkoxycarbonylmethyl, or represents $C(X)NR^5R^6$ (in which X represents sulphur, $R^5$ represents hydrogen or $C_1$-$C_4$-alkyl and $R^6$ represents a radical selected from the group consisting of hydrogen, $C_1$-$C_5$-alkyl, $C_1$-$C_4$-haloalkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkylthio-$C_1$-$C_4$-alkyl and phenyl-$C_1$-$C_4$-alkyl, or X represents sulphur or oxygen and $R^5$ and $R^6$ together with the nitrogen atom to which they are attached form a 5- to 7-membered ring which optionally contains one heteroatom selected from the group consisting of nitrogen, oxygen and sulphur), or represents $NR^7R^8$ (in which $R^7$ represents hydrogen or $C_1$-$C_4$-alkyl and $R^8$ represents a radical selected from the group consisting of $C_2$-$C_4$-alkynyl, $C_3$-$C_6$-cycloalkyl-$C_1$-$C_4$-alkyl, $C_1$-$C_4$-alkoxy, $C_1$-$C_4$-haloalkoxy, $C_1$-$C_4$-alkoxycarbonyl-$C_1$-$C_4$-alkyl, $C_1$-$C_4$-alkylthio-$C_1$-$C_4$-alkyl and phenyl-$C_1$-$C_4$-alkyl, or $R^7$ and $R^8$ together with the nitrogen atom to which they are attached form a 5- or 6-membered ring which optionally contains one heteroatom selected from the group consisting of oxygen, sulphur and nitrogen), or represents a heterocyclyl radical selected from the group consisting of dioxanyl, dioxolanyl, morpholinyl, triazolinonyl, oxazolinyl, dihydrooxadiazinyl, dihydrodioxazinyl and pyrazolinonyl (each of which is optionally substituted by $C_1$-$C_4$-alkyl or $C_1$-$C_4$-haloalkyl), or represents phenyl (which is optionally substituted by halogen, cyano, nitro, $C_1$-$C_4$-alkyl or $C_1$-$C_4$-haloalkyl), or represents a heteroaryl radical selected from the group consisting of pyridyl, pyridyl N-oxide, pyrimidyl, imidazolyl, pyrazolyl, oxazolyl, thiazolyl, furanyl, thienyl, triazolyl, oxadiazolyl, thiadiazolyl, pyrazinyl, triazinyl, tetrazinyl and isoquinolinyl (each of which is optionally substituted by halogen, nitro, $C_1$-$C_4$-alkyl, $C_1$-$C_4$-haloalkyl, $C_1$-$C_4$-alkoxy, haloalkoxy, $C_1$-$C_4$-alkoxy-$C_1$-$C_4$-alkyl, $C_1$-$C_4$-alkylthio-$C_1$-$C_4$-alkyl or $C_3$-$C_6$-cycloalkyl), or represents a heteroarylalkyl radical selected from the group consisting of triazolyl-$C_1$-$C_4$-alkyl, pyridyl-$C_1$-$C_4$-alkyl, pyrimidyl-$C_1$-$C_4$-alkyl and oxadiazolyl-$C_1$-$C_4$-alkyl (each of which is optionally substituted by $C_1$-$C_4$-alkyl), b represents 0, 1 and 2, E represents phenyl, $R^4$ represents cyano, $C_1$-$C_4$-haloalkyl, $C_1$-$C_4$-alkoxy or $C_1$-$C_4$-haloalkoxy, and c represents 1 or 2.

8. The compound according to claim 1,
in which
$R^1$ represents hydrogen; and
$G^2$ represents A-$R^2_a$ or D-$R^3_b$,
wherein
A represents oxazolin-2-yl, 5,6-dihydro-[1,3,4]-oxadiazin-2-yl, or 5,6-dihydro-[1,3,4]-thiadiazin-2-yl,
$R^2$ represents pyridyl and pyrimidyl which are optionally substituted by halogen, $C_1$-$C_4$-alkyl, $C_1$-$C_4$-haloalkyl, $C_1$-$C_4$-alkoxy or $C_1$-$C_4$-haloalkoxy,
a represents 0, 1 or 2,
D represents pyrazol-1-yl, pyrazol-3-yl, pyrid-3-yl, pyrid-2-yl, pyramid-2-yl pyramid-4-yl, thiazol-2-yl or thiazol-4-yl,
$R^3$ represents a radical selected from the group consisting of $C_3$-$C_6$-cycloalkyl-$C_1$-$C_4$-alkyl and alpha-hydroxyimino-$C_1$-$C_4$-alkoxycarbonylmethyl, or
represents C(X)NR$^5$R$^6$ (in which X represents sulphur, $R^5$ represents hydrogen and $R^6$ represents a radical selected from the group consisting of hydrogen, $C_1$-$C_5$-alkyl, $C_1$-$C_4$-haloalkyl, cyano-$C_1$-$C_4$-alkyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkylthio-$C_1$-$C_4$-alkyl and phenyl-$C_1$-$C_4$-alkyl, or X represents sulphur or oxygen and $R^5$ and $R^6$ together with the nitrogen atom to which they are attached form a 5- to 7-membered ring which optionally contains a heteroatom selected from the group consisting of nitrogen, oxygen and sulphur), or
represents NR$^7$R$^8$ (in which $R^7$ represents hydrogen or methyl and $R^8$ represents $C_1$-$C_4$-alkoxycarbonyl-$C_1$-$C_4$-alkyl, or $R^7$ and $R^8$ together with the nitrogen atom to which they are attached form a 5- or 6-membered ring which optionally contains an oxygen atom, or
represents a heterocyclyl radical selected from the group consisting of dioxanyl, dioxolanyl, morpholinyl, triazolinonyl, oxazolinyl, dihydrooxadiazinyl, dihydrodioxazinyl and pyrazolinonyl (each of which is optionally substituted by $C_1$-$C_4$-alkyl or $C_1$-$C_4$-haloalkyl), or represents phenyl (which is optionally substituted by halogen), or represents a heteroaryl radical selected from the group consisting of pyridyl, pyridyl N-oxide, pyrimidinyl, pyrazolyl, thiazolyl, furanyl, thienyl, triazolyl, oxadiazolyl, thiadiazolyl, pyrazinyl, triazinyl, and isoquinolinyl (each of which is optionally substituted by halogen, nitro, $C_1$-$C_4$-alkyl, $C_1$-$C_4$-haloalkyl, $C_1$-$C_4$-alkoxy, or $C_3$-$C_6$-cycloalkyl), or represents a heteroarylalkyl radical selected from the group consisting of triazolyl-$C_1$-$C_4$-alkyl, pyridyl-$C_1$-$C_4$-alkyl, pyrimidinyl-$C_1$-$C_4$-alkyl and oxadiazolyl-$C_1$-$C_4$-alkyl (each of which is optionally substituted by $C_1$-$C_4$-alkyl), and b represents 0, 1 or 2.

9. A compound of formula (I), a salt, or an N-oxide thereof,

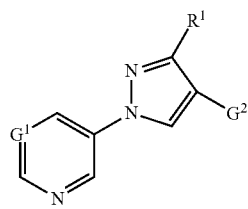

(I)

in which
$G^1$ represents N,
$R^1$ represents alkyl, haloalkyl, cycloalkyl, halogen, cyano, alkoxy, haloalkoxy, amino, alkylamino, dialkylamino or alkylthio,
$G^2$ represents E-$R^4_c$, in which
E represents aryl,
$R^4$ represents a radical selected from the group consisting of halogen, nitro, amino, formyl, cyano, alkylamino, haloalkylamino, dialkylamino, alkyl, haloalkyl, optionally substituted cycloalkyl, optionally substituted cycloalkenyl, optionally substituted cycloalkylalkyl (where in the cycloalkyl moiety of the cycloalkylalkyl radical one or two $CH_2$ groups is optionally replaced by oxygen or sulphur, but two oxygen atoms must not be directly adjacent to one another), alkoxy, haloalkoxy, alkoxyalkyl, halogenated alkoxyalkyl, bis(alkoxy)alkyl, bis(haloalkoxy)alkyl, alkoxy(alkylsulphanyl)alkyl, alkoxy(alkylsulphinyl)alkyl, alkoxy(alkylsulphonyl)alkyl, bis(alkylsulphanyl)alkyl, bis(haloalkylsulphanyl)alkyl, bis(hydroxyalkylsulphanyl)alkyl, alkoxycarbonyl, alkoxycarbonylalkyl, alpha-hydroxyiminoalkoxycarbonylalkyl, and alpha-alkoxyiminoalkokycarbonylalkyl, or
represents C(X)NR$^5$R$^6$ (in which X represents oxygen, sulphur, NR$^{15}$ or NOH, $R^5$ represents hydrogen or alkyl and $R^6$ and $R^{15}$ independently of one another represent a radical selected from the group consisting of hydrogen, alkyl, haloalkyl, cyanoalkyl, alkynyl, cycloalkyl, cycloalkylalkyl, alkylcarbonyl, alkoxyalkyl, alkoxycarbonyl, alkoxycarbonylalkyl, alkylthioalkyl, aryl, arylalkyl and hetarylalkyl, or $R^6$ represents OH, or $R^5$ and $R^6$ together with the nitrogen atom to which they are attached form a ring which optionally contain one or more further heteroatoms selected from the group consisting of NH, NCH$_3$, NC$_2$H$_5$, oxygen and sulphur, where two oxygen atoms must not be directly adjacent to one another, or R$^5$ and R$^{15}$ together with the nitrogen atoms to which they are attached form a ring which optionally contain one or more further heteroatoms selected from the group consisting of NH, NCH$_3$, NC$_2$H$_5$, oxygen and sulphur, where two oxygen atoms must not be directly adjacent to one another), or represents NR$^7$R$^8$ (in which R$^7$ represents hydrogen or alkyl and R$^8$ represents a radical selected from the group consisting of hydrogen, alkyl, haloalkyl, cyanoalkyl, alkynyl, cycloalkyl, cycloalkylalkyl, alkoxy, haloalkoxy, alkoxyalkyl, alkoxycarbonyl, alkoxycarbonylalkyl, alkylthioalkyl, aryl, arylalkyl and hetarylalkyl, or R$^7$ and R$^8$ together with the nitrogen atom to which they are attached form a ring which optionally contain one or more further heteroatoms selected from the group consisting of NH, NCH$_3$, NC$_2$H$_5$, oxygen and sulphur), or represents alkylthio, alkylsulphinyl, alkylsulphonyl, or represents a heterocyclyl radical selected from the group consisting of dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide (where in these heterocyclyl radicals two hydrogen atoms attached to the same carbon atom are optionally replaced by =CH$_2$, —CH$_2$—CH$_2$—, —CH$_2$—CH$_2$—CH$_2$— or —CH$_2$—CH$_2$—CH$_2$—CH$_2$—), morpholinyl, triazolinonyl, oxazolinyl, dihydrooxadiazinyl, dihydrodioxazinyl, dihydrooxazolyl, dihydrooxazinyl and pyrazolinonyl (where all the heterocyclyl radicals for their part are optionally substituted by alkyl, haloalkyl, alkoxy or alkoxyalkyl), or represents phenyl, wherein said phenyl is substituted by halogen, cyano, nitro, alkyl or haloalkyl, or represents a heteroaryl radial selected from the group consisting of pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl, wherein said heteroaryl radial is optionally substituted by halogen, nitro, alkyl, haloalkyl, alkoxy, haloalkoxy, alkoxyalkyl, alkylthio, alkylthioalkyl or cycloalkyl, or represents a heteroarylalkyl radical selected from the group consisting of triazolylalkyl, pyridylalkyl, pyrimidylalkyl oxadiazolylalkyl, wherein said heteroarylalkyl radical is optionally substituted by halogen or alkyl, and c represents a number selected from the group consisting of 0, 1, 2 and 3.

10. The compound according to claim 9, in which

R$^4$ represents a heterocyclyl radical selected from the group consisting of dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide (where in these heterocyclyl radicals two hydrogen atoms attached to the same carbon atom is optionally replaced by =CH$_2$, —CH$_2$—CH$_2$—, —CH$_2$—CH$_2$—CH$_2$— or —CH$_2$—CH$_2$—CH$_2$—CH$_2$—), morpholinyl, triazolinonyl, oxazolinyl, dihydrooxadiazinyl, dihydrodioxazinyl, dihydrooxazolyl, dihydrooxazinyl and pyrazolinonyl (where all the heterocyclyl radicals are optionally substituted by alkyl, haloalkyl, alkoxy, or alkoxyalkyl).

11. The compound according to claim 9, in which

E represents phenyl,

R$^4$ represents halogen, cyano, C$_1$-C$_6$-haloalkyl, C$_1$-C$_6$-alkoxy, C$_1$-C$_6$-haloalkoxy, dioxolanyl or dihydrodioxazinyl, and c represents 1, 2 or 3.

12. The compound according to claim 9, in which

E represents phenyl,

R$^4$ represents halogen, cyano, C$_1$-C$_4$-haloalkyl, C$_1$-C$_4$-alkoxy or C$_1$-C$_4$-haloalkoxy, and c represents 1 or 2.

13. A composition comprising at least one compound of formula (I) according to claim 9, and one or more extenders, surfactants, or combinations thereof.

14. A method for controlling pests comprising contacting a compound of formula (I) according to claim 9 with the pests, their habitat, or a combination thereof.

* * * * *